US011591584B2

(12) United States Patent
Striberny et al.

(10) Patent No.: US 11,591,584 B2
(45) Date of Patent: Feb. 28, 2023

(54) METHODS OF INACTIVATING A PROTEINASE OR AN ENZYMATICALLY ACTIVE FRAGMENT THEREOF

(71) Applicant: ARCTICZYMES AS, Tromsø (NO)

(72) Inventors: Bernd Ketelsen Striberny, Kvaløya (NO); Cathrine Pedersen, Tomasjord (NO); Jørn Remi Henriksen, Kvaløya (NO); Olav Lanes, Tromsø (NO); Marit Sjo Lorentzen, Krokelvdalen (NO)

(73) Assignee: ARCTICZYMES AS, Tromsø (NO)

( * ) Notice: Subject to any disclaimer, the term of this patent is extended or adjusted under 35 U.S.C. 154(b) by 0 days.

(21) Appl. No.: 16/978,613

(22) PCT Filed: Mar. 7, 2019

(86) PCT No.: PCT/EP2019/055724
§ 371 (c)(1),
(2) Date: Sep. 4, 2020

(87) PCT Pub. No.: WO2019/170809
PCT Pub. Date: Sep. 12, 2019

(65) Prior Publication Data
US 2020/0407701 A1     Dec. 31, 2020

(30) Foreign Application Priority Data
Mar. 7, 2018 (GB) .................... 1803654

(51) Int. Cl.
C12N 9/50 (2006.01)
C07H 1/08 (2006.01)
C07H 21/00 (2006.01)

(52) U.S. Cl.
CPC ............... C12N 9/50 (2013.01); C07H 1/08 (2013.01); C07H 21/00 (2013.01)

(58) Field of Classification Search
None
See application file for complete search history.

(56) References Cited

U.S. PATENT DOCUMENTS

| | | |
|---|---|---|
| 2003/0170617 A1 | 9/2003 | Pasloske |
| 2011/0111463 A1 | 5/2011 | Kubista et al. |
| 2011/0136180 A1 | 6/2011 | Bengtsson et al. |

FOREIGN PATENT DOCUMENTS

| | | |
|---|---|---|
| DE | 102005028295 A1 | 11/2006 |
| WO | 2017/006266 A1 | 1/2017 |

OTHER PUBLICATIONS

Chica et al. CurrOpin Biotechnol. Aug. 2005;16(4):378-84. (Year: 2005).*
Singh et al. Curr Protein Pept Sci. 2017, 18, 1-11 (Year: 2017).*
Accession Q3HUQ2. Nov. 8, 2005 (Year: 2005).*
UKIPO Combined Search and Examination Report under Sections 17 and 18(3) dated Nov. 30, 2018, GB Application No. GB1803654.1, pp. 1-7.
Sequence Listing for DE 10 2005 028 295.4 filed Jun. 18, 2005, pp. 1-3.
Ronny Helland et al., "The 1.8 Å crystal structure of a proteinase K-like enzyme from a psychrotroph Serratia species", The FEBS Journal, vol. 273, 2006, pp. 61-71.
Clustalw2, Retrieved from the Internet Sep. 2020: https://www.ebi.ac.uk/Tools/msa/clustalw2/, 1 Page.
Biorad, "PCR Reagents: SingleShot Cell Lysis RT-qPCR Kits," 2014, Retrieved from the Internet: https://www.bio-rad.com/webroot/web/pdf/lsr/literature/Bulletin_6604.pdf, pp. 1-4.
Sigma-Aldrich, "GenomePlex Single Cell Whole Genome Amplification K Protocol," Retrieved from the Internet Sep. 2020: https://www.sigmaaldrich.com/technical-documents/protocols/biology/single-cell-whole-genome-amplification-kit.html, pp. 1-5.
Atle Noralf Larsen, "Identification, characterization and structural determination of a proteinase K like enzyme from a psychrotrophic *Serratia* sp.," Doctoral Thesis submitted to University of Tromso, Norway, Apr. 2005, pp. 1-59.
Atle Noralf Larsen et al., "Structural basis for the S1-S4 specificity of two enzymes belonging to the Proteinase K family of serine peptidases," Paper III referenced in with Doctoral Thesis submitted to University of Tromso, Norway, Apr. 2005, pp. 1-26.
Jurgen Bajorath et al., "The enzymatic activity of proteinase K is controlled by calcium," European Journal of Biochemistry, vol. 176, No. 2, 1988, pp. 441-447.
Richard H. Tullis et al., "Calcium protects DNase I from proteinase K: A new method for the removal of contaminating RNase from DNase I," Analytical Biochemistry, vol. 107, Issue 1, Sep. 1980, pp. 260-264 (Abstact Submitted).

(Continued)

*Primary Examiner* — Christian L Fronda
(74) *Attorney, Agent, or Firm* — Siepmann IP, PLLC

(57) ABSTRACT

The invention provides a composition comprising a proteinase or an enzymatically active fragment thereof, said proteinase comprising the amino acid sequence of SEQ ID NO: 1 or comprising an amino acid sequence which is at least about 70% identical to SEQ ID NO: 1, wherein i) the concentration of free calcium in said composition is ≤about 80 µM; or ii) the concentration of monovalent salt in said composition is ≥about 20 mM. Under such conditions, the proteinases and enzymatically active fragments thereof are inducibly thermolabile. The invention further provides samples comprising one or more polypeptides and a proteinase or an enzymatically active fragment thereof, said proteinase comprising the amino acid sequence of SEQ ID NO: 1 or comprising an amino acid sequence which is at least about 70% identical to SEQ ID NO: 1, wherein i) the concentration of free calcium in said sample is ≤about 80 µM; or ii) the concentration of monovalent salt in said sample is ≥about 20 mM. The invention further provides methods comprising the inactivation of such proteinases or enzymatically active fragments thereof, wherein said method comprises the step of heating the sample to inactivate said proteinase or enzymatically active fragment, and wherein i) the concentration of free calcium in said sample is ≤about 80 µM; or ii) the concentration of monovalent salt in said sample is ≥about 20 mM.

9 Claims, 5 Drawing Sheets
Specification includes a Sequence Listing.

(56) References Cited

OTHER PUBLICATIONS

Moshe Mevarech et al., "Halophilic enzymes: proteins with a grain of salt," Biophysical Chemistry, vol. 86, 2000, pp. 155-164.
David Svec et al., "Identification of inhibitors regulating cell proliferation and FUSDDIT3 expression in myxoid liposarcoma using combined DNA, mRNA, and protein analyses," Laboratory Investigation, vol. 98, 2018, pp. 957-967.
PCT International Search Report and Written Opinion dated May 2, 2019, International Application No. PCT/EP2019/055724, pp. 1-16.
Atle Noralf Larsen et al., "Characterization of a recombinantly expressed proteinase K-like enzyme from a psychrotrophic *Serratia* sp", The FEBS Journal, vol. 273, No. 1, 2006, pp. 47-60.
V. G. H. Eijsink et al., "The role of calcium ions in the stability and instability of a thermolysin-like protease", Protein Science, vol. 20, 2011, pp. 1346-1355.
Alison J. Moran et al., "Heat-labile proteases in molecular biology applications", FEMS Microbiology Letters, vol. 197, 2001, pp. 59-63.

\* cited by examiner

METHODS OF INACTIVATING A PROTEINASE OR AN ENZYMATICALLY ACTIVE FRAGMENT THEREOF

CROSS-REFERENCE TO RELATED APPLICATIONS

This application is a U.S. National Stage Application of PCT/EP2019/055724, filed on Mar. 7, 2019, which claims the benefit of GB 1803654.1, filed on Mar. 7, 2018, each of which is herein incorporated by reference in its entirety.

REFERENCE TO SEQUENCE LISTING SUBMITTED VIA EFS-WEB

Pursuant to the EFS-Web legal framework and 37 CFR §§ 1.821-825 (see MPEP § 2442.03(a)), a Sequence Listing in the form of an ASCII-compliant text file (entitled "PCT Seq List as Filed.txt" created on Dec. 26, 2019, and 13,700 bytes in size) is submitted concurrently with the instant application, and the entire contents of the Sequence Listing are incorporated herein by reference in its entirety.

The present invention relates to compositions comprising a proteinase with inducible thermolability, and uses thereof, particularly in the isolation of nucleic acids.

Proteinases (also termed peptidases, proteases and proteolytic enzymes) are capable of hydrolyzing peptide bonds in proteins. Proteinases are used extensively in a wide range of processes in industry, biotechnology and molecular biology research techniques. For instance, proteinases are used in the digestion of unwanted proteins during nucleic acid purification, in the preparation of recombinant antibody fragments, in peptide sequencing and in proteolytic digestion of proteins in proteomics.

To successfully extract nucleic acids from a sample, lysis of cell walls/membranes is necessary. Various physical or chemical methods can be employed, which can be enhanced by the addition of a protease. Removal of membrane lipids is then achieved by application of detergents or surfactants or by osmotic lysis in hypotonic solutions. The removal of proteins from the sample using proteinases is then considered best practice. Proteinases digest contaminating, i.e. unwanted, proteins, polypeptides and peptides present in the sample by hydrolysing peptide bonds. Proteinases also degrade any nucleases and other enzymes that may be present in the sample and that may otherwise degrade the nucleic acids.

The removal of protein is particularly important during nucleic acid purification in the preparation of nucleic acid samples for amplification reactions (e.g. PCR and RT-PCR). In the cell, nucleic acids typically exist bound to proteins. For instance, genomic DNA in eukaryotic cells is bound to histones, which achieve tight packaging of DNA into chromatin. Many molecular biology techniques, such as PCR, require naked DNA, i.e. DNA not bound to histones, because the tight packaging of DNA in chromatin reduces the access that DNA-interacting enzymes such as polymerases and nucleases have to the nucleic acids.

Nucleic acid purification is a multi-step process which involves time and cost and sample loss. Sample loss is particularly undesirable when the starting amount of nucleic acid in the sample is small, e.g. when isolated from a few hundred cells or less, e.g. from small needle aspirated biopsies or liquid biopsies.

The most commonly used proteolytic enzyme in nucleic acid purification is Proteinase K (EC 3.4.21.64). The enzyme was originally discovered in extracts of the fungus Engyodontium album (formerly Tritirachium album). Proteinase K is a non-specific serine endopeptidase which catalyzes the cleavage of peptide bonds at the carboxylic side of aromatic, aliphatic, or hydrophobic amino acid residues. Proteinase K's broad specificity permits its utility in the digestion of unwanted proteins in samples. Proteinase K also rapidly inactivates the nucleases which might otherwise degrade nucleic acids present in the sample. Proteinase K is active in the presence of chemicals used in the DNA extraction process that denature other proteins, such as SDS and urea, chelating agents such as EDTA, sulfhydryl reagents, trypsin inhibitors and chymotrypsin inhibitors. Proteinase K has an optimum activity in the range of 50-65° C., typically about 55° C.

When proteinase K is used in the purification of a sample, it is necessary to inactivate or remove the proteinase K prior to the addition of downstream proteins/enzymes, e.g. polymerases and reverse transcriptases. Without such inactivation or removal, the proteinase will degrade downstream proteins/enzymes due to its non-specific activity.

Proteinase K may be removed from the sample, for instance by phenol extraction or CsCl isopycnic ultracentrifugation. Alternatively, the volume of the sample can be increased, thereby diluting the proteinase K activity therein. However, the act of physically removing the enzyme from the sample introduces the risk of contamination, as well as the risk of losing the desired product. Dilution is not ideal in most instances, particularly when the sample size is small.

Protocols for inactivation of Proteinase K vary, but typically involve heating to a high temperature. However, in many cases, the heat necessary to inactivate the protease results in degradation of one or more desired products in the sample. Protocols for the inactivation of Proteinase K include heating to 75° C. for 5 minutes (Bio-Rad protocol), heating to 95° C. for 10 minutes (New England BioLabs protocol), heating to 70° C. for 15 minutes (Qiagen protocol), sometimes in combination with reagents. The use of such high temperatures is relatively harsh on the sample of interest.

Therefore, there remains a need for alternative methods of degrading proteins, particularly during nucleic acid purification protocols, that permit shortened workflows without loss of the desired material from the sample and which do not involve harsh proteinase inactivation conditions.

Proteinase X (also termed "*Serratia* peptidase" and "SPRK") is a proteinase K-like proteinase isolated from *Serratia* sp. Studies of Proteinase X (Larsen et al., (2006) FEBS Journal 273: 47-60) have determined that it, like Proteinase K, has a high thermal stability, and further that Proteinase X actually has a higher temperature optimum (70° C.) than Proteinase K (55° C.). Larsen et al. also demonstrates that Proteinase X retained full enzyme activity after heating at 50° C. for 30 minutes, and retains much more activity than Proteinase K after heating to 50° C. in the presence of various concentrations of SDS (a surfactant commonly used in the isolation of nucleic acids from samples). Larsen et al. teaches that Proteinase X does not display the typical thermolabile features of enzymes isolated from cold-adapted organisms.

The present inventors have for the first time determined that, surprisingly, thermolability of Proteinase X is induced when the proteinase is present in a composition with a low concentration of free calcium ions. The inventors have determined that it is not necessary to remove calcium ions that may be bound to the proteinase and contribute to its stability and structure, e.g. by using EDTA. Rather, the mere absence or low concentration of free calcium ions in the composition is, surprisingly, sufficient to induce the thermolability of Proteinase X. The present inventors have for the first time also determined that, surprisingly, thermolability of Proteinase X is induced when the proteinase is present in the composition with particular concentrations of monovalent salt.

Such inducible thermolabile properties are unexpected, and are not observed with the gold-standard proteinase used in molecular biology applications; Proteinase K. The inventors' findings permit the advantageous use of Proteinase X with inducible thermolability in a wide range of molecular biology applications.

Thus, in one aspect the present invention provides a composition comprising a proteinase or an enzymatically active fragment thereof, said proteinase comprising the amino acid sequence of SEQ ID NO: 1 or comprising an amino acid sequence which is at least about 70% identical to SEQ ID NO: 1, wherein
i) the concentration of free calcium in said composition is ≤about 80 µM; or
ii) the concentration of monovalent salt in said composition is ≥about 20 mM.

Preferably, the concentration of free calcium in said composition is ≤about 80 µM and the concentration of monovalent salt in said composition is ≥about 20 mM.

The invention relates to proteinases comprising the sequence of SEQ ID NO: 1 and to proteinases comprising a sequence which is at least about 70% identical to SEQ ID NO: 1, which are termed "variants of SEQ ID NO: 1", "variant proteinases" or merely "variants" herein. By definition, the variants of SEQ ID NO: 1 of the invention are also proteinases according to the invention, i.e. they possess proteinase activity. A reference herein to a proteinase of the invention is a reference to the proteinase of SEQ ID NO: 1 and to the variants of the invention described herein. A reference anywhere herein to a proteinase (or variant proteinase) is also a reference to enzymatically active fragments thereof, unless context dictates otherwise.

Preferably the composition is a solution, preferably an aqueous solution. The term "solution" as used herein means a liquid mixture in which one or more minor components (solutes) are uniformly distributed within a major component (solvent). Typically, the minor component (solute) of a solution is soluble in the major component (solvent). However, as used herein, the term "solution" also comprises mixtures in which the minor component (solute) is not soluble in the major component (solvent), i.e. the term "solution" as used herein also encompasses mixtures, i.e. dispersions, in which the major component is a liquid phase and the minor component comprises particles that are insoluble in the liquid phase. Preferably, the major component, i.e. solvent, i.e. liquid phase, is water. Preferably, the solution comprises water. The solutions of the present invention comprise at least a proteinase or an enzymatically active fragment thereof of the invention as a minor component.

In a preferred embodiment, the solution of the invention is a reagent for application to a sample comprising one or more polypeptides. Such a reagent is applied to a sample in order for the proteinase in said reagent to digest said one or more polypeptides present in the sample. Preferably, the sample comprises multiple polypeptides. In this embodiment, the solution preferably comprises a proteinase or enzymatically active fragment thereof of the invention and no further enzymes.

Preferably, the composition also comprises a buffer. Suitable buffers are well known in the art and any such buffer may be used. It would be within the competencies of the person of ordinary skill in the art to identify a suitable buffer and an inclusion range thereof for their intended purposes. Preferably, the buffer has a buffering range of pH 6.5 to 9.5, preferably pH 6.8 to 9.2, more preferably pH 7 to 9, more preferably pH 7.5 to 8.5, more preferably about pH 8. Preferably, the buffer is Tris or HEPES. Preferably, the buffer is present in the composition at a concentration of 1 to 250 mM, more preferably 10 to 200 mM, more preferably 20 to 150 mM, more preferably 25 to 100 mM.

If present, preferably Tris-HCl is present at a concentration of 25 to 200 mM, more preferably 50 to 150 mM, more preferably about 100 mM. If present, preferably HEPES is present at a concentration of 5 to 50 mM, more preferably 10 to 40 mM, more preferably 20 to 30 mM, more preferably about 25 mM.

Preferably, the compositions and samples of the present invention have a pH of 6.5 to 9.5, preferably 6.8 to 9.2, more preferably 7 to 9, more preferably 7.5 to 8.5, more preferably about 8.0.

The compositions and samples of the present invention may further comprise DMSO. If present, preferably DMSO is present at a concentration of 0.1 to 5% w/w, more preferably 0.5 to 2.5% DMSO, more preferably about 1% DMSO.

The term "sample" refers to any composition comprising one or more polypeptides other than the proteinase of the invention.

In a further aspect the present invention provides a sample comprising one or more polypeptides and a proteinase or an enzymatically active fragment thereof, said proteinase comprising the amino acid sequence of SEQ ID NO: 1 or comprising an amino acid sequence which is at least about 70% identical to SEQ ID NO: 1, wherein
i) the concentration of free calcium in said sample is ≤about 80 µM; or
ii) the concentration of monovalent salt in said sample is ≥about 20 mM.

Preferably, the concentration of free calcium in said sample is ≤about 80 µM and the concentration of monovalent salt in said sample is ≥about 20 mM.

Samples not comprising a proteinase or an enzymatically active fragment as described herein are not an aspect of the present invention. References herein to "samples of the invention" are references only to samples that do comprise a proteinase or enzymatically active fragment as described herein.

The following discussion of preferred and optional features and embodiments of "samples" applies both to samples of the invention and to samples that are not part of the invention but are samples to which a composition of the invention may be applied.

The proteinases of the invention have utility in methods of purification, i.e. isolation, i.e. extraction of biological molecules of interest from samples comprising contaminating, i.e. unwanted, polypeptides. Thus, in a preferred embodiment the sample comprises one or more contaminating polypeptides and one or more biological molecules of interest. As used herein, the term "contaminating polypeptide" is synonymous with "unwanted polypeptide" and refers to any polypeptide in a sample other than the proteinases of the invention and any polypeptide of interest. Thus, contaminating polypeptides are those to be digested by the proteinases of the invention in order to purify or modify the one or more biological molecules of interest.

The proteinases of the invention also have utility in methods of releasing a biological molecule of interest from a molecule, preferably a polypeptide, fused via one or more peptide bonds thereto, by hydrolysing one or more of said peptide bonds. Thus, in a preferred embodiment, the sample comprises a biological molecule of interest fused to a molecule, preferably a polypeptide, via one or more peptide bonds. The one or more peptide bonds are capable of being cleaved by the proteinase or enzymatically active fragment thereof of the invention.

As used herein, the term "biological molecule of interest" refers to any biological molecule in a sample also comprising one or more contaminating polypeptides, wherein purification of said biological molecule from said sample is desired, or wherein release of said biological molecule from a molecule fused thereto via one or more peptide bonds is desired. Preferably, the biological molecule of interest is a nucleic acid molecule, preferably a DNA or RNA molecule. Alternatively the biological molecule of interest is itself a polypeptide. The biological molecule of interest is not a proteinase or enzymatically active fragment thereof of use in the invention.

Preferably, the sample comprises cellular matter. Preferably, the sample comprises a crude cell extract. Preferably, the sample comprises a partially purified cell extract. Preferably, the sample comprises a population of cells. The cells in said sample may be intact or lysed, preferably lysed. Preferably, the sample comprises a tissue sample or one or more body fluids. Preferably, the sample is a fine needle biopsy. Preferably, the sample comprises encapsulated viruses. Proteinases may be used to digest the protein capsule of viruses in order to release the RNA/DNA therein for identification, quantification and/or amplification.

Preferably the samples of the invention have a volume of ≥10 µl. Preferably the samples of the invention have a volume of ≤1000 µl, more preferably ≤500 µl, more preferably ≤300 µl, more preferably ≤250 µl, more preferably ≤200 µl, more preferably ≤150 µl, more preferably ≤100 µl, more preferably ≤75 µl, more preferably ≤50 µl. Alternatively, the sample is a microfluidic sample. Preferably the microfluidic samples of the invention have a volume of ≥0.01 µl. Preferably the microfluidic samples of the invention have a volume of ≤10 µl, preferably ≤5 µl more preferably ≤1 µl, more preferably ≤0.5 µl more preferably ≤0.1 µl.

The term "polypeptide" as used herein refers to proteins, polypeptides, peptides oligopeptides and tripeptides, i.e. any molecule comprising three or more amino acids linked via peptide bonds, which may be hydrolysed by a proteinase of the invention. Proteinase X is known to hydrolyse peptides as short as three amino acids in length. The terms "protein", "polypeptide" and "peptide" are used interchangeably herein and use of each is expressly intended to refer to any and all of proteins, polypeptides and peptides. Thus, the polypeptides present in a sample described herein are substrates for the proteinases or enzymatically active fragments thereof of the invention. Clearly, the proteinases and enzymatically active fragments thereof are themselves polypeptides. However, the term "polypeptide" as used herein expressly excludes the proteinases and enzymatically active fragments thereof of use in the invention.

The terms "digest", "hydrolyse, "degrade" and "cleave" are used interchangeably herein and refer to the hydrolysis of peptide bonds within polypeptides in a sample. Digestion may be partial digestion or complete digestion. The proteinases of use in the invention are non-specific and will, given enough time, completely digest proteins in a sample under conditions that permit enzyme function.

The compositions and samples of the invention comprise a proteinase or an enzymatically active fragment thereof, said proteinase comprising the amino acid sequence of SEQ ID NO: 1 or comprising an amino acid sequence which is at least about 70% identical to SEQ ID NO: 1.

```
The amino acid sequence of SEQ ID NO: 1 is:
ADQPSPTWGIDRIDQRNLPLDNNYHTDYDGSGVTAFVIDTGVLNTHNEFG

GRASSGYDFIDNDYDATDCNGHGTHVAGTIGGSTYGVAKNVNVVGVRVLN

CSGSGSNSGVIAGINWVKNNASGPAVANMSLGGGASQATDDAVNAAVAAG

ITFVVAAGNDNSNACNYSPARAADAITVGSTTSNDSRSSFSNYGTCLDIY

APGSSITSSWYTSNSATNTISGTSMASPHVAGVAALYLDENPNLSPAQVT

NLLKTRATADKVTDAKTGSPNKLLFSLANDD
```

The proteinase of SEQ ID NO: 1 is based on the amino acid sequence of Proteinase X from a marine *Serratia* species isolated in the North of Norway as described in Larsen et al., (2006) *FEBS Journal* 273: 47-60. Proteinase X is a proteinase K-like proteinase [E.C. 3.4.21]. The terms "Proteinase X", "Protease X", "ProtX", "PRX", "peptidase X", "*Serratia* peptidase" and "SPRK" are used interchangeably herein. Preferably, the proteinase of the invention is derived from *Serratia proteamaculans*. Proteinase X is a serine peptidase.

The gene encoding Proteinase X has 1890 base pairs (SEQ ID NO: 2) and encodes a precursor protein of 629 amino acids (65.5 kDa, SEQ ID NO: 3).

```
SEQ ID NO: 2:
atgcataagaaacatttaatagcagtcgcagtcgcaacgggacttgctta cttccctgttaacgctaatgaataccaagcgactatggtaaatgtcccac aatctaaagccatcaaagatacttacatcgttgtattcaataccccaagt gttcttaatctaagtaataacaacaccatagctgaattcgcggttcaaca agccgagagtttagtcaatcaatatgatgtcagagtgatgaaaaactttg gcaatgtgctcaacggtgtactcatcaatgccagtgcccaacaagttaaa gcactgcttaaagatccaaacgtgaagtacgtagaacaagatcaagtgat gtcagtaacgcccatgatggaagccaatgcggaccaaccgagtccgacct ggggcatagacagaatcgatcaacgcaacttgccattggataacaactac cacacggattacgatggatctggtgtgaccgcctttgttattgatactgg ggtgcttaatacacacaatgagtttggcggccgcgcaagcagtggctatg actttatcgataatgattacgatgcgactgactgtaacggtcatggtacc catgtggcggggacgattggcggctcaacctacggtgtcgcgaaaaacgt caatgtggtgggcgtcagagtgcttaactgttcaggttctggcagtaact ctgcgtgattgcagggataaactgggtgaaaaacaatgcttctggcccc gctgtcgcgaacatgagtttaggggcggcgcctcccaagccacggatga tgccgtcaatgccgctgttgccgcagggatcaccttcgtcgtcgcagccg gcaatgacaatagtaatgcctgtaattattcacctgctcgtgccgcagat gccatcactgtcggttcaaccaccagtaacgattcccgctcgagttttc taactacgggacttgccttgatatctatgcgcccggttcgagcataactt cctcttggtatacctcaaattcggcgactaataccattagtggcacctca atggcttccccccatgtggcaggcgtcgcggcattatacttagatgaaaa
```

-continued

```
tcctaacctctccccgcacaggtgactaacttactcaagacgcgcca ctgcggacaaagtcacagatgctaagacaggctcaccgaataagttactt ttcacttgcaaacgatgatggaggctgtggcaacgattgcccagttgacg agactcagctgcaaaataatgtgggtattgcgatcagtggagccacaggt tcagcgacttattactatatcgatgtccccgcaaatgcagcaagtttagg catcaacctcgcggggggctctggcgatgcggatatttatgtgagccaag gacaaaaaccgactacgaccagctatcaatgccgcccatatcaaaatggc aacaatgagagctgtaatttcactgcacctacggcgggtcgttggtacgt gatggttcaaggctatagcaattatgccaacgcccagctgacagctagct acaacctcaatggcggcggaaattgtaccgatgcgaactgcttaagcaat ggcgtacccgtcacgaatttaagcggcagaacgggaactgaagccctgta taaaatcgtcgtccctgcgaatagccaactcagtattaccaccagtggcg ggactggtgacgtggatctgtatgtcaaagcagggactgtcccaacgacc accagctatgattgtcgtccctataaaaacggtaacaatgaaagctgttc aatcaccgtgactcaagcgggaacttaccatgtgatgttacgtggttatg ctaattactcgagcgttcagctgagtgcaagctactag

SEQ ID NO: 3:
MHKKHLIAVAVATGLAYFPVNANEYQATMVNVPQSKAIKDTYIVVFNTPS

VLNLSNNNTIAEFAVQQAESLVNQYDVRVMKNFGNVLNGVLINASAQQVK

ALLKDPNVKYVEQDQVMSVTPMMEANADQPSPTWGIDRIDQRNLPLDNNY

HTDYDGSGVTAFVIDTGVLNTHNEFGGRASSGYDFIDNDYDATDCNGHGT

HVAGTIGGSTYGVAKNVNVVGVRVLNCSGSGSNSGVIAGINWVKNNASGP

AVANMSLGGGASQATDDAVNAAVAAGITFVVAAGNDNSNACNYSPARAAD

AITVGSTTSNDSRSSFSNYGTCLDIYAPGSSITSSWYTSNSATNTISGTS

MASPHVAGVAALYLDENPNLSPAQVTNLLKTRATADKVTDAKTGSPNKLL

FSLANDDGGCGNDCPVDETQLQNNVGIAISGATGSATYYYIDVPANAASL

GINLAGGSGDADIYVSQGQKPTTTSYQCRPYQNGNNESCNFTAPTAGRWY

VMVQGYSNYANAQLTASYNLNGGGNCTDANCLSNGVPVTNLSGRTGTEAL

YKIVVPANSQLSITTSGGTGDVDLYVKAGTVPTTTSYDCRPYKNGNNESC

SITVTQAGTYHVMLRGYANYSSVQLSASY
```

The proteinase of SEQ ID NO: 3 consists of a 126 residue N-terminal pre-pro sequence, a 278 residue catalytic domain and two C-terminal domains (repeated sequences) together consisting of 225 residues.

The enzyme is recombinantly expressed in *Pichia pastoris* as an active 385 amino acid, ~40.2 kDa peptidase having the sequence of SEQ ID NO: 4:

```
NEYQATMVNVPQSKAIKDTYIVVFNTPSVLNLSNNNTIAEFAVQQAESLV

NQYDVRVMKNFGNVLNGVLINASAQQVKALLKDPNVKYVEQDQVMSVTPM

MEANADQPSPTWGIDRIDQRNLPLDNNYHTDYDGSGVTAFVIDTGVLNTH

NEFGGRASSGYDFIDNDYDATDCNGHGTHVAGTIGGSTYGVAKNVNVVGV

RVLNCSGSGSNSGVIAGINWVKNNASGPAVANMSLGGGASQATDDAVNAA

VAAGITFVVAAGNDNSNACNYSPARAADAITVGSTTSNDSRSSFSNYGTC

LDIYAPGSSITSSWYTSNSATNTISGTSMASPHVAGVAALYLDENPNLSP

AQVTNLLKTRATADKVTDAKTGSPNKLLFSLANDD
```

The expressed proteinase of SEQ ID NO: 4 excludes both C-terminal domains other than the first three residues of the first C-terminal domain, and excludes the initial 22 residues of the SEQ ID NO: 3 N-terminal pre-pro domain. This form of the protein may be purified.

The recombinant expression of Proteinase X in *E. coli* is described in Larsen et al., (2006) FEBS Journal 273: 47-60.

Subsequent to expression, the enzyme is converted by autolytic degradation into a mature ~34 kDa, 281 residue mature protein, which contains the catalytic domain and three C-terminal amino acid residues, and which retains full catalytic activity (SEQ ID NO: 1).

Residues 1 to 104 of SEQ ID NO: 4 correspond to residues 23 to 126 of SEQ ID NO: 3. Residues 1 to 281 of SEQ ID NO: 1 correspond to residues 105 to 385 of SEQ ID NO: 4 and correspond to residues 127 to 407 of SEQ ID NO: 3.

Thus, In each and all aspects and embodiments of the present invention, the proteinase may comprise the amino acid sequence of SEQ ID NO: 1, SEQ ID NO: 3 or SEQ ID NO: 4, preferably SEQ ID NO: 1. SEQ ID NOs: 3 and 4 being precursor/immature forms of the proteinase of SEQ ID NO: 1. The skilled person would appreciate that use or presence of a proteinase of SEQ ID NO: 3 or 4 would, due to further autolytic processing, result in the use or presence of a proteinase of SEQ ID NO: 1. For brevity, reference anywhere herein to SEQ ID NO: 1 is expressly intended to refer also to SEQ ID NO: 3 and/or SEQ ID NO: 4.

The compositions and samples of the invention comprise a proteinase or an enzymatically active fragment thereof, said proteinase comprising the amino acid sequence of SEQ ID NO: 1 or comprising an amino acid sequence which is at least about 70% identical to SEQ ID NO: 1.

By "at least about 70%" it is meant that the sequence identity may be at least 69%, 69.5% or 69.9%.

In preferred embodiments, the proteinase of the invention comprises, or consists of, an amino acid sequence that is at least 71%, at least 72%, at least 73%, at least 74%, or at least 75%, preferably at least 80%, 85%, 90% or 95%, e.g. at least 98% or 99% or 99.5%, identical to SEQ ID NO: 1.

Percentage sequence identity according to the invention can be calculated using any of the widely available algorithms, e.g. using the ClustalW2 Multiple Sequence Alignment program (http://www.ebi.ac.uk/Tools/clustalW2) using default parameters (DNA Gap Open Penalty=15.0; DNA Gap Extension Penalty=6.66; DNA Matrix=Identity; Protein Gap Open Penalty=10.0; Protein Gap Extension Penalty=0.2; Protein matrix=Gonnet; Protein/DNA ENDGAP=−1; Protein/DNA GAPDIST=4).

Percentage identity is preferably determined between the N-terminal Ala residue (residue 1) and the C-terminal Asp residue (residue 281) in SEQ ID NO: 1, above, after alignment of SEQ ID NO: 1 and the variant sequence.

Variants of SEQ ID NO: 1 include amino acid sequences in which one or more amino acids of said SEQ ID Nos have undergone conservative substitution or have been replaced with a modified version of said one or more amino acids or an amino acid which is not naturally occurring, e.g. D isomers of said one or more amino acids. Preferably, such substitutions and modifications are silent substitutions and modifications in that the modified forms of the exonucleases of the invention have the same enzymatic and inactivation characteristics as the unmodified forms.

In some embodiments, the proteinase of the invention comprises (or consists of) an amino acid sequence that has single or multiple amino acid alterations (additions, substitutions, insertions or deletions) compared to SEQ ID NO: 1. Such sequences preferably may contain up to 10, e.g. only 1, 2, 4, 4, 5, 6, 7, 8, 9 or 10, preferably up to 5, e.g. only 1, 2, 3, 4 or 5, preferably 1, 2 or 3, more preferably 1 or 2, altered amino acids. Preferably, the number of alterations is determined between the N-terminal Ala residue (residue 1) and the C-terminal Asp residue (residue 281) in SEQ ID NO: 1 above, after alignment of SEQ ID NO: 1 and the variant sequence.

Preferably, alterations are silent alterations in that the altered proteinases of the invention have the same enzymatic and inactivation characteristics as the unaltered forms. Substitutions can be with conservative or non-conservative amino acids. Preferably, said alterations are conservative amino acid substitutions. Said alternations may be replacement with a modified version of one or more amino acids of SEQ ID NO: 1, or replacement with an amino acid which is not naturally occurring, e.g. D isomers of amino acids.

A proteinase comprising an amino acid sequence which is at least about 70% identical to SEQ ID NO: 1 may be obtained from a prokaryotic organism found in cold water niches. By "prokaryote" is meant any organism that lacks a cell nucleus, i.e. any organism from the domains Bacteria and Archea. Preferably, the organism is a bacterium. Preferably, the organism is not a eukaryote, e.g. an organism classified in the taxonomic kingdoms Animalia, Plantae, Fungi or Protista. More preferably, the organism is selected from the genera *Shewanella, Halomonas, Vibrio, Psychromonas, Moritella* and *Serratia*, preferably *Serratia*.

In some embodiments, the compositions and samples of the invention comprise a proteinase or an enzymatically active fragment thereof, said proteinase comprising the amino acid sequence of SEQ ID NO: 3 or 4 or comprising an amino acid sequence which is at least about 70% identical to SEQ ID NO: 3 or 4. The passage elsewhere herein referring to SEQ ID NO: 1 apply mutatis mutandis to SEQ ID NO: 3 and SEQ ID NO: 4.

Preferably, the proteinase of the invention consists of the amino acid sequence of SEQ ID NO: 1, 3 or 4 or consists of an amino acid sequence which is at least about 70% identical to SEQ ID NO: 1, 3 or 4.

Preferably, the proteinase of the invention comprises the amino acid sequence of SEQ ID NO: 1, 3 or 4. In some embodiments, the proteinase of the invention consists of the amino acid sequence of SEQ ID NO: 1, 3 or 4.

Preferably, the proteinase of the invention consists of the amino acid sequence of SEQ ID NO: 1 or consists of an amino acid sequence which is at least about 70% identical to SEQ ID NO: 1.

Preferably, the proteinase of the invention comprises the amino acid sequence of SEQ ID NO: 1. In some embodiments, the proteinase of the invention consists of the amino acid sequence of SEQ ID NO: 1.

The proteinases of the invention may comprise further amino acids N-terminal or C-terminal of the SEQ ID NO: 1 or SEQ ID NO: 4 sequence. Preferably, such further amino acids are identical to the respectively positioned amino acids found N- or C-terminal of the SEQ ID NO: 1 sequence within the 629 amino acid sequence of SEQ ID NO: 3. Preferably, the proteinase comprises 1 to 50, more preferably 1 to 40, more preferably 1 to 30, more preferably 1 to 20, more preferably 1 to 10, i.e. 1, 2, 3, 4, 5, 6, 7, 8, 9 or 10 amino acids N-terminal and/or C-terminal of the SEQ ID NO: 1 or SEQ ID NO: 4 sequence, preferably wherein said N- and/or C-terminal amino acids are identical to the respective amino acids found N- and/or C-terminal of the SEQ ID NO: 1 or SEQ ID NO: 4 sequence within the sequence of SEQ ID NO: 3.

The proteinases present in the solutions or samples of the invention may be in a modified form, e.g. in the form of fusion proteins in which they are fused, directly or indirectly via a peptide linker sequence, to a further peptide at the N-terminus and/or the C-terminus. Preferably, an additional N-terminal peptide, and if present linker sequence, together comprise a sequence 1 to 50, more preferably 1 to 40, more preferably 1 to 30, more preferably 1 to 20, more preferably 1 to 10, i.e. 1, 2, 3, 4, 5, 6, 7, 8, 9 or 10 amino acids in length. Preferably, an additional C-terminal peptide, and if present linker sequence, together comprise a sequence 1 to 50, more preferably 1 to 40, more preferably 1 to 30, more preferably 1 to 20, more preferably 1 to 10, i.e. 1, 2, 3, 4, 5, 6, 7, 8, 9 or 10 amino acids in length.

Thus, in one embodiment the present invention provides a composition comprising a proteinase or an enzymatically active fragment thereof, said proteinase comprising the amino acid sequence of SEQ ID NO: 1 or comprising an amino acid sequence which is at least about 70% identical to SEQ ID NO: 1, wherein
i) the concentration of free calcium in said composition is ≤about 80 µM; or
ii) the concentration of monovalent salt in said composition is ≥about 20 mM, and wherein said proteinase or enzymatically active fragment thereof further comprises a further peptide sequence that is N-terminal and/or a further peptide sequence that is C-terminal to the amino acid sequence of SEQ ID NO: 1 or the amino acid sequence which is at least about 70% identical to SEQ ID NO:1.

The further peptide sequence(s) may be useful in a process for the secretion, isolation, solubilisation and/or purification or identification of the proteinases, or to tether the proteinases to a solid support. Suitable peptide sequences are well known in the art and any such sequence may be used. Suitable N- and C-terminal sequences include, for instance, histidine tags, preferably comprising 1 to 20, more preferably 5 to 15, more preferably 6, 7, 8, 9, 10, 11 or 12 histidine residues, most preferably 6 or 12 histidine residues.

Thus, the proteinases of the invention may be modified proteinases. Further modifications include the introduction of small chemical groups to available atoms of the polypeptide, e.g. protecting groups for the N and C termini or the R-groups of non-essential amino acid residues within the polypeptide. In other embodiments the proteinases of the invention may be provided immobilised on a solid support, e.g. a solid support selected from particles, pellets, beads, sheets, gels, filters, membranes, fibres, capillaries, chips, micro titre strips, slides, tubes, plates or wells etc. Preferably, the support is magnetic (preferably paramagnetic or superparamagnetic) e.g. magnetic particles, for instance magnetic beads and pellets. Still further modified forms include dimers or trimers of the proteinases of the invention. Such entities may be homogeneous or heterogeneous in their monomer composition.

Preferably, such modifications are silent in that the modified forms of the proteinases of the invention have the same enzymatic and inactivation characteristics as the unmodified forms.

Enzymatically active fragments of proteinases and variant proteinases of the invention are also provided. Enzymatically active fragments are fragments that have proteinase activity. Enzymatically active fragments may comprise at least 225, preferably at least 235, preferably at least 250, more preferably at least 260, at least 270, at least 271, 272, 273 or 274, more preferably at least 275, 276, 277, 278, 279 or 280 amino acids of the SEQ ID NO: 1 sequence.

Preferably the enzymatically active fragments of the invention comprise an N-terminal truncation of no more than 5 amino acids, preferably no more than 4, 3, 2 or 1 amino acids of the SEQ ID NO: 1 sequence. Alternatively or in addition, the enzymatically active fragments of the invention preferably comprise a C-terminal truncation of no more than 30 amino acids, preferably no more than 29, 28, 27, 26, 25, 24, 23, 22, 21, 20, 19, 18, 17, 16, 15, 14, 13, 12, 11, 10, 9, 8, 7, 6, 5, 4, 3, 2 or 1 amino acids of the SEQ ID NO: 1 sequence.

Alternatively viewed, the length of the enzymatic fragments of the invention is preferably at least 80%, preferably at least 85%, preferably at least 90%, 91%, 92%, 93%, 94%, 95%, 96%, 97%, 98%, 99% or 99.5% of the length of SEQ ID NO: 1, or of the length of the amino acid sequence that is at least 70% identical to SEQ ID NO: 1.

The enzymatic fragments of the invention are themselves preferably at least 70%, preferably at least 80%, at least 85% or at least 90%, more preferably at least 95% (e.g. at least 98% or 99% or 99.5%), or 100% identical to the corresponding portion of SEQ ID NO: 1. Methods for determining percentage identity are described above.

Throughout the present application, a reference to a proteinase of the invention is also a reference to an enzymatically active fragment thereof, unless context dictates otherwise.

A proteinase (also termed a peptidase or protease) is an enzyme that performs proteolysis, i.e. protein catabolism by hydrolysis of peptide bonds. Thus, a proteinase according to the present invention is an enzyme with proteinase activity, i.e. protease activity, i.e. peptidase activity. The variants and enzymatically active fragments of the invention also possess proteinase activity.

The proteinases of the invention that are variants or modified forms of SEQ ID NO: 1 display at least 70%, preferably at least 80%, more preferably at least 85%, at least 90% or at least 95% still more preferably at least 99% and most preferably at least 100% of the proteinase activity of the proteinase of SEQ ID No: 1.

The enzymatically active fragments of the invention display at least 70%, preferably at least 80%, more preferably at least 85%, at least 90% or at least 95% still more preferably at least 99% and most preferably at least 100% of the proteinase activity of the proteinase of SEQ ID No: 1.

Suitable assays for analysing proteinase activity are known in the art and any such assay may be used for determining the proteinase activity of a particular polypeptide. Such assays can thus be used to determine proteinase activity of the proteinases, variant proteinases and enzymatically active fragments thereof of the present invention.

Preferred assays comprise assaying enzymatic cleavage of a substrate to a product detectable in a spectrophotometer, preferably the cleavage of Suc-Ala-Ala-Pro-Phe-pNA to 4-nitroalinine, which can be assayed by measuring the increase in absorbance at 410 nm ($\varepsilon$=8800 M$^{-1}$·cm$^{-1}$). It is within the competencies of the person of ordinary skill in the art to identify a suitable substrate and apparatus for yielding and detecting such absorbance. Preferably, absorbance is detected using a spectrophotometer or microplate reader.

Many spectrophotometers utilise cuvettes of 1000 µl volume. Many microplate readers utilise wells with volumes of 250 µl.

The skilled person will also readily be able to determine a suitable incubation temperature and assay time for their purposes. The skilled person would be aware that the temperature at which the assay is performed should be a temperature which does not lead to the inactivation of the proteinase of the invention, e.g. less than 40° C., preferably 25° C. Suitable assay times may be 30 seconds to 5 minutes, e.g. 2 minutes.

The skilled person will also be aware that the appropriate concentration of enzyme to include in the assay depends on the detectable range of the spectrophotometer used. The skilled person would be aware that a dilution step may be required prior to performing the assay to yield a concentration, and therefore a level of enzyme activity within the sample being assayed, that can be detected by the spectrophotometer in question. Activities of 10 to 50 mU/mL may be used, preferably 13 to 26 mU/mL, which for the Proteinase X of SEQ ID NO: 1 used in the present Examples equates to 0.2 to 0.4 µg/mL.

The skilled person will readily be able to formulate the remainder of the assay mixture for their intended purposes. The assay mixture may comprise a pH buffer as described elsewhere herein, preferably Tris-HCl, pH 8.

The assay mixture preferably comprises calcium in excess (e.g. ≥2 mM, preferably about 10 mM) such that low calcium conditions that could further inactivate the proteinase are avoided. NaCl may be present at low concentrations e.g. (≤15 mM) such that salt-induced thermolability of the proteinase is not induced. Again, the skilled person will readily be able to dilute the solution to provide the necessary concentrations of components, if required.

Other components may be added to the reaction mixture as desired, or may be present due to having been added at an earlier stage of the workflow and tolerated for the activity assay, e.g. DMSO.

A preferred assay for determining proteinase activity is Assay A (used in the Examples herein). Assay A comprises incubating in a 1000 µl or 250 µl cuvette:

13 or 26 mU/mL proteinase (equivalent to 0.2 or 0.4 µg of Proteinase X of SEQ ID NO: 1 used in the present Examples)
1 mM substrate Suc-Ala-Ala-Pro-Phe-pNA
≤15 mM NaCl (e.g. 12 mM NaCl or 4 mM NaCl)
0.1 mM Tris-HCl pH 8,
10 mM CaCl$_2$ and
1% DMSO (optional)

and assaying cleavage of the substrate to 4-nitroalinine by measuring the increase in absorbance at 410 nm ($\varepsilon$=8800 M$^{-1}$·cm$^{-1}$) over 2 minutes using a spectrophotometer (e.g. the Ultrospec 2000, Pharmacia Biotec, Sweden) at 25° C. or 37° C. One Unit is defined as the amount of enzyme that produces one µmol 4-nitroaniline per minute at a temperature less than 40° C., preferably 25° C. or 37°.

Alternative methods could be straightforwardly devised by the skilled person to measure proteinase activity.

Any suitable assay can be used to determine the relative activity of an enzymatically active fragment or variant or modified form of the proteinase of the invention as compared to the activity of the proteinase of SEQ ID NO: 1, and the skilled person would be well aware that the same technique and conditions should be used for assessing the activity of the fragment or variant or modified form as is used for the assessing the activity of the proteinase of SEQ ID NO: 1. Preferably the assay used is Assay A, above.

According to the above-preferred Assay A, proteinase X has a specific activity of about 65 U/mg (65.2 U/mg). Preferably, the variant, enzymatic fragments and modified forms of the invention have a specific activity of 40 to 100 U/mg, more preferably 50 to 80 U/mg, more preferably 60 to 70 U/mg, more preferably 62.5 to 67.5 U/mg, preferably about 65 U/mg or 65.2 U/mg as determined by Assay A described above. Preferably, the variant proteinases and enzymatic fragments of the invention have the same specific activity as Proteinase X of SEQ ID NO: 1 as determined by Assay A described above.

The compositions and samples of the invention preferably comprise ≤80 µM free calcium. The term "free calcium" as used herein refers exclusively to calcium ions that are free, i.e. unbound, within the compositions and samples of the invention, i.e. calcium ions that are not bound to any proteins or other components present in the compositions and sample of the invention, i.e. liberated calcium. Reference throughout to concentrations of calcium in the compositions and solutions of the invention is a reference to the concentration of free calcium.

Proteinase X (SEQ ID NO: 1) comprises a calcium-binding site formed by residues Asp11, Asp14, Gln15, Asp21 and Asn23. A $Ca^{2+}$ ion is coordinated to the carboxyl oxygen atoms of the side chains of Asp11, Asp14 and Asp21, the amide oxygen atom of Gln15 and the carbonyl oxygen atoms of Asp11 and Asn23. This bound calcium ion is required for correct protein folding. Thus, the proteinases of use in the present invention naturally comprise this bound calcium ion. The bound calcium ion will also be present if a proteinase of use in the invention is produced recombinantly. Any environment used to produce the proteinase will necessarily include calcium, meaning that the bound ion will be present in folded proteinase structure. Such bound calcium ions are not "free calcium" as the term is used herein.

The person of ordinary skill in the art preparing a composition or sample of the invention could straightforwardly ensure that the required calcium concentration was achieved merely by selecting appropriate solutes and solvents for inclusion in the solution or sample. It is within the competencies of the person of ordinary skill in the art to remove free calcium from a solution by dialysis against a large volume of calcium-free buffer, for instance dialysis against 500 to 10000, preferably 5000 volumes of a calcium-free buffer. Suitable buffers would be apparent to one of ordinary skill in the art and are preferably buffers as described elsewhere herein, for instance 10 mM Tris-HCl, pH 7 to 9. Preferably, said buffer further comprises glycerol.

Concentrations of free calcium in any given solution or sample can also be readily determined by the person of ordinary skill in the art. Standard methods for determining calcium are well known in the art and include, for instance, titration with a standardized solution of EDTA.

Bound calcium ions can be removed from proteinases by the application of a strong calcium-chelating agent, e.g. EDTA. It is however undesirable to expose many biological molecules of interest to EDTA. In addition, EDTA binds $Mg^{2+}$ ions, which are required for many nucleic acid related enzymes (e.g. polymerases, nucleases). Such enzymes are employed in molecular biology techniques subsequent to sample preparation using a proteinase—the presence of EDTA is particularly problematic in this context. EDTA introduces uncertainty regarding the free $Mg^{2+}$ concentration in subsequent downstream steps, which is not desirable: $Mg^{2+}$ is required for enzyme function but too much causes RNA degradation. In any method of digesting polypeptides, the omission of reagents is desirable since their inclusion and subsequent removal increases the cost, time and work flow of the process.

The present inventors have made the surprising finding that the mere absence of free calcium is sufficient to induce thermolability in the proteinases of the present invention. The present inventors have for the first time determined that, surprisingly, thermolability of Proteinase X is induced when the proteinase is present in an environment with a low concentration of free calcium ions. The inventors have determined that it is not necessary to remove calcium ions that may be bound to the proteinase and contribute to its stability and structure, e.g. by using EDTA. Rather, merely providing a low concentration of free calcium ions is surprisingly sufficient to induce thermolabile properties onto the enzyme. Such inducible properties are unexpected and, as demonstrated in the Examples, are not observed with the gold-standard proteinase used in molecular biology applications; Proteinase K.

Accordingly, preferably the proteinases and enzymatically active fragments thereof of the invention comprise calcium ions bound thereto. In other words, preferably the compositions and samples of the invention comprise the proteinases and enzymatically active fragments thereof in their native, calcium-bound state. In this scenario, calcium can be considered a "cofactor" for the protein, and the proteinases are thus in their "holoenzyme form" in the compositions and samples of the invention. A holoenzyme is a biochemically active enzyme formed by the combination of an apoenzyme with its cofactors (in this case calcium).

Thus, preferably, the compositions and samples of the present invention are essentially free of, preferably do not comprise EDTA, more preferably any calcium-chelating agent. Preferably, the proteinases and enzymatically active fragments thereof present in the solutions and samples of the present invention have not at any point been exposed to EDTA, more preferably any calcium-chelating agent.

Alternatively viewed, the present invention provides a composition comprising a proteinase or an enzymatically active fragment thereof, said proteinase comprising the amino acid sequence of SEQ ID NO: 1 or comprising an amino acid sequence which is at least about 70% identical to SEQ ID NO: 1, wherein
i) the concentration of calcium in said composition is ≤about 80 µM and said composition is essentially free of EDTA, preferably essentially free of calcium chelating agents; or
ii) the concentration of monovalent salt in said composition is ≥about 20 mM.

And alternatively viewed the present invention provides a sample comprising one or more polypeptides and a proteinase or an enzymatically active fragment thereof, said proteinase comprising the amino acid sequence of SEQ ID NO: 1 or comprising an amino acid sequence which is at least about 70% identical to SEQ ID NO: 1, wherein
i) the concentration of calcium in said sample is ≤about 80 µM and said sample is essentially free of EDTA, preferably essentially free of calcium chelating agents; or
ii) the concentration of monovalent salt in said sample is ≥about 20 mM.

And alternatively viewed the present invention provides a composition comprising a proteinase or an enzymatically active fragment thereof, said proteinase comprising the amino acid sequence of SEQ ID NO: 1 or comprising an amino acid sequence which is at least about 70% identical to SEQ ID NO: 1, wherein i) the concentration of calcium in said composition is ≤about 80 μM and said composition is essentially free of EDTA, preferably essentially free of calcium chelating agents; or
ii) the concentration of monovalent salt in said composition is ≥about 20 mM, and wherein said proteinase or enzymatically active fragment thereof further comprises a further peptide sequence that is N-terminal and/or a further peptide sequence that is C-terminal to the amino acid sequence of SEQ ID NO: 1 or the amino acid sequence which is at least about 70% identical to SEQ ID NO:1.

The preferred and optional features and embodiments described anywhere else herein apply mutatis mutandis to the "alternatively viewed" aspects of the invention. In particular, the concentrations of "free calcium" disclosed elsewhere herein are the preferred concentrations of calcium (not defined as "free calcium") in the alternatively viewed compositions and samples of the invention that are essentially free of EDTA, more preferably essentially free of any calcium-chelating agent. The same applies to the methods of the invention below that do refer to a concentration of "calcium" rather than "free calcium" and which specify that the sample or composition of the method is essentially free of EDTA.

Preferably, the compositions and samples of all aspects of the present invention are essentially free of EDTA and EGTA, more preferably essentially free of calcium-chelating agents capable of removing bound calcium from the proteinase X structure, more preferably essentially free of calcium-chelating agents.

By "essentially free of", for instance, EDTA or free calcium, is meant that the composition and samples are in essence free of EDTA or free calcium but it does not mean that there is a strict requirement for them to lack EDTA or free calcium entirely. There is potential for a de minimis level of EDTA or free calcium even after steps have been taken to prevent the presence of EDTA or free calcium, for instance due to the existence of small amounts of EDTA or free calcium in a commercial product or stock solution used to prepare the compositions or samples of the invention. While a detailed inspection may reveal that some EDTA is present, it is present in such small quantities that for the purposes intended it can be considered absent, i.e. it is not present at a level that substantially alters the level of free calcium, or the extent of calcium binding to the proteinases of the invention, as compared to such levels or extent that would occur in the absence of the EDTA.

By "essentially free of" in the context of a calcium chelating agent is meant that the ratio of the concentration of Proteinase X to the concentration of calcium chelating agent, e.g. EDTA or EGTA, in the sample is at least 10:1, more preferably at least 100:1, more preferably at least 1000:1. If the sample contains more than one calcium chelating agent, then these ratios are the ratios of the concentration of Proteinase X to the total concentration of calcium chelating agents in the sample.

While a detailed inspection may reveal that some free calcium is present, it is present in such small quantities that for the purposes intended it can be considered absent, i.e. it is not present at a level that substantially alters the thermolability of the proteinases of the invention, as compared to such levels or extent that would occur in the absence of the free calcium.

Preferably, the compositions and samples of the invention are entirely free of EDTA, more preferably free of calcium-chelating agents capable of removing bound calcium from the proteinase X structure, more preferably free of calcium-chelating agents.

Preferably, the compositions and samples of the invention are entirely free of free calcium, i.e. do not comprise free calcium.

The concentration of free calcium in the compositions and samples of the present invention is preferably ≤about 80 μM, preferably ≤about 65 μM, more preferably ≤about 40 μM, more preferably ≤about 35 μM, ≤about 32 μM or ≤about 30 μM, more preferably ≤about 25 μM or ≤about 20 μM, more preferably ≤about 16 μM or ≤about 15 μM, more preferably ≤about 10 μM, more preferably ≤about 8 μM or ≤about 5 μM, more preferably ≤about 2.5 μM. The term "≤about X" is equivalent to "from 0 to X mM". Preferably, the compositions and samples of the present invention do not comprise free calcium.

Preferably, the concentration of free calcium in the compositions and samples of the present invention is at least about 1 μM. Thus, the concentration of free calcium in the compositions and samples of the present invention is preferably from about 1 to about 80 μM, more preferably from about 1 to about 65 μM, preferably from about 1 to about 40 μM, preferably from about 1 to about 35 μM, preferably from about 1 to about 32 μM, preferably from about 1 to about 30 μM, preferably from about 1 to about 25 μM, preferably from about 1 to about 20 μM, preferably from about 1 to about 16 μM, preferably from about 1 to about 15 μM, preferably from about 1 to about 10 μM, preferably from about 1 to about 8 μM, preferably from about 1 to about 5 μM, preferably from about 1 to about 2.5 μM.

Preferably, the concentration of free calcium in the compositions and samples of the present invention is at least about 2 μM. Thus, the concentration of free calcium in the compositions and samples of the present invention is preferably from about 2 to about 80 μM, more preferably from about 2 to about 65 μM, preferably from about 2 to about 40 μM, preferably from about 2 to about 35 μM, preferably from about 2 to about 32 μM, preferably from about 2 to about 30 μM, preferably from about 2 to about 25 μM, preferably from about 2 to about 20 μM, preferably from about 2 to about 16 μM, preferably from about 2 to about 15 μM, preferably from about 2 to about 10 μM, preferably from about 2 to about 8 μM, preferably from about 2 to about 5 μM, preferably from about 2 to about 2.5 μM.

Preferably, the compositions and samples of the invention are essentially free of free calcium, more preferably do not comprise free calcium. The term "essentially free" is as defined elsewhere herein.

Particularly preferably, the concentration of free calcium in the compositions and samples of the present invention is ≤about 35 μM, ≤about 32 μM, preferably ≤about 16 μM, preferably ≤about 10 μM. Particularly preferably, the concentration of free calcium in the compositions and samples of the present invention is at least about 1 μM, preferably at least about 2 μM. Thus, particularly preferably, the concentration of free calcium in the compositions and samples of the present invention is from about 1 to about 35 μM, preferably from about 1 to about 32 μM, preferably from about 2 to about 35 μM, preferably from about 2 to about 32 μM, preferably from about 1 to about 16 μM, preferably from about 2 to about 16 μM, preferably from about 1 to about 10 μM, preferably from about 2 to about 10 μM.

As mentioned above, preferably the compositions and samples of the invention preferably comprise such concentrations of free calcium and are essentially free of EDTA, preferably essentially free of calcium chelating agents.

Preferably, the concentration of the proteinase or enzymatically active fragment thereof in the compositions of the invention is from 0.1 mg/ml to 20 mg/ml, more preferably 0.5 mg/ml to 10 mg/ml, most preferably 2 mg/ml to 5 mg/ml.

Using the above preferred Assay A, the present inventors have determined that proteinase X has a specific activity of about 65 U/mg. Preferably, the activity of the proteinase or enzymatically active fragment thereof in the compositions of the invention is from 0.0015 U/µl to 0.30 U/µl, more preferably 0.008 U/µl to 0.15 U/µl, most preferably about 0.03 U/µl to 0.08 U/µl when determined using Assay A, above.

Preferably, the concentration of the proteinase or enzymatically active fragment thereof in the samples of the invention is from 0.001 mg/ml to 5 mg/ml, more preferably 0.05 mg/ml to 0.5 mg/ml, most preferably 0.015 mg/ml to 0.1 mg/ml.

Preferably, the activity of the proteinase or enzymatically active fragment thereof in the samples of the invention is from 0.07 U/ml to 325 U/ml, more preferably 3.25 U/ml to 32.5 U/ml, most preferably 1.0 U/µl to 6.5 U/ml, when determined using Assay A, above.

Optionally, the composition or sample of the present invention comprises one or more further functional proteins selected from the group consisting of antibodies, single stranded DNA binding proteins (SSBs) and enzymes.

Preferably, said further enzyme is selected from the group consisting of a nuclease (preferably a deoxyribonuclease, an exonuclease, a Bal 31 nuclease, a ribonuclease, a mung bean nuclease or an S1 nuclease), a polymerase (preferably a DNA polymerase or an RNA polymerase), a reverse transcriptase, a transposase, a ligase, (preferably a DNA ligase or an RNA ligase), a methylase, a polynucleotide adenylyltransferase, a topisomerase, a guanylyl transferase, a phosphatase (preferably an alkaline phosphatase, preferably a thermolabile alkaline phosphatase, more preferably shrimp alkaline phosphatase), a kinase, a helicase, a restriction enzyme and a glycosylase. The composition or sample preferably comprises combinations of such further enzymes.

Preferably, the composition or sample comprises a DNA polymerase or a reverse transcriptase. If the solution or sample comprises cells or cellular material, then they preferably comprise such further enzymes that are exogenous enzymes, i.e. not expressed by the cells within the sample or the cells from which the cellular material in the sample is derived. In other words, the further enzymes are applied to the sample rather than being provided by the cells or cellular material in the sample. In these embodiments, the additional presence of endogenously produced enzymes is not precluded.

The compositions and samples of the present invention preferably comprise a monovalent salt, preferably a monovalent inorganic salt. The terms "salt" and "monovalent salt" are used synonymously throughout. A monovalent salt is a salt comprising monovalent counterions. A divalent salt is a salt in which at least one of the counter ions is divalent. E.g. $MgCl_2$. An inorganic salt is a salt in which neither of the counter ions comprises carbon. Preferably, the salt is a sodium salt or a potassium salt, more preferably a sodium salt. Preferably the salt is sodium chloride (NaCl) or potassium chloride (KCl), most preferably sodium chloride.

Alternatively viewed, the compositions and samples of the present invention preferably comprise monovalent counterions. Preferably the compositions and samples of the invention comprise monovalent cations and preferably also monovalent anions. Preferably, the monovalent ions are inorganic. Preferably, the cations are sodium ions or potassium ions, preferably sodium ions. Preferably, the compositions and samples comprise sodium and chloride ions or potassium and chloride ions, most preferably sodium and chloride ions. The preferred concentrations of monovalent salts disclosed herein are, inherently, the preferred concentrations of monovalent counterions, and vice versa.

As shown in the Examples, the present inventors have demonstrated for the first time that increasing the concentration of monovalent salt induces thermolability of Proteinase X, whereas increasing monovalent salt concentrations stabilise Proteinase K to heat inactivation. This result is particularly surprising. The proteinase X of SEQ ID NO: 1 is obtained from a salt water organism, and so would ordinarily be expected to tolerate high salt conditions. In contrast, Proteinase K is obtained from a non-marine source, the fungus Engyodontium album (formerly Tritirachium album) and would not be expected to be stabilised by high salt conditions.

In the samples and compositions of the invention comprising monovalent salt, preferably the compositions and samples have a pH of 6.5 to 9.5, preferably 6.8 to 9.2, more preferably 7 to 9, more preferably 7.5 to 8.5, more preferably about 8.0.

Preferably, the concentration of monovalent salt in the compositions and samples of the present invention is ≥about 20 mM, preferably ≥about 25 mM, more preferably ≥about 30 mM, more preferably ≥about 40 mM, more preferably ≥about 50 mM, more preferably ≥about 75 mM, more preferably ≥about 100 mM, more preferably ≥about 125 mM, more preferably ≥about 150 mM, more preferably ≥about 175 mM. Optionally, the concentration of monovalent salt in the composition and samples of the present invention is ≥about 200 mM, ≥about 250 mM, ≥about 300 mM, ≥about 400 mM, or ≥500 mM.

Preferably, the concentration of monovalent salt in the compositions and samples of the present invention is ≤about 1 M, preferably ≤about 500 mM, preferably ≤about 350 mM. The concentration of monovalent salt in the compositions and samples of the present invention is preferably from about 20 mM to about 1 M, preferably from about 20 to about 500 mM, preferably from about 20 to about 400 mM, preferably from about 20 to about 350 mM, preferably from about 30 to about 350 mM, preferably from about 40 to about 350 mM, preferably from about 50 to about 350 mM, preferably from about 75 to about 350 mM, preferably from about 100 to about 350 mM, preferably from about 125 to about 350 mM, preferably from about 150 to about 350 mM, preferably from about 175 to about 350 mM. Optionally, the concentration of monovalent salt in the composition and samples of the present invention is from about 200 to about 350 mM, or from about 300 to about 350 mM.

Preferably the concentration of monovalent salt in the compositions and samples of the present invention is ≤about 500 mM, preferably ≤about 400 mM, preferably ≤about 300 mM, preferably ≤about 250 mM, preferably ≤about 200 mM, preferably ≤about 175 mM, preferably ≤about 150 mM.

Preferably, the concentration of monovalent salt in the compositions and samples of the present invention is from about 20 to about 300 mM, preferably from about 30 to about 300 mM, preferably from about 40 to about 300 mM, preferably from about 50 to about 300 mM, preferably from about 75 to about 300 mM, preferably from about 100 to about 300 mM, preferably from about 125 to about 300 mM, preferably from about 150 to about 300 mM, preferably from about 175 to about 300 mM. Optionally, the concentration of monovalent salt in the composition and samples of the present invention is from about 200 to about 300 mM, Preferably, the concentration of monovalent salt in the compositions and samples of the present invention is from about 20 to about 250 mM, preferably from about 30 to about 250 mM, preferably from about 40 to about 250 mM, preferably from about 50 to about 250 mM, preferably from about 75 to about 250 mM, preferably from about 100 to about 250 mM, preferably from about 125 to about 250 mM, preferably from about 150 to about 250 mM, preferably from about 175 to about 250 mM. Optionally, the concentration of monovalent salt in the composition and samples of the present invention is from about 200 to about 250 mM, Preferably, the concentration of monovalent salt in the compositions and samples of the present invention is from about 20 to about 200 mM, preferably from about 30 to about 200 mM, preferably from about 40 to about 200 mM, preferably from about 50 to about 200 mM, preferably from about 75 to about 200 mM, preferably from about 100 to about 200 mM, preferably from about 125 to about 200 mM, preferably from about 150 to about 200 mM, preferably from about 175 to about 200 mM.

Preferably, the concentration of monovalent salt in the compositions and samples of the present invention is from about 20 to about 175 mM, preferably from about 30 to about 175 mM, preferably from about 40 to about 175 mM, preferably from about 50 to about 175 mM, preferably from about 75 to about 175 mM, preferably from about 100 to about 175 mM, preferably from about 125 to about 175 mM, preferably from about 150 to about 175 mM.

Preferably, the concentration of monovalent salt in the compositions and samples of the present invention is from about 20 to about 150 mM, preferably from about 30 to about 150 mM, preferably from about 40 to about 150 mM, preferably from about 50 to about 150 mM, preferably from about 75 to about 150 mM, preferably from about 100 to about 150 mM, preferably from about 125 to about 150 mM.

Particularly preferably, the concentration of monovalent salt in the compositions and samples of the present invention is from about 20 to about 175 mM, preferably from about 20 to about 150 mM, preferably from about 50 to about 150 mM. Particularly preferably, the concentration of monovalent salt in the compositions and samples of the present invention is from about 30 to about 175 mM, preferably from about 30 to about 150 mM, preferably from about 30 to about 150 mM. Particularly preferably, the concentration of monovalent salt in the compositions and samples of the present invention is from about 40 to about 175 mM, preferably from about 40 to about 150 mM, preferably from about 40 to about 150 mM.

Preferably, the compositions and samples of the invention comprise a concentration of free calcium and a concentration of monovalent salt as defined anywhere herein. An express disclosure is hereby made of the combination of any calcium concentration value or range disclosed herein with any monovalent salt concentration value or range disclosed herein in respect of all aspects and embodiments of the present invention. Preferably, the monovalent salt is NaCl or KCl, preferably NaCl.

Preferred combinations of maximum free calcium concentrations and minimum monovalent salt concentrations are shown below:

| # | Max. free $Ca^{2+}$ conc. | In combination with Min. salt conc. |
|---|---|---|
| 1 | about 80 μM | about 20 mM |
| 2 | about 80 μM | about 25 mM |
| 3 | about 80 μM | about 50 mM |
| 4 | about 80 μM | about 75 mM |
| 5 | about 80 μM | about 100 mM |
| 6 | about 80 μM | about 125 mM |
| 7 | about 80 μM | about 150 mM |
| 8 | about 80 μM | about 200 mM |
| 9 | about 80 μM | about 300 mM |
| 10 | about 80 μM | about 400 mM |
| 11 | about 80 μM | about 500 mM |
| 12 | about 65 μM | about 20 mM |
| 13 | about 65 μM | about 25 mM |
| 14 | about 65 μM | about 50 mM |
| 15 | about 65 μM | about 75 mM |
| 16 | about 65 μM | about 100 mM |
| 17 | about 65 μM | about 125 mM |
| 18 | about 65 μM | about 150 mM |
| 19 | about 65 μM | about 200 mM |
| 20 | about 65 μM | about 300 mM |
| 21 | about 65 μM | about 400 mM |
| 22 | about 65 μM | about 500 mM |
| 23 | about 40 μM | about 20 mM |
| 24 | about 40 μM | about 25 mM |
| 25 | about 40 μM | about 50 mM |
| 26 | about 40 μM | about 75 mM |
| 27 | about 40 μM | about 100 mM |
| 28 | about 40 μM | about 125 mM |
| 29 | about 40 μM | about 150 mM |
| 30 | about 40 μM | about 200 mM |
| 31 | about 40 μM | about 300 mM |
| 32 | about 40 μM | about 400 mM |
| 33 | about 40 μM | about 500 mM |
| 34 | about 35 μM | about 20 mM |
| 35 | about 35 μM | about 25 mM |
| 36 | about 35 μM | about 50 mM |
| 37 | about 35 μM | about 75 mM |
| 38 | about 35 μM | about 100 mM |
| 39 | about 35 μM | about 125 mM |
| 40 | about 35 μM | about 150 mM |
| 41 | about 35 μM | about 200 mM |
| 42 | about 35 μM | about 300 mM |
| 43 | about 35 μM | about 400 mM |
| 44 | about 35 μM | about 500 mM |
| 45 | about 32 μM | about 20 mM |
| 46 | about 32 μM | about 25 mM |
| 47 | about 32 μM | about 50 mM |
| 48 | about 32 μM | about 75 mM |
| 49 | about 32 μM | about 100 mM |
| 50 | about 32 μM | about 125 mM |
| 51 | about 32 μM | about 150 mM |
| 52 | about 32 μM | about 200 mM |
| 53 | about 32 μM | about 300 mM |
| 54 | about 32 μM | about 400 mM |
| 55 | about 32 μM | about 500 mM |
| 56 | about 30 μM | about 20 mM |
| 57 | about 30 μM | about 25 mM |
| 58 | about 30 μM | about 50 mM |
| 59 | about 30 μM | about 75 mM |
| 60 | about 30 μM | about 100 mM |
| 61 | about 30 μM | about 125 mM |
| 62 | about 30 μM | about 150 mM |
| 63 | about 30 μM | about 200 mM |
| 64 | about 30 μM | about 300 mM |
| 65 | about 30 μM | about 400 mM |
| 66 | about 30 μM | about 500 mM |
| 67 | about 25 μM | about 20 mM |
| 68 | about 25 μM | about 25 mM |
| 69 | about 25 μM | about 50 mM |
| 70 | about 25 μM | about 75 mM |
| 71 | about 25 μM | about 100 mM |
| 72 | about 25 μM | about 125 mM |

| # | Max. free $Ca^{2+}$ conc. | In combination with Min. salt conc. |
|---|---|---|
| 73 | about 25 µM | about 150 mM |
| 74 | about 25 µM | about 200 mM |
| 75 | about 25 µM | about 300 mM |
| 76 | about 25 µM | about 400 mM |
| 77 | about 25 µM | about 500 mM |
| 78 | about 20 µM | about 20 mM |
| 79 | about 20 µM | about 25 mM |
| 80 | about 20 µM | about 50 mM |
| 81 | about 20 µM | about 75 mM |
| 82 | about 20 µM | about 100 mM |
| 83 | about 20 µM | about 125 mM |
| 84 | about 20 µM | about 150 mM |
| 85 | about 20 µM | about 200 mM |
| 86 | about 20 µM | about 300 mM |
| 87 | about 20 µM | about 400 mM |
| 88 | about 20 µM | about 500 mM |
| 89 | about 16 µM | about 20 mM |
| 90 | about 16 µM | about 25 mM |
| 91 | about 16 µM | about 50 mM |
| 92 | about 16 µM | about 75 mM |
| 93 | about 16 µM | about 100 mM |
| 94 | about 16 µM | about 125 mM |
| 95 | about 16 µM | about 150 mM |
| 96 | about 16 µM | about 200 mM |
| 97 | about 16 µM | about 300 mM |
| 98 | about 16 µM | about 400 mM |
| 99 | about 16 µM | about 500 mM |
| 100 | about 15 µM | about 20 mM |
| 101 | about 15 µM | about 25 mM |
| 102 | about 15 µM | about 50 mM |
| 103 | about 15 µM | about 75 mM |
| 104 | about 15 µM | about 100 mM |
| 105 | about 15 µM | about 125 mM |
| 106 | about 15 µM | about 150 mM |
| 107 | about 15 µM | about 200 mM |
| 108 | about 15 µM | about 300 mM |
| 109 | about 15 µM | about 400 mM |
| 110 | about 15 µM | about 500 mM |
| 111 | about 10 µM | about 20 mM |
| 112 | about 10 µM | about 25 mM |
| 113 | about 10 µM | about 50 mM |
| 114 | about 10 µM | about 75 mM |
| 115 | about 10 µM | about 100 mM |
| 116 | about 10 µM | about 125 mM |
| 117 | about 10 µM | about 150 mM |
| 118 | about 10 µM | about 200 mM |
| 119 | about 10 µM | about 300 mM |
| 120 | about 10 µM | about 400 mM |
| 121 | about 10 µM | about 500 mM |
| 122 | about 8 µM | about 20 mM |
| 123 | about 8 µM | about 25 mM |
| 124 | about 8 µM | about 50 mM |
| 125 | about 8 µM | about 75 mM |
| 126 | about 8 µM | about 100 mM |
| 127 | about 8 µM | about 125 mM |
| 128 | about 8 µM | about 150 mM |
| 129 | about 8 µM | about 200 mM |
| 130 | about 8 µM | about 300 mM |
| 131 | about 8 µM | about 400 mM |
| 132 | about 8 µM | about 500 mM |
| 133 | about 5 µM | about 20 mM |
| 134 | about 5 µM | about 25 mM |
| 135 | about 5 µM | about 50 mM |
| 136 | about 5 µM | about 75 mM |
| 137 | about 5 µM | about 100 mM |
| 138 | about 5 µM | about 125 mM |
| 139 | about 5 µM | about 150 mM |
| 140 | about 5 µM | about 200 mM |
| 141 | about 5 µM | about 300 mM |
| 142 | about 5 µM | about 400 mM |
| 143 | about 5 µM | about 500 mM |
| 144 | about 2.5 µM | about 20 mM |
| 145 | about 2.5 µM | about 25 mM |
| 146 | about 2.5 µM | about 50 mM |
| 147 | about 2.5 µM | about 75 mM |
| 148 | about 2.5 µM | about 100 mM |
| 149 | about 2.5 µM | about 125 mM |
| 150 | about 2.5 µM | about 150 mM |
| 151 | about 2.5 µM | about 200 mM |
| 152 | about 2.5 µM | about 300 mM |
| 153 | about 2.5 µM | about 400 mM |
| 154 | about 2.5 µM | about 500 mM |

Furthermore, preferably the concentration of free calcium in the compositions and samples of the present invention is at least about 1 µM, more preferably at least about 2 µM. Furthermore, preferably the concentration of monovalent salt in the composition and samples of the present invention is no more than about 500 mM, preferably no more than about 400 mM, preferably no more than about 350 mM, preferably no more than 300 mM, preferably no more than about 250 mM, preferably no more than about 200 mM, preferably no more than about 175 mM, preferably no more than about 150 mM.

Preferred combinations of maximum free calcium concentrations and monovalent salt concentrations are shown below:

| # | Max. free $Ca^{2+}$ conc. | Salt conc. |
|---|---|---|
| 155 | about 80 µM | about 20 to about 175 mM |
| 156 | about 80 µM | about 20 to about 150 mM |
| 157 | about 80 µM | about 50 to about 175 mM |
| 158 | about 80 µM | About 50 to about 150 mM |
| 159 | about 65 µM | about 20 to about 175 mM |
| 160 | about 65 µM | about 20 to about 150 mM |
| 161 | about 65 µM | about 50 to about 175 mM |
| 162 | about 65 µM | About 50 to about 150 mM |
| 163 | about 40 µM | about 20 to about 175 mM |
| 164 | about 40 µM | about 20 to about 150 mM |
| 165 | about 40 µM | about 50 to about 175 mM |
| 166 | about 40 µM | About 50 to about 150 mM |
| 167 | about 35 µM | about 20 to about 175 mM |
| 168 | about 35 µM | about 20 to about 150 mM |
| 169 | about 35 µM | about 50 to about 175 mM |
| 170 | about 35 µM | About 50 to about 150 mM |
| 171 | about 32 µM | about 20 to about 175 mM |
| 172 | about 32 µM | about 20 to about 150 mM |
| 173 | about 32 µM | about 50 to about 175 mM |
| 174 | about 32 µM | About 50 to about 150 mM |
| 175 | about 30 µM | about 20 to about 175 mM |
| 176 | about 30 µM | about 20 to about 150 mM |

Preferred combinations of free calcium concentrations and monovalent salt concentrations are shown below:

| # | Max. free $Ca^{2+}$ conc. | Salt conc. |
|---|---|---|
| 177 | about 30 μM | about 50 to about 175 mM |
| 178 | about 30 μM | About 50 to about 150 mM |
| 179 | about 25 μM | about 20 to about 175 mM |
| 180 | about 25 μM | about 20 to about 150 mM |
| 181 | about 25 μM | about 50 to about 175 mM |
| 182 | about 25 μM | about 50 to about 150 mM |
| 183 | about 20 μM | about 20 to about 175 mM |
| 184 | about 20 μM | about 20 to about 150 mM |
| 185 | about 20 μM | about 50 to about 175 mM |
| 186 | about 20 μM | About 50 to about 150 mM |
| 187 | about 16 μM | about 20 to about 175 mM |
| 188 | about 16 μM | about 20 to about 150 mM |
| 189 | about 16 μM | about 50 to about 175 mM |
| 190 | about 16 μM | About 50 to about 150 mM |
| 191 | about 15 μM | about 20 to about 175 mM |
| 192 | about 15 μM | about 20 to about 150 mM |
| 193 | about 15 μM | about 50 to about 175 mM |
| 194 | about 15 μM | About 50 to about 150 mM |
| 195 | about 10 μM | about 20 to about 175 mM |
| 196 | about 10 μM | about 20 to about 150 mM |
| 197 | about 10 μM | about 50 to about 175 mM |
| 198 | about 10 μM | About 50 to about 150 mM |
| 199 | about 8 μM | about 20 to about 175 mM |
| 200 | about 8 μM | about 20 to about 150 mM |
| 201 | about 8 μM | about 50 to about 175 mM |
| 202 | about 8 μM | About 50 to about 150 mM |
| 203 | about 5 μM | about 20 to about 175 mM |
| 204 | about 5 μM | about 20 to about 150 mM |
| 205 | about 5 μM | about 50 to about 175 mM |
| 206 | about 5 μM | About 50 to about 150 mM |
| 207 | about 2.5 μM | about 20 to about 175 mM |
| 208 | about 2.5 μM | about 20 to about 150 mM |
| 209 | about 2.5 μM | about 50 to about 175 mM |
| 210 | about 2.5 μM | About 50 to about 150 mM |
| 211 | about 1 to about 80 μM | about 20 to about 175 mM |
| 212 | about 1 to about 80 μM | about 20 to about 150 mM |
| 213 | about 1 to about 80 μM | about 50 to about 175 mM |
| 214 | about 1 to about 80 μM | About 50 to about 150 mM |
| 215 | about 1 to about 65 μM | about 20 to about 175 mM |
| 216 | about 1 to about 65 μM | about 20 to about 150 mM |
| 217 | about 1 to about 65 μM | about 50 to about 175 mM |
| 218 | about 1 to about 65 μM | About 50 to about 150 mM |
| 219 | about 1 to about 40 μM | about 20 to about 175 mM |
| 220 | about 1 to about 40 μM | about 20 to about 150 mM |
| 221 | about 1 to about 40 μM | about 50 to about 175 mM |
| 222 | about 1 to about 40 μM | About 50 to about 150 mM |
| 223 | about 1 to about 35 μM | about 20 to about 175 mM |
| 224 | about 1 to about 35 μM | about 20 to about 150 mM |
| 225 | about 1 to about 35 μM | about 50 to about 175 mM |
| 226 | about 1 to about 35 μM | About 50 to about 150 mM |
| 227 | about 1 to about 32 μM | about 20 to about 175 mM |
| 228 | about 1 to about 32 μM | about 20 to about 150 mM |
| 229 | about 1 to about 32 μM | about 50 to about 175 mM |
| 230 | about 1 to about 32 μM | About 50 to about 150 mM |
| 231 | about 1 to about 30 μM | about 20 to about 175 mM |
| 232 | about 1 to about 30 μM | about 20 to about 150 mM |
| 233 | about 1 to about 30 μM | about 50 to about 175 mM |
| 234 | about 1 to about 30 μM | About 50 to about 150 mM |
| 235 | about 1 to about 25 μM | about 20 to about 175 mM |
| 236 | about 1 to about 25 μM | about 20 to about 150 mM |
| 237 | about 1 to about 25 μM | about 50 to about 175 mM |
| 238 | about 1 to about 25 μM | about 50 to about 150 mM |
| 239 | about 1 to about 20 μM | about 20 to about 175 mM |
| 240 | about 1 to about 20 μM | about 20 to about 150 mM |
| 241 | about 1 to about 20 μM | about 50 to about 175 mM |
| 242 | about 1 to about 20 μM | About 50 to about 150 mM |
| 243 | about 1 to about 16 μM | about 20 to about 175 mM |
| 244 | about 1 to about 16 μM | about 20 to about 150 mM |
| 245 | about 1 to about 16 μM | about 50 to about 175 mM |
| 246 | about 1 to about 16 μM | About 50 to about 150 mM |
| 247 | about 1 to about 15 μM | about 20 to about 175 mM |

| # | Max. free $Ca^{2+}$ conc. | Salt conc. |
|---|---|---|
| 248 | about 1 to about 15 μM | about 20 to about 150 mM |
| 249 | about 1 to about 15 μM | about 50 to about 175 mM |
| 250 | about 1 to about 15 μM | About 50 to about 150 mM |
| 251 | about 1 to about 10 μM | about 20 to about 175 mM |
| 252 | about 1 to about 10 μM | about 20 to about 150 mM |
| 253 | about 1 to about 10 μM | about 50 to about 175 mM |
| 254 | about 1 to about 10 μM | About 50 to about 150 mM |
| 255 | about 1 to about 8 μM | about 20 to about 175 mM |
| 256 | about 1 to about 8 μM | about 20 to about 150 mM |
| 257 | about 1 to about 8 μM | about 50 to about 175 mM |
| 258 | about 1 to about 8 μM | About 50 to about 150 mM |
| 259 | about 1 to about 5 μM | about 20 to about 175 mM |
| 260 | about 1 to about 5 μM | about 20 to about 150 mM |
| 261 | about 1 to about 5 μM | about 50 to about 175 mM |
| 262 | about 1 to about 5 μM | About 50 to about 150 mM |
| 263 | about 1 to about 2.5 μM | about 20 to about 175 mM |
| 264 | about 1 to about 2.5 μM | about 20 to about 150 mM |
| 265 | about 1 to about 2.5 μM | about 50 to about 175 mM |
| 266 | about 1 to about 2.5 μM | About 50 to about 150 mM |

Preferred combinations of free calcium concentrations and monovalent salt concentrations are shown below:

| # | Max. free $Ca^{2+}$ conc. | Salt conc. |
|---|---|---|
| 267 | about 2 to about 80 μM | about 20 to about 175 mM |
| 268 | about 2 to about 80 μM | about 20 to about 150 mM |
| 269 | about 2 to about 80 μM | about 50 to about 175 mM |
| 270 | about 2 to about 80 μM | About 50 to about 150 mM |
| 271 | about 2 to about 65 μM | about 20 to about 175 mM |
| 272 | about 2 to about 65 μM | about 20 to about 150 mM |
| 273 | about 2 to about 65 μM | about 50 to about 175 mM |
| 274 | about 2 to about 65 μM | About 50 to about 150 mM |
| 275 | about 2 to about 40 μM | about 20 to about 175 mM |
| 276 | about 2 to about 40 μM | about 20 to about 150 mM |
| 277 | about 2 to about 40 μM | about 50 to about 175 mM |
| 278 | about 2 to about 40 μM | About 50 to about 150 mM |
| 279 | about 2 to about 35 μM | about 20 to about 175 mM |
| 280 | about 2 to about 35 μM | about 20 to about 150 mM |
| 281 | about 2 to about 35 μM | about 50 to about 175 mM |
| 282 | about 2 to about 35 μM | About 50 to about 150 mM |
| 283 | about 2 to about 32 μM | about 20 to about 175 mM |
| 284 | about 2 to about 32 μM | about 20 to about 150 mM |
| 285 | about 2 to about 32 μM | about 50 to about 175 mM |
| 286 | about 2 to about 32 μM | About 50 to about 150 mM |
| 287 | about 2 to about 30 μM | about 20 to about 175 mM |
| 288 | about 2 to about 30 μM | about 20 to about 150 mM |
| 289 | about 2 to about 30 μM | about 50 to about 175 mM |
| 290 | about 2 to about 30 μM | About 50 to about 150 mM |
| 291 | about 2 to about 25 μM | about 20 to about 175 mM |
| 292 | about 2 to about 25 μM | about 20 to about 150 mM |
| 293 | about 2 to about 25 μM | about 50 to about 175 mM |
| 294 | about 2 to about 25 μM | about 50 to about 150 mM |
| 295 | about 2 to about 20 μM | about 20 to about 175 mM |
| 296 | about 2 to about 20 μM | about 20 to about 150 mM |
| 297 | about 2 to about 20 μM | about 50 to about 175 mM |
| 298 | about 2 to about 20 μM | About 50 to about 150 mM |
| 299 | about 2 to about 16 μM | about 20 to about 175 mM |
| 300 | about 2 to about 16 μM | about 20 to about 150 mM |
| 301 | about 2 to about 16 μM | about 50 to about 175 mM |
| 302 | about 2 to about 16 μM | About 50 to about 150 mM |
| 303 | about 2 to about 15 μM | about 20 to about 175 mM |
| 304 | about 2 to about 15 μM | about 20 to about 150 mM |
| 305 | about 2 to about 15 μM | about 50 to about 175 mM |
| 306 | about 2 to about 15 μM | About 50 to about 150 mM |
| 307 | about 2 to about 10 μM | about 20 to about 175 mM |
| 308 | about 2 to about 10 μM | about 20 to about 150 mM |
| 309 | about 2 to about 10 μM | about 50 to about 175 mM |
| 310 | about 2 to about 10 μM | About 50 to about 150 mM |
| 311 | about 2 to about 8 μM | about 20 to about 175 mM |
| 312 | about 2 to about 8 μM | about 20 to about 150 mM |
| 313 | about 2 to about 8 μM | about 50 to about 175 mM |
| 314 | about 2 to about 8 μM | About 50 to about 150 mM |
| 315 | about 2 to about 5 μM | about 20 to about 175 mM |
| 316 | about 2 to about 5 μM | about 20 to about 150 mM |
| 317 | about 2 to about 5 μM | about 50 to about 175 mM |
| 318 | about 2 to about 5 μM | About 50 to about 150 mM |

-continued

| # | Max. free Ca$^{2+}$ conc. | Salt conc. |
|---|---|---|
| 319 | about 2 to about 2.5 µM | about 20 to about 175 mM |
| 320 | about 2 to about 2.5 µM | about 20 to about 150 mM |
| 321 | about 2 to about 2.5 µM | about 50 to about 175 mM |
| 322 | about 2 to about 2.5 µM | About 50 to about 150 mM |

Particularly preferably, the concentration of free calcium in the compositions and samples of the present invention is ≤about 5 µM, preferably ≤about 2 µM, more preferably ≤about 1 µM and most preferably about 0 mM. Particularly preferably the concentration of monovalent salt in the compositions and samples is 20 to 125 mM, preferably 20 to 100 mM, most preferably 20 to 50 mM. Particularly preferably the concentration of monovalent salt in the compositions and samples is 30 to 125 mM, preferably 30 to 100 mM, most preferably 30 to 50 mM.

The compositions and samples of the present invention comprise a proteinase that can be inactivated under particularly mild conditions. The compositions therefore have advantageous utility in various molecular biology methods, which involve the subsequent or prior use of other enzymes. Such methods are discussed in more detail below. Thus, a further aspect is provided a kit comprising:

i) a composition of the present invention; and
ii) a second composition comprising a second enzyme.

The second enzyme is not a proteinase of the invention. Optionally said kit comprises multiple solutions comprising multiple enzymes, i.e. it comprises a third solution comprising a third enzyme, optionally a fourth solution comprising a fourth enzyme, and so on. Each solution present in the kits of the present invention preferably comprises a different enzyme, each of which is not a proteinase of the invention. Preferably the enzyme in the second and subsequent solutions is independently selected from the group consisting of a nuclease (preferably a deoxyribonuclease, an exonuclease, a Bal 31 nuclease, a ribonuclease, a mung bean nuclease or an S1 nuclease), a polymerase (preferably a DNA polymerase or an RNA polymerase), a reverse transcriptase, a ligase, (preferably a DNA ligase or an RNA ligase), a methylase, a transferase (preferably a polynucleotide adenylyl-transferase), a topisomerase, a guanylyl transferase, a proteinase other than proteinase X, and a phosphatase or a combination thereof.

Preferably, the kits of the present invention comprise a composition of the present invention and a second composition comprising a DNA polymerase or a reverse transcriptase.

The compositions and samples of the present invention comprise a proteinase that can be inactivated by particularly mild heat treatment steps. The compositions therefore have advantageous utility in various molecular biology methods in which the application of proteinases to a sample is necessary or desirable to digest one or more polypeptides in the sample, but in which it is also desirable to avoid deleteriously affecting the structure or function of one or more biological molecules present. The use of standard proteinases requires either i) inactivation using high temperatures for significant durations, which can be damaging to biological molecules of interest that are present; or ii) removal/dilution of the proteinase, which increases work flow, times and costs, and can lead to the loss or damage of biological molecules of interest. The present compositions permit methods that do not require such undesirable processing steps.

The present invention provides the methods discussed below. The definitions and preferred and optional features and embodiments described above in relation to the compositions, samples and kits of the present invention apply mutatis mutandis to any and all methods of the present invention. In the context of all methods of the invention, the polypeptides, sample, proteinase, enzymatically active fragment, free calcium, concentration of free calcium, monovalent salt and concentration of monovalent salt is as described anywhere else herein. In particular, any of the above-disclosed features and concentrations of free calcium (or calcium) and monovalent salt, and combinations thereof, are of use in the methods of the present invention, i.e. preferably the samples contacted or treated in the methods of the invention comprises a concentration of free calcium or monovalent salt, or any combination thereof, as disclosed anywhere else herein.

Thus, the term "sample" contacted in the methods of the invention refers to any composition comprising one or more polypeptides. Preferably, the sample comprises cellular matter. Preferably, the sample comprises a crude cell extract. Preferably, the sample comprises a partially purified cell extract. Preferably, the sample comprises a population of cells. The cells in said sample may be intact or lysed, preferably lysed. Preferably, the sample comprises a tissue sample or one or more body fluids.

Preferably, the sample is a fine needle biopsy. Preferably, the sample comprises encapsulated viruses. Proteinases may be used to digest the protein capsule of viruses in order to release the RNA/DNA therein for identification, quantification and/or amplification.

Preferably the sample has a volume of ≥10 µl. Preferably the sample has a volume of ≤1000 µl, more preferably ≤500 µl, more preferably ≤300 µl, more preferably ≤250 µl, more preferably ≤200 µl, more preferably ≤150 µl, more preferably ≤100 µl, more preferably ≤75 µl, more preferably ≤50 µl. Alternatively, the sample is a microfluidic sample. Preferably the microfluidic sample has a volume of ≥0.01 µl. Preferably the microfluidic sample has a volume of ≤10 µl, preferably ≤5 µl more preferably ≤1 µl, more preferably ≤0.5 µl more preferably ≤0.1 µl.

A reference anywhere herein to a proteinase is also a reference to enzymatically active fragments thereof, unless context dictates otherwise.

In all methods of the present invention, preferably the sample is essentially free of EDTA, preferably any calcium-chelating agent. The meaning of this term is as defined elsewhere herein. The sample is essentially free of EDTA, preferably any calcium-chelating agent after it has been contacted with the proteinase or enzymatically active fragment thereof.

Thus, in a further aspect there is provided a method of digesting polypeptides in a sample, said method comprising contacting the sample with a proteinase or an enzymatically active fragment thereof, said proteinase comprising the amino acid sequence of SEQ ID NO: 1 or comprising an amino acid sequence which is at least about 70% identical to SEQ ID NO: 1, wherein i) the concentration of free calcium in said sample is ≤about 80 µM; or
ii) the concentration of monovalent salt in said sample is ≥about 20 mM.

Alternatively viewed, the present invention provides a method of digesting polypeptides in a sample, said method comprising contacting the sample with a proteinase or an enzymatically active fragment thereof, said proteinase comprising the amino acid sequence of SEQ ID NO: 1 or comprising an amino acid sequence which is at least about 70% identical to SEQ ID NO: 1, wherein
i) the concentration of calcium in said sample is ≤about 80 μM and said sample is essentially free of EDTA; or
ii) the concentration of monovalent salt in said sample is ≥about 20 mM.

In all methods of the invention, particularly those in which the sample comprises monovalent salt, preferably the sample has a pH of 6.5 to 9.5, preferably 6.8 to 9.2, more preferably 7 to 9, more preferably 7.5 to 8.5, more preferably about 8.0. The present inventors have determined for the first time that the proteinases of the invention can be inactivated under mild conditions, including at neutral and near-neutral pH.

Preferably the concentration of free calcium (or calcium) in the sample is no more than about 80 μM and the concentration of monovalent salt in said sample is at least about 20 mM. Preferably, the concentration of monovalent salt in said sample is at least about 30 mM, more preferably at least about 40 mM, more preferably at least about 50 mM.

The terms "digest", "hydrolyse, "degrade" and "cleave" are used interchangeably herein and refer to the hydrolysis of peptide bonds within polypeptides in a sample. Digestion may be partial digestion or complete digestion. The proteinases of use in the invention are non-specific and will, given enough time, completely digest proteins in a sample under conditions that permit enzyme function.

The terms "contacting"/"contact", "applying to"/"application" and "adding to"/"addition" have their ordinary meanings and are used interchangeably herein.

In the methods of the invention, preferably the proteinase or enzymatically active fragment thereof is provided in the form of a composition of the invention, which are described above.

Preferably the proteinase or enzymatically active fragment thereof is added to said sample at a concentration of 0.001 mg/ml to 5 mg/ml, more preferably 0.05 mg/ml to 0.5 mg/ml, most preferably 0.015 mg/ml to 0.1 mg/ml. These concentrations are the concentrations of the proteinase in the sample.

Preferably, the activity of the proteinase or enzymatically active fragment thereof after being applied to the sample, i.e. in the sample, is from 0.07 U/ml to 325 U/ml, more preferably 3.25 U/ml to 32.5 U/ml, most preferably 1.0 U/μl to 6.5 U/ml, when determined using Assay A, above.

The proteinases and enzymatically active fragments thereof of the invention are thus used to degrade polypeptides in the sample. In particular, the method involves contacting the sample with a proteinase of the invention under conditions which permit the digestion of at least a portion of the polypeptides present in the sample. Thus, preferably, after the sample has been contacted with the proteinase or enzymatically active fragment thereof, the method further comprises a "digestion step", i.e. a step of incubating the sample under conditions to permit digestion of polypeptides in the sample. The amount of digestion required will depend on the aims and intentions of the person performing the method, and suitable conditions to achieve the required amount of digestion will be readily determinable by the person of ordinary skill in the art.

Preferably, the digestion step comprises heating the sample at a temperature between 4 and 65° C., more preferably between 20 and 55° C., most preferably between 30 and 55° C. Preferably, the incubation step has a duration of 1 second to 45 minutes, more preferably 30 seconds to 30 minutes, more preferably 1 to 15 minutes, more preferably 1 to 10 minutes, still more preferably 1 to 5 minutes. If a temperature at the higher end of these ranges is used, the duration of incubation may be at the lower end of these ranges, and vice versa. The skilled person will be aware that very short incubations of 1 or 2 seconds would be sufficient in the case of methods performed with microfluidic samples, and other methods in which the amount of substrate present in the sample is small.

Preferably, the above methods comprise a subsequent "inactivation step", i.e. a step of heating the sample to inactivate the proteinase or enzymatically active fragment thereof. Such an inactivation step is performed after the step of contacting the sample with the proteinase and after the step of incubating the sample under conditions to permit digestion of polypeptides in the sample.

These steps of digestion and inactivation will typically be incubations and are described herein, in particular in the Examples. The above-mentioned features and embodiments relating to pH and (free) calcium, monovalent salt and EDTA concentrations are the conditions in the sample at the point at which the inactivation step is performed.

Thus, in a further aspect there is provided a method of digesting polypeptides in a sample, said method comprising the steps of:
a) contacting the sample with a proteinase or an enzymatically active fragment thereof, said proteinase comprising the amino acid sequence of SEQ ID NO: 1 or comprising an amino acid sequence which is at least about 70% identical to SEQ ID NO: 1;
b) incubating the sample under conditions which permit at least partial digestion of polypeptides in the sample; and
c) heating the sample to inactivate the proteinase or enzymatically active fragment thereof; wherein
  i) the concentration of free calcium in said sample is ≤about 80 μM; or
  ii) the concentration of monovalent salt in said sample is ≥about 20 mM.

Alternatively viewed, step c) of the above method comprises
c) heating the sample to inactivate the proteinase or enzymatically active fragment thereof; wherein
  i) the concentration of calcium in said sample is ≤ about 80 μM and said sample is essentially free of EDTA; or
  ii) the concentration of monovalent salt in said sample is ≥about 20 mM.

Preferably the concentration of free calcium (or calcium) in said sample is no more than about 80 μM and the concentration of monovalent salt in said sample is at least about 20 mM. Preferably, the monovalent salt is a monovalent inorganic salt, preferably a sodium salt or a potassium salt, more preferably potassium chloride or sodium chloride, most preferably sodium chloride. The digestion step b) is as discussed above.

As mentioned above, digestion may be partial digestion or complete digestion. The proteinases of use in the invention are non-specific and will, given enough time, completely digest proteins in a sample under conditions that permit enzyme function. Thus, by "digesting polypeptides in a sample" it is meant that the amount of full length polypeptides in the sample is reduced to some extent. The extent of protein digestion can be assayed in a straightforward manner using a number of well-known assays. It would be within the competencies of the skilled person to design a suitable assay for their intended purposes. For instance, the remaining activity of an enzyme in the sample can be used as measure of protein degradation. Changes in proteome profiles, which can be determined for instance via mass spectrometry, can also be used to determine the extent of polypeptide degradation in a sample. A simple assay to visualise the extent of protein degradation is to perform SDS Page and stain with a protein staining dye, such as Coomassie blue, or other visual reporter molecule. Intact proteins will display as bands along the gel, whereas the bands become less sharp with increased protein degradation. The extent of degradation can be quantified using software-based image analysis.

Preferably, the sample to which the proteinase is added comprises cellular matter. Preferably, the sample comprises a crude cell extract. Preferably, the sample comprises a partially purified cell extract. Preferably, the sample comprises a population of cells. The cells in said sample may be intact or lysed, preferably lysed. Preferably, the sample comprises a tissue sample or one or more body fluids. Preferably, the sample comprises from about 1 to about 1,000,000 cells. In a preferred embodiment, the sample comprises 1 to 10,000 cells, preferably 1 to 1000 cells, preferably 1 to 100 cells. In a preferred embodiment, the sample comprises a single cell. In other preferred embodiments, the sample comprises 100 to 1,000,000 cells, preferably 100 to 10,000 cells, preferably 100 to 1000 cells. Preferably the sample is a fine needle or liquid biopsy. Proteinases can be used in the lysis of cellular matter.

The proteinases of the invention may be used to digest any polypeptide present in the sample. Preferably the polypeptides in the sample include capsid or scaffolding proteins, DNA or RNA binding proteins, and/or enzymes acting on DNA or RNA, such as those described elsewhere herein.

In a further aspect the present invention provides a method of inactivating a proteinase or an enzymatically active fragment thereof in a sample, said proteinase comprising the amino acid sequence of SEQ ID NO: 1 or comprising an amino acid sequence which is at least about 70% identical to SEQ ID NO: 1, wherein said method comprises the step of heating the sample to inactivate said proteinase or enzymatically active fragment, and wherein
  i) the concentration of free calcium in said sample is ≤about 80 µM; or
  ii) the concentration of monovalent salt in said sample is ≥about 20 mM.

Alternatively viewed, the present invention provides a method of inactivating a proteinase or an enzymatically active fragment thereof in a sample, said proteinase comprising the amino acid sequence of SEQ ID NO: 1 or comprising an amino acid sequence which is at least about 70% identical to SEQ ID NO: 1, wherein said method comprises the step of heating the sample to inactivate said proteinase or enzymatically active fragment, and wherein
  i) the concentration of calcium in said sample is ≤about 80 µM and said sample is essentially free of EDTA, preferably essentially free of calcium chelating agents; or
  ii) the concentration of monovalent salt in said sample is ≥about 20 mM.

In all of the methods of the present invention, preferably the concentration of free calcium (or calcium) in said sample is no more than about 80 µM and the concentration of monovalent salt in said sample is at least about 20 mM. Preferably, the monovalent salt is a monovalent inorganic salt, preferably a sodium salt or a potassium salt, more preferably potassium chloride or sodium chloride, most preferably sodium chloride.

As mentioned above, the concentrations of free calcium (or calcium) and monovalent salt described anywhere herein in the methods of the present invention are the concentrations in the sample at the start of the inactivation step. Preferably, the concentrations are also those in the sample after it has been contacted with the proteinase or enzymatically active fragment thereof. In the methods of the present invention, preferably the proteinase is not removed from the sample, e.g. by purification, extraction or centrifugation, and preferably the concentration of the proteinase in the sample is not diluted prior to or during the inactivation step.

The invention is based on the surprising finding that the proteinases described herein become thermolabile under mild conditions given certain free calcium and/or monovalent salt concentrations. These conditions therefore need to be present during the inactivation steps of the methods of the invention. The person of ordinary skill in the art will readily appreciate that contacting the sample with a proteinase or enzymatically active fragment thereof will increase the volume of the sample, and may therefore reduce the concentration of free calcium and monovalent salt therein. In use, preferably the compositions of the invention have small volumes which do not significantly alter the volume of the sample. Similarly, the proteinase of the invention may be provided in a solution in which the concentration of free calcium exceeds about 80 µM and/or in which the concentration of monovalent salt is less than about 20 mM, but wherein the volume and concentration of free calcium and/or monovalent salt in the sample to which it is added is such that the resulting sample to which the proteinase or enzymatically active fragment thereof has been applied comprises a free calcium concentration of no more than about 80 µM and a monovalent salt concentration of at least about 20 mM, in accordance with the invention.

Preferably, said the inactivation step in the methods of the invention comprises reducing the activity of said proteinases in said sample by at least 75%, more preferably at least 80% or at least 85%, more preferably at least 90%, at least 95%, at least 96%, at least 97%, at least 98%, at least 99% as compared to the activity of the proteinase in the sample prior to said inactivation step being performed. Alternatively viewed, preferably said inactivation step results in less than 25%, more preferably less than 20%, less than 15%, less than 10%, less than 5%, less than 4%, less than 3%, less than 2%, less than 1% remaining proteinase activity. Preferably, the proteinase is completely inactivated, i.e. preferably, no detectable proteinase activity remains.

Even when the solution comprising the heat-treated proteinase is returned to a temperature below 40° C., the proteinases of the invention do not regain activity, i.e. there is substantially no residual activity; specifically, less than 10%, preferably less than 5%, 2%, 1%, 0.5% or 0.1%, most preferably no detectable proteinase activity remains. Thus, the inactivation referred to herein is irreversible.

As mentioned above, suitable assays for determining proteinase activity are known in the art. Such assays can thus be used to determine the proteinase activity of a proteinase or enzymatically active fragment thereof that has undergone inactivation by heat-treatment as compared to the proteinase activity of the same proteinase that has not undergone heat-treatment, thereby determining the remaining activity or the extent of inactivation achieved by the inactivation step. Any proteinase activity assay can be used to determine the relative activity of a heat-treated proteinase as compared to an untreated proteinase. The skilled person would be well aware that the same heat-treated and untreated proteinases should be kept under identical conditions and assayed using identical protocols. Preferably, the assay used is Assay A above and preferably, the untreated proteinase is kept on ice until proteinase activity is determined. Further preferred assays of remaining activity are those disclosed in the Examples.

Thus, the remaining activity after the inactivation step of the methods of the present invention, i.e. the extent of inactivation achieved by the inactivation step of the methods of the present invention, can readily be determined by the person of ordinary skill in the art by determining the proteinase activity of the proteinase having undergone the inactivation step using a suitable proteinase assay under suitable conditions and comparing it to the activity of same proteinase that has not undergone such an inactivation step, wherein activities are determined using the same assay under the same conditions. Preferably the assay used is Assay A above or any one of the assays used in the present Examples. Preferably, the untreated proteinase is kept on ice until proteinase activity is determined.

The extent of inactivation can be expressed in terms of percentage inactivation or percentage remaining activity, relative to the activity of the untreated proteinase.

Due to the concentration of free calcium in the sample being no more than about 80 µM and/or the concentration of monovalent salt in the sample being at least about 20 mM, the proteinases and enzymatically active fragments thereof in the sample can be inactivated by using mild heating conditions.

It would be within the competencies of the person of ordinary skill in the art to heat a sample to a desired temperature for a desired period of time, for instance via the use of a heat block, microwave, Joule heating apparatus, laser heating apparatus, or water bath.

The temperature to which the sample is heated, i.e. to which the proteinase is exposed, during the inactivation step of the present methods is referred to as the inactivation temperature. Preferably said inactivation temperature is ≤about 70° C., preferably ≤about 67° C., preferably ≤about 65° C., preferably ≤about 64° C., preferably ≤about 63° C. preferably ≤about 62° C., preferably ≤about 61° C., preferably ≤about 60° C., preferably ≤about 58° C.

Preferably said inactivation step comprises heating the sample containing the proteinase to a temperature of from about 50 to about 67° C., preferably from about 50 to about 65° C., preferably from about 50 to about 64° C., preferably from about 50 to about 63° C., preferably from about 50 to about 62° C., preferably from about 50 to about 61° C., preferably from about 50 to about 60° C., preferably from about 50 to about 58°.

Preferably said inactivation step comprises heating the sample containing the proteinase to a temperature of from about 53 to about 67° C., preferably from about 53 to about 65° C., preferably from about 53 to about 64° C., preferably from about 53 to about 63° C., preferably from about 53 to about 62° C., preferably from about 53 to about 61° C., preferably from about 53 to about 60° C., preferably from about 53 to about 58°.

Preferably said inactivation step comprises heating the sample containing the proteinase to a temperature of from about 55 to about 67° C., preferably from about 55 to about 65° C., preferably from about 55 to about 64° C., preferably from about 55 to about 63° C., preferably from about 55 to about 62° C., preferably from about 55 to about 61° C., preferably from about 55 to about 60° C.

Preferably said inactivation step comprises heating the sample containing the proteinase to a temperature of from about 56 to about 67° C., preferably from about 56 to about 65° C., preferably from about 56 to about 64° C., preferably from about 56 to about 63° C., preferably from about 56 to about 62° C., preferably from about 56 to about 61° C., preferably from about 56 to about 60° C.

Preferably said inactivation step comprises heating the sample containing the proteinase to a temperature of from about 57 to about 67° C., preferably from about 57 to about 65° C., preferably from about 57 to about 64° C., preferably from about 57 to about 63° C., preferably from about 57 to about 62° C., preferably from about 57 to about 61° C., preferably from about 57 to about 60° C.

Preferably said inactivation step comprises heating the sample containing the proteinase to a temperature of from about 58 to about 67° C., preferably from about 58 to about 65° C., preferably from about 58 to about 64° C., preferably from about 58 to about 63° C., preferably from about 58 to about 62° C., preferably from about 58 to about 61° C., preferably from about 58 to about 60° C.

Preferably said inactivation step comprises heating the sample containing the proteinase to a temperature of from about 59 to about 67° C., preferably from about 59 to about 65° C., preferably from about 59 to about 64° C., preferably from about 59 to about 63° C., preferably from about 59 to about 62° C., preferably from about 59 to about 61° C., preferably from about 59 to about 60° C.

Preferably, said inactivation step comprises heating the sample containing the proteinase to a temperature of from about 55° C. to about 65° C., preferably from about 60° C. to about 65° C., more preferably from about 55° C. to about 60° C.

Particularly preferably, said inactivation step comprises heating at from about 53° C. to about 60° C., more preferably from about 53° C. to about 58° C., more preferably at about 55° C.

Particularly preferably, said inactivation step comprises heating at from about 58° C. to about 67° C., more preferably from about 58° C. to about 63° C., more preferably at about 60° C.

Particularly preferably, said inactivation step comprises heating at from about 60 to about 67° C., more preferably from about 63 to about 67° C., more preferably at about 65° C.

Preferably, the inactivation step comprises heating the sample at any one of the above temperatures for a period of time called the "holding time". The necessary holding time is dependent on the inactivation temperature being used, the concentration of free calcium and monovalent salt in the sample, and the degree of inactivation required. Given the teaching in the present application, the person of ordinary skill in the art would be able to select a holding time for their particular purpose.

Preferably, the holding time is ≤about 75 minutes, preferably ≤about 60 minutes, preferably ≤about 55 minutes, preferably ≤about 50 minutes, preferably ≤about 45 minutes, preferably ≤about 40 minutes, preferably ≤about 35 minutes, preferably ≤about 30 minutes, preferably ≤about 25 minutes, preferably ≤about 20 minutes, preferably ≤about 15 minutes, preferably ≤about 10 minutes, preferably ≤about 5 minutes, preferably ≤about 2 minutes.

Preferably, the holding time is at least about 1 minute, preferably at least about 2 minutes, preferably at least about 5 minutes, preferably at least about 10 minutes, preferably at least about 15 minutes, preferably at least about 20 minutes, preferably at least about 25 minutes, preferably at least about 30 minutes, preferably at least about 35 minutes, preferably at least about 40 minutes, preferably at least about 45 minutes, preferably at least about 50 minutes, preferably at least about 60 minutes.

Preferably, the holding time is from about 2 to about 75 minutes, preferably from about 2 to about 60 minutes, preferably from about 2 to about 55 minutes, preferably from about 2 to about 50 minutes, preferably from about 2 to about 45 minutes, preferably from about 2 to about 40 minutes, preferably from about 2 to about 35 minutes, preferably from about 2 to about 30 minutes, preferably from about 2 to about 25 minutes, preferably from about 2 to about 20 minutes, preferably from about 2 to about 15 minutes, preferably from about 2 to about 10 minutes, preferably from about 2 to about 5 minutes.

Preferably, the holding time is from about 5 to about 75 minutes, preferably from about 5 to about 60 minutes, preferably from about 5 to about 55 minutes, preferably from about 5 to about 50 minutes, preferably from about 5 to about 45 minutes, preferably from about 5 to about 40 minutes, preferably from about 5 to about 35 minutes preferably from about 5 to about 30 minutes, preferably from about 5 to about 25 minutes, preferably from about 5 to about 20 minutes, preferably from about 5 to about 15 minutes, preferably from about 5 to about 10 minutes.

Preferably, the holding time is from about 10 to about 75 minutes, preferably from about 10 to about 60 minutes, preferably from about 10 to about 55 minutes, preferably from about 10 to about 50 minutes, preferably from about 10 to about 45 minutes, preferably from about 10 to about 40 minutes, preferably from about 10 to about 35 minutes, preferably from about 10 to about 30 minutes, preferably from about 10 to about 25 minutes, preferably from about 10 to about 20 minutes, preferably from about 10 to about 15 minutes.

Preferably, the holding time is from about 15 to about 75 minutes, preferably from about 15 to about 60 minutes, preferably from about 15 to about 55 minutes, preferably from about 15 to about 50 minutes, preferably from about 15 to about 45 minutes, preferably from about 15 to about 40 minutes, preferably from about 15 to about 35 minutes, preferably from about 15 to about 30 minutes, preferably from about 15 to about 25 minutes, preferably from about 15 to about 20 minutes.

Preferably, the holding time is from about 20 to about 75 minutes, preferably from about 20 to about 60 minutes, preferably from about 20 to about 55 minutes, preferably from about 20 to about 50 minutes, preferably from about 20 to about 45 minutes, preferably from about 20 to about 40 minutes, preferably from about 20 to about 35 minutes, preferably from about 20 to about 30 minutes, preferably from about 20 to about 25 minutes.

Preferably, the holding time is from about 25 to about 75 minutes, preferably from about 25 to about 60 minutes, preferably from about 25 to about 55 minutes, preferably from about 25 to about 50 minutes, preferably from about 25 to about 45 minutes, preferably from about 25 to about 40 minutes, preferably from about 25 to about 35 minutes, preferably from about 25 to about 30 minutes.

Preferably, the holding time is from about 30 to about 75 minutes, preferably from about 30 to about 60 minutes, preferably from about 30 to about 55 minutes, preferably from about 30 to about 50 minutes, preferably from about 30 to about 45 minutes, preferably from about 30 to about 40 minutes, preferably from about 30 to about 35 minutes.

Preferably, the holding time is from about 35 to about 75 minutes, preferably from about 35 to about 60 minutes, preferably from about 35 to about 55 minutes, preferably from about 35 to about 50 minutes, preferably from about 35 to about 45 minutes, preferably from about 35 to about 40 minutes.

Preferably, the holding time is from about 40 to about 75 minutes, preferably from about 40 to about 60 minutes, preferably from about 40 to about 55 minutes, preferably from about 40 to about 50 minutes, preferably from about 40 to about 45 minutes.

Preferably, the holding time is from about 45 to about 75 minutes, preferably from about 45 to about 60 minutes, preferably from about 45 to about 55 minutes, preferably from about 45 to about 50 minutes.

Preferably, the holding time is from about 50 to about 75 minutes, preferably from about 50 to about 60 minutes, preferably from about 50 to about 55 minutes.

Preferably, the holding time is from about 55 to about 75 minutes, preferably from about 55 to about 60 minutes.

Preferably, the holding time is from about 5 minutes to about 40 minutes, preferably from about 10 to about 35 minutes, preferably from about 15 to about 30 minutes. Particularly preferably, the holding time is from about 5 to about 15 minutes, or from about 10 to about 20 minutes, or from about 20 to about 40 minutes, preferably from about 25 to about 35 minutes.

The above holding times are particularly suitable for samples having a volume of ≤1000 µl, preferably ≤500 µl, more preferably ≤300 µl, more preferably ≤250 µl, more preferably ≤200 µl, more preferably ≤150 µl, more preferably ≤100 µl, more preferably ≤75 µl, more preferably ≤50 µl.

The skilled person will be aware that adjustments to one of the heating temperature and the holding time can be compensated for by adjusting the other. For instance, increasing the inactivation temperature might permit the holding time to be reduced. Conversely, increasing the holding time might permit a lower inactivation temperature to be used.

In addition, the skilled person will be aware that when the amount of proteinase present is small, e.g. in the case of microfluidic samples, sufficient inactivation could occur within a very short time frame, for instance 1 to 30 seconds, preferably 1 to 20 seconds, preferably 1 to 10 seconds, preferably 1 to 5 seconds and potentially even in only 1 or 2 seconds. Any of the above-mentioned inactivation temperatures may be used for these short holding times. For such short holding times to be effective, the sample containing the proteinase to be inactivated preferably has a volume of ≤10 µl, preferably ≤5 µl more preferably ≤1 µl, more preferably ≤0.5 µl more preferably ≤0.1 µl.

In the methods of the present invention that comprise an inactivation step, any of the above inactivation temperatures may be used in combination with any of the above holding times. Expressly disclosed are any and all combinations of the inactivation temperatures and holding times disclosed anywhere herein.

Preferably, the inactivation step comprises heating at a temperature of from about 53° C. to about 67° C., preferably from about 55° C. to about 65° C., preferably from about 55 to about 63° C., for a holding time of from about 2 to about 75 minutes, preferably about 5 to about 40 minutes, more preferably about 10 to about 30 minutes, e.g. about 10, about 15 or about 30 minutes.

Preferably, the inactivation step comprises heating at a temperature of from about 55 to about 60° C. for a holding time of from about 2 to about 75 minutes, preferably about 5 to about 40 minutes, more preferably about 10 to about 30 minutes, e.g. about 10, about 15 or about 30 minutes.

Preferably, the inactivation step comprises heating at a temperature of from about 60 to about 65° C. for a holding time of from about 2 to about 75 minutes, preferably about 5 to about 40 minutes, more preferably about 10 to about 20 minutes, e.g. about 10 or about 15 minutes.

Preferred inactivation steps of the present invention are as follows:

A) Heating at about 53 to about 58° C., preferably at about 55° C., for about 45 to about 75 minutes, more preferably about 45 to about 60 minutes, more preferably about 60 minutes.

In such embodiments, the concentration of free calcium in the sample is preferably ≤about 10 μM, more preferably ≤about 8 μM, more preferably ≤5 μM, more preferably, the sample does not comprise free calcium.

Alternatively or in addition in such embodiments, the concentration of monovalent salt in the sample is preferably at least about 50 mM, more preferably at least about 75 mM, more preferably at least about 100 mM or at least about 150 mM.

B) Heating at about 58 to about 63° C., preferably at about 60° C., for the following times set out in any one of B1 to B4 below:

B1) for about 2 to about 40 minutes, more preferably about 5 to about 30 minutes.

In such embodiments, the concentration of free calcium in the sample is preferably ≤about 80 μM, more preferably ≤about 65 μM, more preferably ≤about 35 μM, more preferably ≤about 20 μM, more preferably ≤about 10 μM, more preferably ≤about 5 μM.

Alternatively or in addition in such embodiments, the concentration of monovalent salt in the sample is preferably at least about 20 mM, more preferably at least about 25 mM, more preferably at least about 30 mM, more preferably at least about 40 mM, more preferably at least about 50 mM, more preferably at least about 75 mM, more preferably at least about 100 mM, more preferably at least about 150 mM.

B2) about 5 to about 15 minutes, more preferably about 10 minutes.

In such embodiments, the concentration of free calcium in the sample is preferably ≤about 10 μM, ≤about 8 μM, more preferably ≤about 5 μM, more preferably, the sample does not comprise free calcium.

Alternatively or in addition in such embodiments, the concentration of monovalent salt in the sample is preferably at least about 75 mM, more preferably at least about 100 mM, more preferably at least about 150 mM.

B3) about 10 to about 20 minutes, more preferably about 15 minutes.

In such embodiments, the concentration of free calcium in the sample is preferably ≤about 35 μM, more preferably ≤about 16 μM, more preferably ≤about 8 μM, more preferably ≤about 5 μM, more preferably, the sample does not comprise free calcium.

Alternatively or in addition in such embodiments, the concentration of monovalent salt in the sample is preferably at least about 50 mM, more preferably at least about 75 mM, more preferably at least about 100 mM, more preferably at least about 150 mM.

B4) about 20 to 40 minutes, more preferably about 30 minutes.

In such embodiments, the concentration of free calcium in the sample is preferably ≤about 80 μM ≤about 65 μM, more preferably ≤about 35 μM, more preferably ≤about 30 μM, more preferably ≤about 16 μM.

Alternatively or in addition in such embodiments, the concentration of monovalent salt in the sample is preferably at least about 25 mM, more preferably at least about 30 mM, more preferably at least about 40 mM, more preferably at least about 50 mM, more preferably at least about 75 mM, more preferably at least about 100 mM.

Preferably, in such embodiments, if the monovalent salt concentration is 100 mM or less, then the calcium concentration is no more than 30 μM. Preferably, if the monovalent salt concentration is 75 mM or less, then the calcium concentration is no more than 20 μM. Preferably, if the monovalent salt concentration is 50 mM or less, then the calcium concentration is no more than 10 μM.

C) Heating at about 63 to about 67° C., preferably at about 65° C. for a maximum of about 15 minutes, more preferably for a maximum of about 10 minutes, more preferably a maximum of about 5 minutes.

In such embodiments, the concentration of free calcium in the sample is preferably ≤about 80 μM, more preferably ≤about 65 μM, more preferably ≤about 35 μM, more preferably ≤about 20 μM, more preferably ≤about 10 μM, more preferably ≤about 5 μM.

Alternatively or in addition in such embodiments, the concentration of monovalent salt in the sample is preferably at least about 20 mM, more preferably at least about 25 mM, more preferably at least about 30 mM, more preferably at least about 40 mM, more preferably at least about 50 mM, more preferably at least about 75 mM, more preferably at least about 100 mM.

The free calcium dependent and monovalent salt dependent effects on thermolability determined by the present inventors also permit the inactivation of the proteinases and enzymatically active fragments thereof of the invention at high temperatures for surprisingly short amounts of time. Thus, in an alternative preferred embodiment, the inactivation step comprises D) Heating at about 65 to about 70° C., preferably about 67 to about 70° C., more preferably about 67° C. or about 70 for a maximum of about 5 minutes, more preferably for a maximum of about 2 minutes.

In such embodiments, the concentration of free calcium in the sample is preferably ≤about 80 μM, more preferably ≤about 65 μM, more preferably ≤about 35 μM, more preferably about ≤20 μM.

Alternatively or in addition in such embodiments, the concentration of monovalent salt in the sample is preferably at least about 20 mM, more preferably at least about 25 mM, more preferably at least about 30 mM, more preferably at least about 40 mM, more preferably at least about 50 mM, more preferably at least about 75 mM, more preferably at least about 100 mM.

Most preferably, the heating/inactivation step c) comprises heating the sample to a temperature of 55 to 60° C. for a duration of 15 to 30 minutes.

It will be readily apparent to the skilled person that adjustments to one of the parameters heating time, heating temperature, free calcium concentration and monovalent salt concentration can be compensated for by adjusting one or more of the others.

Crucially, however, according to the present invention, the maximum free calcium concentration is 80 μM. It is at or below this free calcium concentration that the thermolability of the proteinases of the invention is induced to the extent that substantial inactivation (75% inactivation) of the proteinases can be achieved under advantageously mild conditions, particularly with inactivation temperatures of 53 to 67° C. and holding times of 2 to 75 minutes, preferably 5 to 60 minutes, more preferably 10 to 40 minutes, preferably 15 to 30 minutes.

Similarly, according to the present invention, the minimum monovalent salt concentration is 20 mM. It is at or above this monovalent salt concentration that the thermolability of the proteinases of the invention is induced to the extent that substantial inactivation (75% inactivation) of the proteinases can be achieved under advantageously mild conditions particularly with inactivation temperatures of 53 to 67° C. and holding times of 2 to 75 minutes, preferably 5 to 60 minutes, more preferably 10 to 40 minutes, preferably 15 to 30 minutes.

As mentioned above, typical inactivation protocols for the gold standard proteinase used in the field require much harsher conditions: e.g. heating at 75° C. for 5 minutes (Bio-Rad protocol), heating at 95° C. for 10 minutes (New England BioLabs protocol), heating at 70° C. for 15 minutes (Qiagen protocol).

In the methods of the present invention, preferably the samples are essentially free of, more preferably do not comprise EDTA, more preferably any calcium-chelating agent, at the point at which it is contacted with the proteinase. Alternatively viewed, preferably the sample to which the proteinase is applied is essentially free of, more preferably does not comprise EDTA, preferably any calcium-chelating agent. Preferably, the methods of the present invention do not comprise a step of applying EDTA, preferably any calcium-chelating agent, to the sample after the addition of the proteinase. The sample may have been contacted with a calcium-chelating agent at some point earlier in the workflow or during its preparation, but in that case, the calcium-chelating agent must have been removed prior to the application of the proteinase. Calcium chelating agents are as described elsewhere herein and it is within the competencies of one of ordinary skill in the art to remove them from a sample prior to contacting the sample with the proteinase.

As mentioned above, in all methods of the invention, particularly those in which the sample comprises monovalent salt, preferably the sample has a pH of 6.5 to 9.5, preferably 6.8 to 9.2, more preferably 7 to 9, more preferably 7.5 to 8.5, more preferably about 8.0. The present inventors have determined for the first time that the proteinases of the invention can be inactivated under mild conditions, including at neutral and near-neutral pH. Thus, preferably, the method further comprises the step of adjusting the pH of the sample to 6.5 to 9.5, preferably 6.8 to 9.2, more preferably 7 to 9, more preferably 7.5 to 8.5, more preferably about 8.0 prior to the inactivation step. Steps for adjusting the pH of a sample are well known to those of ordinary skill in the art and any such steps may be used in the methods of the present invention.

Preferably the sample to which the proteinase is added has a volume of ≥10 µl. Preferably the sample has a volume of ≤1000 µl, more preferably ≤500 µl, more preferably ≤300 µl, more preferably ≤250 µl, more preferably ≤200 µl, more preferably ≤150 µl, more preferably ≤100 µl, more preferably ≤75 µl, more preferably ≤50 µl. Alternatively, the sample is a microfluidic sample. Preferably the microfluidic sample has a volume of ≥0.01 µl. Preferably the microfluidic sample has a volume of ≤10 µl, preferably ≤5 µl more preferably ≤1 µl, more preferably ≤0.5 µl more preferably ≤0.1 µl.

Preferably, the sample to which the proteinase or enzymatically active fragment is added comprises a biological molecule of interest and one or more contaminating, i.e. unwanted, polypeptides.

Thus in a further aspect the present invention provides a method of isolating or purifying a biological molecule of interest from a sample, wherein said sample comprises one or more contaminating polypeptides, said method comprising:
  a) contacting the sample with a proteinase or an enzymatically active fragment thereof, said proteinase comprising the amino acid sequence of SEQ ID NO: 1 or comprising an amino acid sequence which is at least about 70% identical to SEQ ID NO: 1;
  b) incubating the sample under conditions which permit at least partial digestion of polypeptides in the sample; and
  c) heating the sample to inactivate the proteinase or enzymatically active fragment thereof, wherein
    i) the concentration of free calcium in said sample is ≤about 80 µM; or
    ii) the concentration of monovalent salt in said sample is ≥about 20 mM; and
  d) optionally removing the biological molecule of interest from the sample.

Alternatively viewed step c) of the above method comprises: heating the sample to inactivate the proteinase or enzymatically active fragment thereof, wherein
  i) the concentration of calcium in said sample is ≤about 80 µM and said sample is essentially free of EDTA; or
  ii) the concentration of monovalent salt in said sample is ≥about 20 mM.

Preferably, the "biological molecule of interest" is a nucleic acid molecule, preferably a DNA or RNA molecule. Preferably, the biological molecule of interest is itself a polypeptide. The biological molecule of interest is not a proteinase or enzymatically active fragment thereof.

The proteinases of the invention may be used to digest the protein capsule of viruses in order to release the RNA/DNA therein for identification, quantification and/or amplification. Thus, preferably, the biological sample comprises one or more encapsulated viruses, the biological molecule of interest is a nucleic acid molecule, preferably RNA or DNA, of said virus, the contaminating polypeptides are those of the virus protein capsule and step b) comprises incubating the sample under conditions which permit at least partial digestion of the protein capsule of said virus(es), i.e. sufficient digestion to release said nucleic acid molecules from said capsule.

Preferably, the sample comprises chromatin, the biological molecule of interest is DNA free of bound histones, the contaminating proteins are histones bound thereto and step b) comprises incubating the sample under conditions which permit at least partial digestion of the histones in the sample.

Preferably the sample is or comprises the product of a nucleic amplification reaction, e.g. a PCR reaction, and comprises DNA bound polymerase, the biological molecule of interest is DNA free of bound polymerase, the contaminating protein is the bound polymerase and step b) comprises incubating the sample under conditions which permit at least partial digestion of the polymerase in the sample. Amplification methods include, but are not limited to, PCR and modifications thereto, 3SR, SDA, LAR or LCR and LAMP and modifications thereto.

The term "nucleic acid amplification reaction" refers to any in vitro means for increasing the number of copies of a target sequence of nucleic acid or its complementary sequence.

A "product of a nucleic acid amplification reaction" is therefore considered to comprise essentially all of the components obtained directly from the final amplification step of the reaction in question. Other components may be added or certain of the components may undergo some modification or processing, but essentially none of the components, or at least none of the nucleic acid components, will have been removed. Preferably the product of a nucleic acid amplification reaction is the direct product of the final amplification step; however, it might also be preferable for the product of a nucleic acid amplification reaction to undergo a treatment to effect the dephosphorylation of any unincorporated NTPs, e.g. a treatment with an alkaline phosphatase, preferably a thermolabile alkaline phosphatase, for instance the heat-labile shrimp alkaline phosphatase (SAP), prior to treatment with the proteinase of the invention. An advantageous recombinant SAP is available from ArcticZymes™ AS.

Preferably, the biological molecule of interest in said sample is fused via one or more peptide bonds to a molecule, preferably a polypeptide. In a further aspect the present invention therefore provides a method of releasing a biological molecule of interest from a molecule, preferably a polypeptide, fused thereto via one or more peptide bonds, said method comprising:

a) contacting the sample with a proteinase or an enzymatically active fragment thereof, said proteinase comprising the amino acid sequence of SEQ ID NO: 1 or comprising an amino acid sequence which is at least about 70% identical to SEQ ID NO: 1;

b) incubating the sample under conditions which permit release of the biological molecule of interest via digestion of one or more of the peptide bonds; and c) heating the sample to inactivate the proteinase or enzymatically active fragment thereof, wherein
  i) the concentration of free calcium in said sample is ≤about 80 μM; or
  ii) the concentration of monovalent salt in said sample is ≥about 20 mM; and d) optionally removing the biological molecule of interest from the sample.

Alternatively viewed, step c) of the above method comprises heating the sample to inactivate the proteinase or enzymatically active fragment thereof, wherein
  i) the concentration of calcium in said sample is ≤about 80 μM and said sample is essentially free of EDTA; or
  ii) the concentration of monovalent salt in said sample is ≥about 20 mM Preferably, the biological molecule of interest is a polypeptide or protein and the molecule to which it is fused is a polypeptide signal sequence or fusion tag, preferably a his-tag (e.g. a hexahistidine-tag), a FLAG-tag, maltose binding protein (MBP), glutathione S-transferase (GST), thioredoxin (TRX), small ubiquitin-like modifier (SUMO), ubiquitin (Ub) or green fluorescent protein (GFP).

In a further aspect the present invention provides a method of producing a peptide of interest from a precursor polypeptide, said method comprising a) contacting the polypeptide with a proteinase or an enzymatically active fragment thereof, said proteinase comprising the amino acid sequence of SEQ ID NO: 1 or comprising an amino acid sequence which is at least about 70% identical to SEQ ID NO: 1;

b) incubating the sample under conditions which permit digestion of the precursor polypeptide to release the peptide of interest; and c) heating the sample to inactivate the proteinase or enzymatically active fragment thereof, wherein
  i) the concentration of free calcium in said sample is ≤about 80 μM; or
  ii) the concentration of monovalent salt in said sample is ≥about 20 mM; and d) optionally removing the biological molecule of interest from the sample.

Alternatively viewed, step c) of the above method comprises heating the sample to inactivate the proteinase or enzymatically active fragment thereof, wherein
  i) the concentration of calcium in said sample is ≤about 80 μM and said sample is essentially free of EDTA; or
  ii) the concentration of monovalent salt in said sample is ≥about 20 mM Proteinases are also used to dissociate one or more cells from other cells within tissues, or from substrates to which they are adhered, via digestion of extracellular matrix proteins. In a further aspect the present invention provides a method of dissociating one or more cells from other cells within a tissue, or from a substrate to which said one or more cells are adhered, said method comprising:

a) contacting the one or more cells with a proteinase or an enzymatically active fragment thereof, said proteinase comprising the amino acid sequence of SEQ ID NO: 1 or comprising an amino acid sequence which is at least about 70% identical to SEQ ID NO: 1;

b) incubating the sample under conditions which permit release of the one or more cells via digestion of one or more extracellular matrix proteins; and c) heating the sample to inactivate the proteinase or enzymatically active fragment thereof, wherein
  i) the concentration of free calcium in said sample is ≤about 80 μM; or
  ii) the concentration of monovalent salt in said sample is ≥about 20 mM; and d) optionally removing the biological molecule of interest from the sample.

Alternatively viewed, step c) of the above method comprises heating the sample to inactivate the proteinase or enzymatically active fragment thereof, wherein
  i) the concentration of calcium in said sample is ≤about 80 μM and said sample is essentially free of EDTA; or
  ii) the concentration of monovalent salt in said sample is ≥about 20 mM Preferably, the sample is or comprises polyacrylamide gel comprising polypeptides, wherein the digestion of said polypeptides is desired for the production of small fragments for analysis by mass spectrometry. Thus, the present invention provides a method of preparing a protein fragment sample, preferably for mass spectrometry analysis, said method comprising a) contacting a sample comprising one or more polypeptides with a proteinase or an enzymatically active fragment thereof, said proteinase comprising the amino acid sequence of SEQ ID NO: 1 or comprising an amino acid sequence which is at least about 70% identical to SEQ ID NO: 1;

b) incubating the sample under conditions which permit at least partial digestion of polypeptides in the sample; and c) heating the sample to inactivate the proteinase or enzymatically active fragment thereof, wherein i) the concentration of free calcium in said sample is ≤about 80 μM; or ii) the concentration of monovalent salt in said sample is ≥about 20 mM; and d) optionally removing the biological molecule of interest from the sample.

Preferably, the sample is a polyacrylamide gel comprising one or more polypeptides.

Preferably, the sample to which the proteinase or enzymatically active fragment thereof is added comprises one or more further enzymes. Preferably said further enzyme is selected from the group consisting of a nuclease (preferably a deoxyribonuclease, an exonuclease, a Bal 31 nuclease, a ribonuclease, a mung bean nuclease or an S1 nuclease), a polymerase (preferably a DNA polymerase or an RNA polymerase), a reverse transcriptase, a ligase, (preferably a DNA ligase or an RNA ligase), a methylase, a transferase (preferably a polynucleotide adenylyl-transferase), a topisomerase, a guanylyl transferase, a phosphatase (preferably an alkaline phosphatase, preferably a thermolabile alkaline phosphatase, more preferably shrimp alkaline phosphatase), a kinase, a helicase, a restriction enzyme and a glycosylase. The sample preferably comprises combinations of such further enzymes. Preferably, the sample comprises a DNA polymerase or a reverse transcriptase. Preferably, such enzymes are exogenous enzymes, i.e. not expressed by the cells within the sample or the cells from which the cellular material in the sample is derived. The methods of the present invention provide advantageously mild proteinase inactivation conditions, which may be tolerated by such additional enzymes, thus such enzymes may be present during the proteinase inactivation step, thereby simplifying subsequent workflow.

As mentioned above, the gold-standard proteinase currently used in the field, Proteinase K, required inactivation at high temperatures which can damage enzymes or biological molecules of interest in the sample. If inactivation of Proteinase K is desired without heating at high temperatures, then the proteinase must be removed from the sample or the concentration of the enzyme must be substantially diluted. Such removal or dilution steps lengthen workflow; increase cost and can lead to loss or damage of material in the sample. They are particularly not suitable when small sample sizes are processed.

Preferably the sample to which the proteinase is added has a volume of ≤1000 μl, more preferably ≤500 μl, more preferably ≤300 μl, more preferably ≤250 μl, more preferably ≤200 μl, more preferably ≤150 μl, more preferably ≤100 μl, more preferably ≤75 μl, more preferably ≤50 μl. Alternatively, the sample is a microfluidic sample. Preferably the microfluidic sample has a volume of ≥0.01 μl. Preferably the microfluidic sample has a volume of ≤10 μl, preferably ≤5 μl more preferably ≤1 μl, more preferably ≤0.5 μl more preferably ≤0.1 μl.

Thus, preferably, any of the above methods comprise a step, subsequent to the inactivation step, which comprises the enzymatic catalysis of a substrate, wherein said subsequent step is performed without prior removal or dilution of the proteinase or enzymatically active fragment thereof.

By "without prior removal" is meant that the proteinase is not physically removed from the sample for instance by purification, extraction or centrifugation.

By "without prior dilution" is meant that the concentration of the proteinase in the sample is not significantly diluted, i.e. is not substantially inactivated by dilution. Definitions of substantially inactivated are as described elsewhere herein. Preferably, the concentration of the proteinase in the sample is not diluted more than 4 fold, more preferably not more than 3 fold, more preferably not more than 2 fold.

Preferably, the sample comprises one or more nucleic acid molecules, and the method comprises, subsequent to the inactivation step, a step of nuclease-mediated digestion of the nucleic acid molecules without prior removal or dilution of the proteinase or enzymatically active fragment thereof.

Preferably, the sample comprises one or more nucleic acid molecules and the method comprises, subsequent to the inactivation step, a step of phosphorylation or de-phosphorylation of the nucleic acid molecules without prior removal or dilution of the proteinase or enzymatically active fragment thereof.

Preferably, the sample comprises one or more nucleic acid molecules and the method comprises, subsequent to the inactivation step, a step of ligation of the nucleic acid molecules without prior removal or dilution of the proteinase or enzymatically active fragment thereof.

Preferably, the sample comprises one or more RNA molecules, and the method comprises, subsequent to the inactivation step, a step of reverse transcription without prior removal or dilution of the proteinase or enzymatically active fragment thereof.

Preferably, the sample comprises one or more nucleic acid molecules, and the method comprises, subsequent to the inactivation step, a step of nucleic acid polymerisation without prior removal or dilution of the proteinase or enzymatically active fragment thereof.

Preferably, the sample comprises one or more nucleic acid molecules, and the method comprises, subsequent to the inactivation step, a step of nucleic acid amplification without prior removal or dilution of the proteinase or enzymatically active fragment thereof.

Preferably, the sample comprises one or more nucleic acid molecules, and the method comprises, subsequent to the inactivation step, a step of nanopore sequencing without prior removal or dilution of the proteinase or enzymatically active fragment thereof.

Preferably, the sample comprises one or more virus particles or cells, preferably bacterial cells, and the method comprises, subsequent to the inactivation step, a step of cell lysis without prior removal or dilution of the proteinase or enzymatically active fragment thereof.

The invention will now be described by way of non-limiting Examples with reference to the following figures in which.

Figure 6:
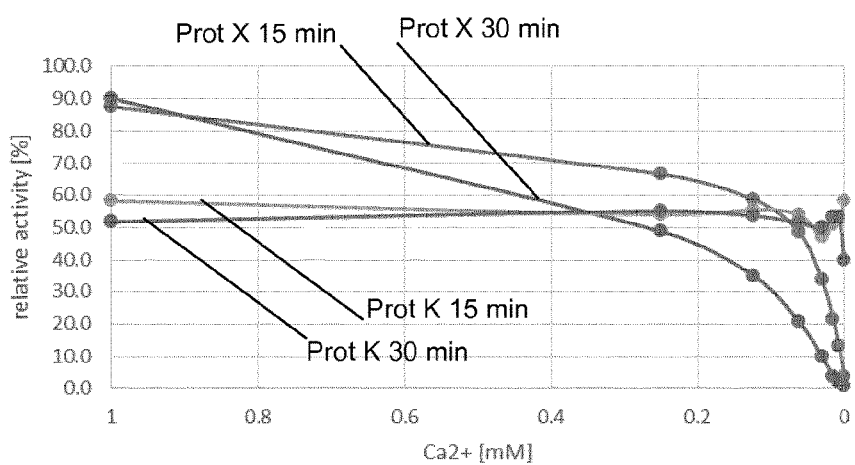

FIG. 6 shows the degree of inactivation of Proteinase X and Proteinase K after heating at 60° C. for 15 and 30 minutes in presence of varying free calcium concentrations. Activity is presented as % activity relative to maximum activity observed with the same proteinase in the same buffer (comprising 10 mM $CaCl_2$) kept on ice without heat-treatment.

Figure 7:
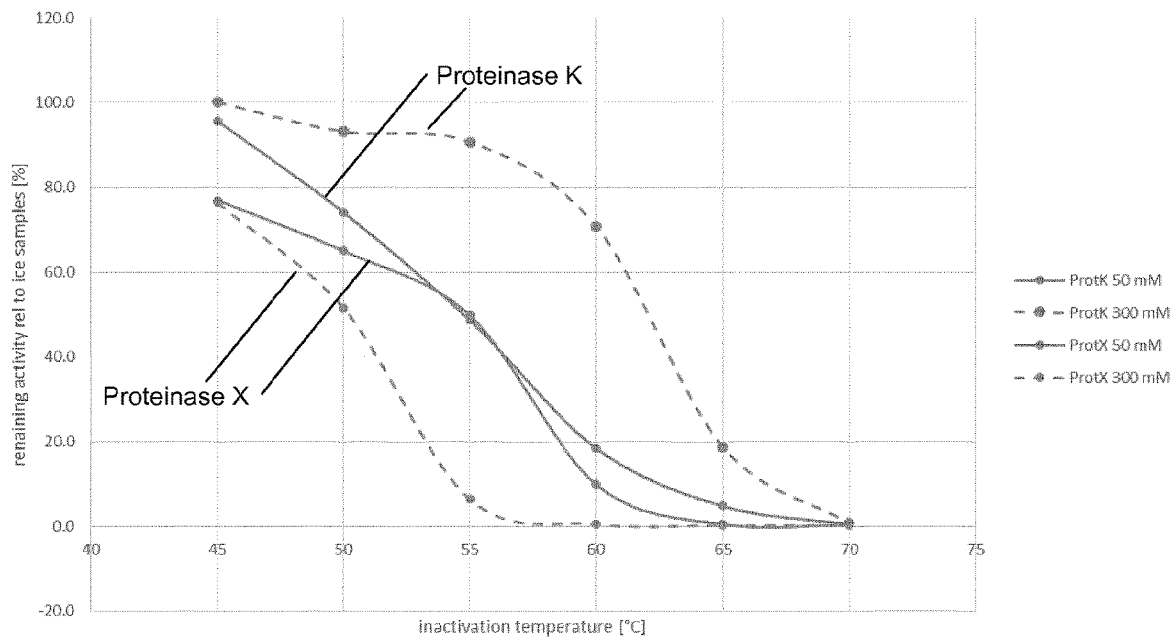

FIG. 7 shows the effect of NaCl concentration on the thermolability profiles of Proteinase X and Proteinase K. Incubation for 30 minutes at indicated temperatures in the absence of free calcium and in the presence of 50 mM or 300 mM NaCl. Activity is presented as % activity relative to maximum activity observed with the same proteinase in the same buffer (comprising 10 mM $CaCl_2$) kept on ice without heat-treatment.

Figure 8:
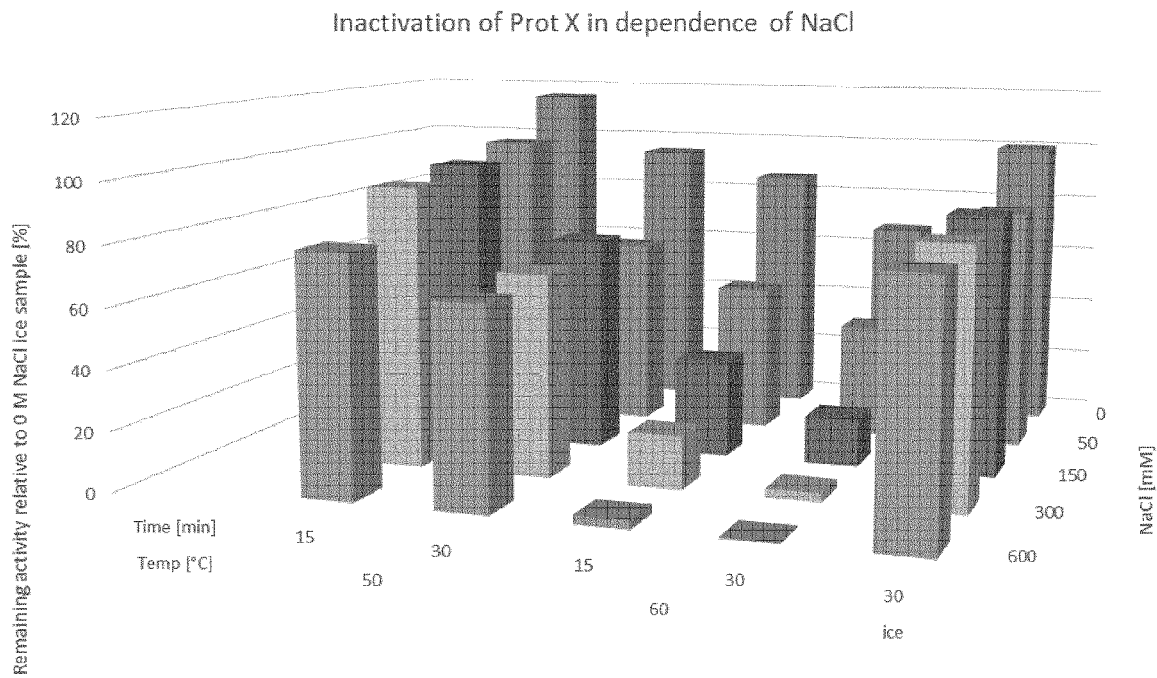

FIG. 8 shows the inactivation of Proteinase X at 50 and 60° C. in the presence of various concentrations of NaCl. Activity is presented as % activity relative to maximum activity observed with Proteinase X in the same buffer (comprising 0 M NaCl, 0.03 mM $CaCl_2$) kept on ice without heat-treatment.

Figure 9:
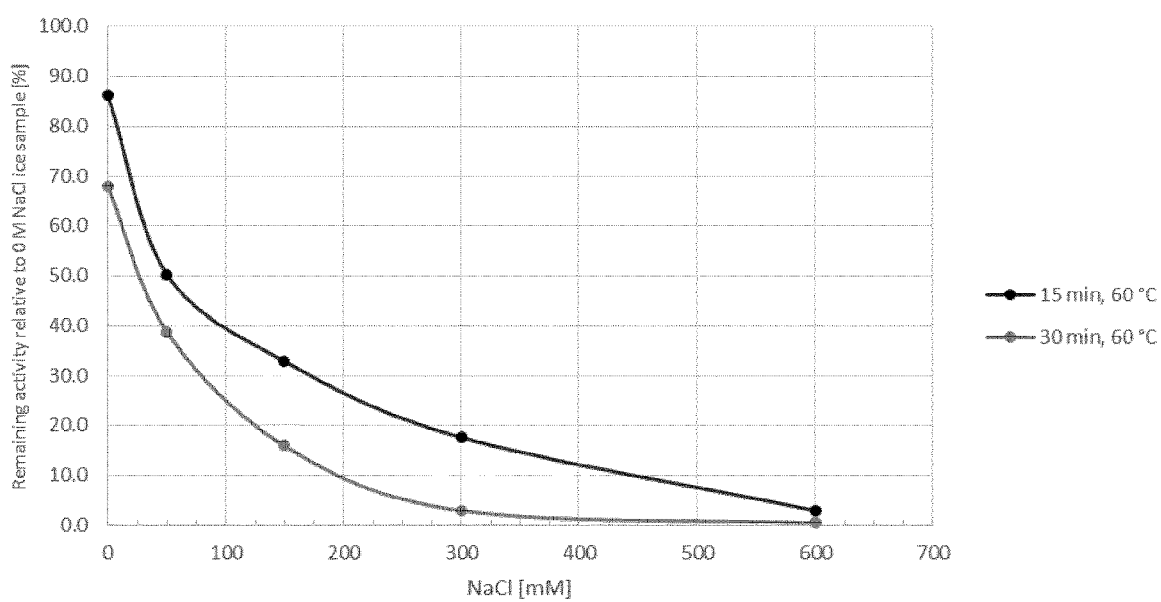

FIG. 9 shows the inactivation of Proteinase X at 60° C. in the presence of various concentrations of NaCl. Activity is presented as % activity relative to maximum activity observed with Proteinase X in the same buffer (comprising 0 M NaCl, 30 μM $CaCl_2$) kept on ice without heat-treatment.

EXAMPLES

Example 1: Proteinase Specific Activities

In all Examples, Proteinase K was purchased from Thermo Fischer (prod. No. EO0491, 28.9 kDa) and Proteinase X was produced recombinantly in *Pichia pastoris* at ArcticZymes (Batch 1602-1, SEQ ID NO: 1).

To determine the specific activity of the two proteinases (U per mg proteinase), proteinase concentrations in the solutions were first determined by using NanoDrop.

Nanodrop is a spectrophotometric approach to quantifying protein concentration through measuring absorbance at a wavelength of 280 nm.

Proteinase K was determined to be present at a concentration of 14.3 mg/ml. 10,000 fold stock dilutions (1.43 μg/ml) were used subsequently. Proteinase X was determined to be present at a concentration of 9.2 mg/ml. 1,000 fold stock dilutions (9.2 μg/ml) were used subsequently.

The activity of Proteinase X and K (in U/mL) was determined using a standard kinetic peptide-based assay. In a 1000 μl cuvette was provided 0.4 μg/ml Proteinase X or 0.06 μg/ml Proteinase K
1 mM substrate Suc-Ala-Ala-Pro-Phe-pNA
12 mM NaCl, 0.1 M Tris-HCl pH 8, 10 mM $CaCl_2$,
1% DMSO
Total volume 1000 μl Enzymatic cleavage of the substrate Suc-Ala-Ala-Pro-Phe-NA to 4-nitroaniline was assayed by measuring the increase in absorbance at 410 nm (EM 8.8) over two minutes using a UV-spectrophotometer (Ultrospec 2000, Pharmacia Biotec, Sweden) at 25° C. One Unit is defined as the amount of enzyme that produces one μmol 4-nitroaniline at 25° C. per minute.

The following specific activities were determined (Table 1).

TABLE 1

| Specific activity of Proteinase X and K | | | |
|---|---|---|---|
| | U/ml | mg/ml | Specific activity |
| Proteinase X | ~600 | 9.2 | ~65 (U/mg) |
| Proteinase K | ~5700 | 14.3 | ~400 (U/mg) |

The results were verified using a vial of Proteinase K from a different vendor (Sigma, 04850, measured to 400 U/mg).

Example 2: Effect of Free Calcium Concentration on Proteinase Activity

The activity of Proteinase X and K was determined at various temperatures using a standard peptide-based assay: In a 1.5 ml cuvette was provided 0.37 μg/ml Proteinase X or 0.06 μg/ml Proteinase K (equivalent to 24 mU/mL proteinase)
1 mM substrate Suc-Ala-Ala-Pro-Phe-pNA
12 mM NaCl, 0.1 M Tris-HCl, pH 8.0, 10 mM $CaCl_2$,
1% DMSO
Total volume 1000 μl The cuvette was incubated at the indicated temperature for the duration of the assay. Enzymatic cleavage of the substrate Suc-Ala-Ala-Pro-Phe-NA to 4-nitrolaniline was assayed by measuring the increase in absorbance at 410 nm (EM 8.8) over time for 30 seconds in 1.5 mL Semi-micro cuvettes (Brand, Germany) using a UV-spectrophotometer (Ultrospec 2000, Pharmacia Biotech, Sweden).

Activity was calculated as % relative activity compared to the maximum activity, which was observed at 65° C. Measurements above 65° C. were technically not possible. Prior art teaches that the temperature optima of both Proteinase X and K are located between 65 and 70° C.

Figure 1:
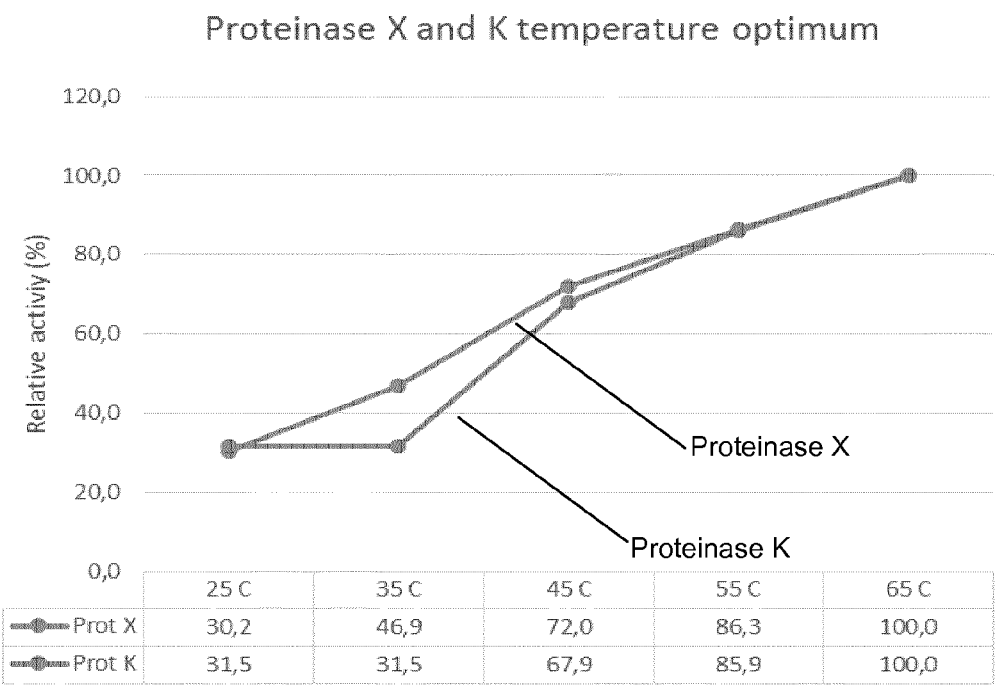
FIG. 1 shows the proteinase activity of Proteinase X and K at different temperatures. Activity is presented as % activity relative to maximum activity observed at 65° C. under standard assay conditions with 10 mM free Calcium.

As shown in FIG. 1, the two proteinases have similar temperature-activity profiles in the presence of 10 mM calcium.

Temperature-activity profiles of Proteinase X and K were also determined under low calcium (5 μM) and calcium free (0 μM) conditions. Again, 24 mU/mL proteinase (equivalent to 0.37 μg/ml Proteinase X or 0.06 μg/ml Proteinase K) was incubated with 1 mM substrate Suc-Ala-Ala-Pro-Phe-pNA at the indicated temperatures in buffer (0.1 M Tris-HCl, pH 8.0, 0 mM/0.005 mM/10 mM $CaCl_2$, 1% DMSO, 12 mM NaCl); total volume 1000 μl.

Enzymatic cleavage of the substrate Suc-Ala-Ala-Pro-Phe-NA to 4-nitrolaniline was assayed by measuring the increase in absorbance at 410 nm (EM 8.8) over time for 30 seconds using a UV-spectrophotometer.

Activity was calculated as % relative activity compared to the activity observed at 65° C. in the presence of 10 mM $CaCl_2$ (Table 2), as this was the highest activity observed.

TABLE 2

Activity of Proteinase X and K relative to activity at 10 mM calcium and 65° C. (%)

| | Prot X | | | | | Prot K | | | | |
|---|---|---|---|---|---|---|---|---|---|---|
| Temp (° C.) | 25 | 35 | 45 | 55 | 65 | 25 | 35 | 45 | 55 | 65 |
| 0 mM Ca | 29.7 | 47.0 | 65.1 | 81.8 | 82.6 | 29.4 | 29.4 | 64.1 | 78.0 | 90.1 |
| 0.005 mM Ca | 29.1 | 43.8 | 64.6 | 80.3 | 88.7 | 30.8 | 30.8 | 66.8 | 82.3 | 94.2 |
| 10 mM Ca | 30.2 | 46.9 | 72.0 | 86.3 | 100.0 | 31.5 | 31.5 | 67.9 | 85.9 | 100.0 |

At each calcium concentration, the temperature profiles for both proteinases are similar, with the maximum activity being observed at 65° C. Reduction of calcium concentration appeared to result in only a small reduction in proteinase activity at some temperatures. The activity profiles of the two proteinases differed when activity was considered relative to the activity achieved using 10 mM calcium at each specific temperature. The results are shown in Tables 3 and 4 and FIGS. 2 and 3, which highlight any calcium dependent effect on proteinase activity at different temperatures.

TABLE 3

Proteinase X activity relative to activity using 10 mM calcium at stated temperature.

| | 25° C. | 35° C. | 45° C. | 55° C. | 65° C. |
|---|---|---|---|---|---|
| 0 mM Ca | 98.2 | 100.0 | 90.4 | 94.8 | 82.6 |
| 0.005 mM Ca | 96.2 | 93.4 | 89.7 | 93.1 | 88.7 |
| 10 mM Ca | 100.0 | 100.0 | 100.0 | 100.0 | 100.0 |

TABLE 4

Proteinase K activity relative to activity using 10 mM calcium at stated temperature.

| | 25° C. | 35° C. | 45° C. | 55° C. | 65° C. |
|---|---|---|---|---|---|
| 0 mM Ca | 93.4 | 93.4 | 94.4 | 90.7 | 90.1 |
| 0.005 mM Ca | 97.6 | 97.6 | 98.4 | 95.8 | 94.2 |
| 10 mM Ca | 100.0 | 100.0 | 100.0 | 100.0 | 100.0 |

Figure 2:
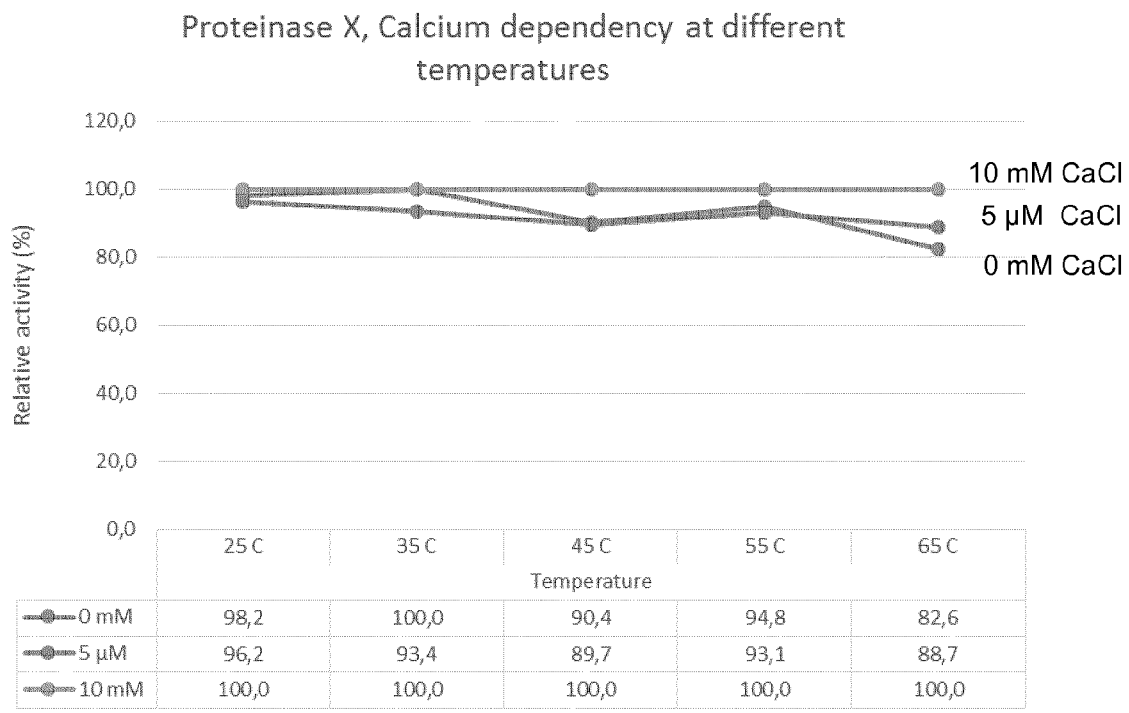
FIG. 2 shows the activity of Proteinase X at different temperatures with either 0 μM, 5 μM or 10 mM free calcium in the assay buffer. The results are presented relative (%) to the standard assay conditions at each temperature, which is 10 mM free calcium.

FIG. 2 and Table 3 show that for Proteinase X, a low calcium concentration or the absence of calcium results in some loss of activity (maximum decrease of <10%) at 55° C. and 45° C., with no discernible drop in activity at 25° C. or 35° C. A decrease in activity of approximately 20% was observed at 65° C. in the absence of calcium, and a decrease of approximately 10% was observed at 65° C. in low calcium (0.005 mM).

Figure 3:
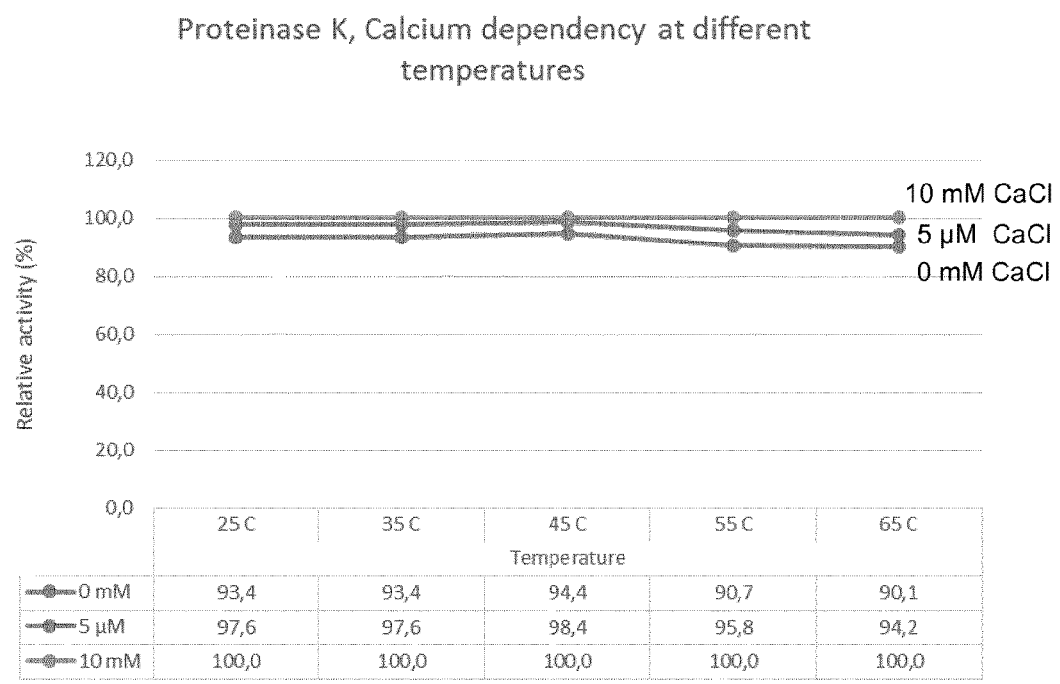
FIG. 3 shows the activity of Proteinase K at different temperatures with either 0 μM, 5 μM or 10 mM free calcium in the assay buffer. The results are presented relative (%) to the standard assay conditions at each temperature, which is 10 mM free calcium.

In contrast, FIG. 3 and Table 4, show that the activity of Proteinase K at each temperature was largely unaffected by the calcium conditions, i.e. whether in the presence of high calcium concentrations, low calcium concentrations or in the absence of calcium, only a minimal degree of change in activity was observed with increasing temperature.

Together, the data suggest that low calcium concentrations could induce heat-inactivation of Proteinase X to a larger extent than Proteinase K.

Example 3: $Ca^{2+}$ Dependent Inducible Thermolability of Proteinases

The calcium-dependent thermolability of Proteinases X and K was investigated further.

Heat-Treatment Steps:

The proteinases were incubated at 60° C. for 15 or 30 minutes in a PCR thermo cycler (Veriti, Applied Biosystems) in buffers comprising various different concentrations of free calcium. Buffers comprised 0.1 mg/ml proteinase X (equivalent to 6.5 U/ml Proteinase X initial activity) or 0.014 mg/ml Proteinase K (equivalent to 5.6 U/ml Proteinase K initial activity)

0.025 M Tris-HCl, pH8, 300 mM NaCl, $CaCl_2$ (1 mM/0.25 mM/0.125 mM/0.063 mM/0.031 mM/0.016 mM/0.008 mM/0 mM)

volume: 50 µl.

After inactivation the samples were placed back on ice. Samples used as controls were kept on ice throughout.

Assay of Remaining Activity

After the heat-treatment steps, samples were diluted 1:10 in 0.025 M Tris-HCl, pH8, 300 mM NaCl. The dilution step was performed to reduce enzyme activity U/ml in the samples to bring them within the range that is detectable in a reaction assay.

The remaining activity of the proteinases was assessed as follows:

0.4 µg/ml Proteinase X or 0.06 µg/ml Proteinase K (equivalent to 26 and 24 mU/ml initial activity, respectively) was incubated with 1 mM substrate Suc-Ala-Ala-Pro-Phe-pNA at 37° C. in standard reaction buffer (0.1 M Tris-HCl, pH 8.0, 10 mM $CaCl_2$, 1% DMSO, 12 mM NaCl); total volume 250 µl.

Enzymatic cleavage of the substrate Suc-Ala-Ala-Pro-Phe-NA to 4-nitrolaniline was assayed by measuring the increase in absorbance at 405 nm (EM 8.8) over time for 10 minutes with signal detection every 11 seconds using a multi-mode platereader (Synergy H1, BioTek, USA).

Figure 4:
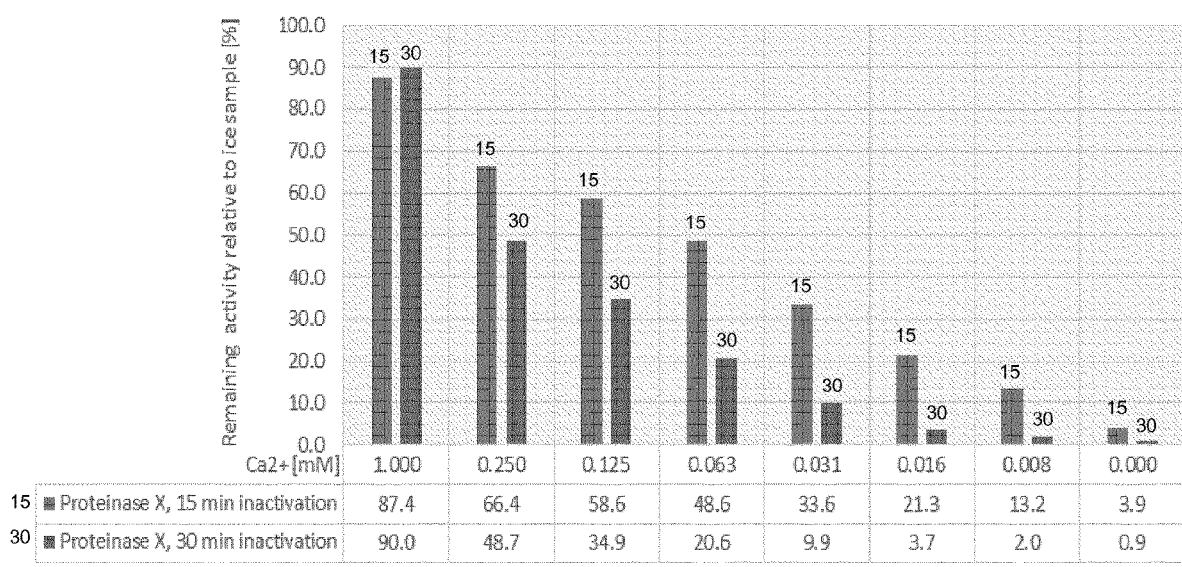
FIG. 4 shows the degree of inactivation of Proteinase X after heating at 60° C. for 15 and 30 minutes in the presence of different free calcium concentrations. Activity is presented as % remaining activity, i.e. relative to control (kept on ice, no heating step).
Figure 5:
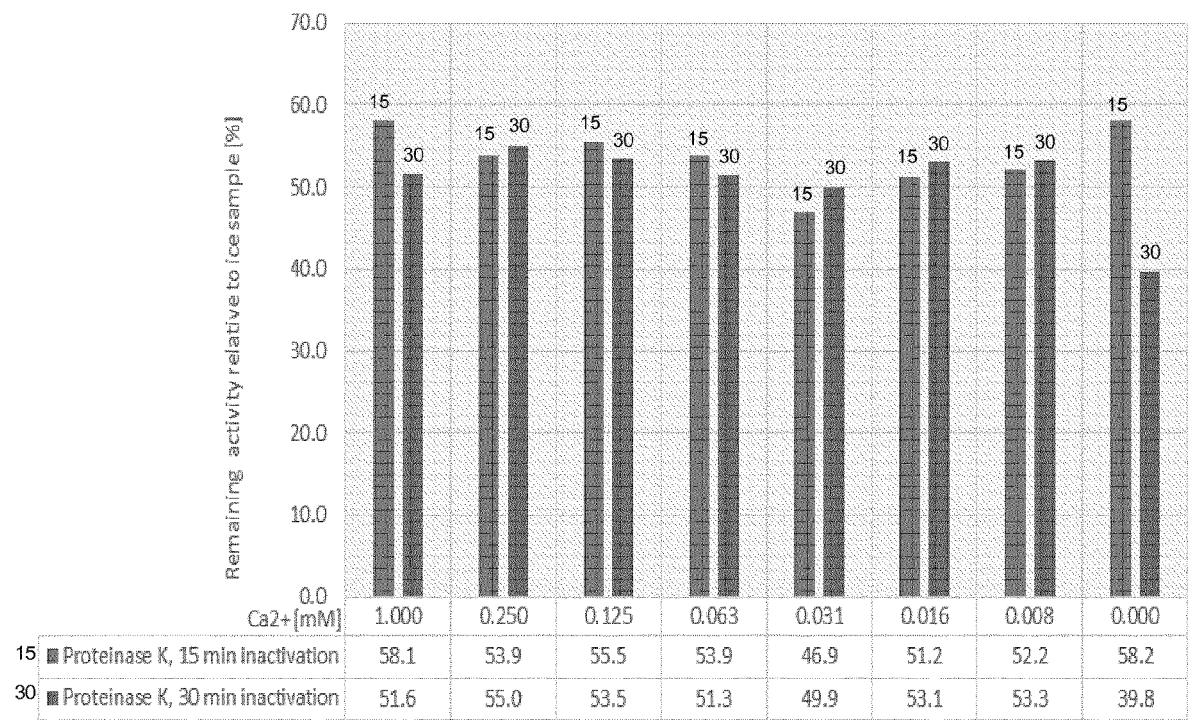
FIG. 5 shows the degree of inactivation of Proteinase K after heating at 60° C. for 15 and 30 minutes in the presence of different free calcium concentrations. Activity is presented as % remaining activity, i.e. relative to control (kept on ice, no heating step).

The results are shown in FIGS. 4 and 5. Activity is displayed as percentage remaining activity as compared to control sample (same proteinase and buffer, kept on ice not exposed to heating step).

As shown in FIG. 5, decreasing free calcium concentration does not affect heat-inactivation of Proteinase K, which loses approximately 40% activity in all samples incubated at 60° C. independent of the free $Ca^{2+}$-concentration. Substantial inactivation (≥75%) of Proteinase K was not achieved under any conditions.

In contrast, as shown in FIG. 4, decreasing the free calcium concentration led to increased thermolability of Proteinase X. Substantial inactivation (≥75%, i.e. less than 25% remaining activity) was achieved by heating at 60° C. for 30 minutes at free calcium concentrations ≤0.063 mM, and by heating at 60° C. for 15 minutes at free calcium concentrations ≤0.016 mM. ≥90% inactivation is preferred, and this was achieved with Proteinase X by heating at 60° C. for 30 minutes at free calcium concentrations ≤0.031 mM, or for 15 in the absence of free calcium.

Thus, proteinase X is inducibly thermolabile in the presence of low calcium concentrations, whereas the thermolability of proteinase K is unaffected by calcium concentration.

This difference is demonstrated further in FIG. 6, which shows the inactivation profiles of the two proteinases after heating at 60° C. for 15/30 minutes at various calcium concentrations.

Example 4: Free Calcium Dependent Inactivation Profile of Proteinases

The effect of differing heat-treatment steps on the inactivation of Proteinases X and K was assessed. In the following experiment an upper free calcium limit of 5 µM was used and the heat-inactivation step was performed over a range of temperatures and heating times.

Heat-Treatment Steps:

The proteinases were incubated at various temperatures (45° C., 50° C., 55° C., 60° C., 65° c. and 70° C.) for various times (2, 5, 10, 15, 30 60 minutes) in buffers comprising various different concentrations of free calcium (CaCl$_2$, 0 µM, 2.5 µM or 5 µM). Buffers further comprised 0.1 mg/ml (6.5 U/ml initial activity) Proteinase X or 0.016 mg/ml (6.4 U/ml initial activity) Proteinase K, 25 mM HEPES, pH 8, 100 mM NaCl, total volume: 50 µl.

Proteinase K was dialysed against a Ca-free storage buffer before use to remove free calcium therein. After inactivation the samples were placed back on ice. Samples used as controls were kept on ice throughout.

Assay of Remaining Activity

After the heat-treatment steps, samples were diluted 1:20 in 50 mM HEPES, pH8, 100 mM NaCl. The dilution step was performed to reduce enzyme activity U/ml in the samples to bring them within the range that is detectable in a reaction assay.

The remaining activity of the proteinases was assessed as follows:

0.2 µg/ml Proteinase X or 0.03 µg/ml Proteinase K (equivalent to 13 mU and 12 mU initial activity, respectively), was incubated with 1 mM substrate Suc-Ala-Ala-Pro-Phe-pNA at 37° C. in standard reaction buffer (0.1 M Tris-HCl, pH 8.0, 10 mM CaCl$_2$, 1% DMSO, 4 mM NaCl); total volume 250 µl.

Enzymatic cleavage of the substrate Suc-Ala-Ala-Pro-Phe-NA to 4-nitrolaniline was assayed by measuring the increase in absorbance at 405 nm (EM 8.8) over time for 10 minutes with signal detection every 11 seconds using a multi-mode platereader (Synergy H1, BioTek, USA). Remaining activity is as compared to the control sample kept on ice but otherwise identical to the tested samples.

The results are shown in Tables 5 to 7.

The above data demonstrates that in the absence of free calcium, ≥approximately 75% inactivation of Proteinase X is achieved:

within 2 minutes when heating at at least 70° C.;
within 5 minutes when heating at at least 65° C.;
within 10 minutes when heating at at least 60° C.; and
within 60 minutes when heating at at least 55° C.

And that ≥approximately 90% inactivation of Proteinase X is achieved within 2 minutes when heating at at least 70° C.;
within 5 minutes when heating at at least 65° C.;
within 15 minutes when heating at at least 60° C.; and
within 60 minutes when heating at at least 55° C.

TABLE 6

Remaining Activity: Proteinase X, 2.5 µM CaCl$_2$

| | Inactivation Temperature | 45° C. | 50° C. | 55° C. | 60° C. | 65° C. | 70° C. |
|---|---|---|---|---|---|---|---|
| Inactivation Time | 2 min | | | Absorbance Detection Problems | | | |
| | 5 min | 117.0 | 107.8 | 83.3 | 55.7 | 14.1 | 1.5 |
| | 10 min | 97.5 | 94.2 | 58.5 | 29.3 | 2.3 | 1.2 |
| | 15 min | 108.4 | 83.8 | 59.8 | 17.9 | 1.3 | 1.2 |
| | 30 min | 98.7 | 76.5 | 37.6 | 4.1 | 0.8 | 0.9 |
| | 60 min | 81.2 | 62.9 | 15.9 | 1.6 | 0.4 | 0.8 |
| | Ice | 100.0 | | | | | |
| Half life [min] | | — | >60 | <30 | 5 | <5 | <5 |
| 75% inactivation [min] | | — | — | <60 | <15 | <5 | <5 |
| 90% inactivation [min] | | | | 60 | <30 | <10 | <5 |

The above data demonstrates that at free calcium concentrations below 2.5 µM, ≥approximately 75% inactivation of Proteinase X is achieved:

within 5 minutes when heating at at least 70° C.;
within 5 minutes when heating at at least 65° C.;
within 15 minutes when heating at at least 60° C.; and
within 60 minutes when heating at at least 55° C.

And that ≥approximately 90% inactivation of Proteinase X is achieved:

within 5 minutes when heating at at least 70° C.;
within 10 minutes when heating at at least 65° C.; and
within 30 minutes when heating at at least 60° C.

TABLE 5

Remaining Activity (Percent): Proteinase X, 0 µM CaCl$_2$

| | Inactivation Temperature | 45° C. | 50° C. | 55° C. | 60° C. | 65° C. | 70° C. |
|---|---|---|---|---|---|---|---|
| Inactivation Time | 2 min | 110.7 | 107.6 | 98.4 | 83.8 | 42.1 | 6.7 |
| | 5 min | 101.6 | 83.8 | 80.4 | 46.3 | 8.3 | 1.6 |
| | 10 min | 95.9 | 76.2 | 63.6 | 23.3 | 1.8 | 1.5 |
| | 15 min | 94.0 | 78.2 | 49.7 | 11.3 | 1.2 | 1.0 |
| | 30 min | 88.2 | 70.8 | 29.7 | 2.4 | 1.0 | 1.0 |
| | 60 min | 71.1 | 49.3 | 11.2 | 0.7 | 1.1 | 0.9 |
| | Ice | 100.0 | | | | | |
| Half life [min] | | — | 60 | 15 | 5 | <2 | <2 |
| 75% inactivation [min] | | | | <60 | <10 | <5 | <2 |
| 90% inactivation [min] | | | | 60 | 15 | <5 | <2 |

TABLE 7

Remaining Activity: Proteinase X, 5 µM CaCl$_2$

| | Inactivation Temperature | 45° C. | 50° C. | 55° C. | 60° C. | 65° C. | 70° C. |
|---|---|---|---|---|---|---|---|
| Inactivation Time | 2 min | | | Absorbance Detection Problems | | | |
| | 5 min | 119.3 | 100.7 | 93.2 | 59.9 | 17.0 | 1.2 |
| | 10 min | 104.7 | 86.3 | 90.8 | 37.1 | 3.2 | 0.6 |
| | 15 min | 90.5 | 81.3 | 71.8 | 21.9 | 1.3 | 0.9 |
| | 30 min | 104.1 | 66.1 | 46.5 | 5.6 | 1.0 | 0.2 |
| | 60 min | 96.3 | 60.9 | 21.8 | 0.9 | 1.0 | 1.1 |
| | Ice | 100.0 | | | | | |
| Half life [min] | | — | >60 | 30 | <10 | <2 | <5 |
| 75% inactivation [min] | | — | — | <60 | <15 | <5 | <5 |
| 90% inactivation [min] | | | | >60 | <30 | <10 | <5 |

The above data demonstrates that at free calcium concentrations below 5 µM, approximately 75% inactivation of Proteinase X is achieved:
within 5 minutes when heating at at least 70° C.;
within 5 minutes when heating at at least 65° C.;
within 15 minutes when heating at at least 60° C.; and
within 60 minutes when heating at at least 55° C.

And that ≥approximately 90% inactivation of Proteinase X is achieved:
within 5 minutes when heating at at least 70° C.;
within 10 minutes when heating at at least 65° C.; and
within 30 minutes when heating at at least 60° C.

Thus, at free calcium concentrations ≤5 µM, incubation at 70° C. achieved ≥95% inactivation of Proteinase X within 5 minutes, and incubation at 65° C. achieved ≥95% inactivation of Proteinase X within 10 minutes (within 5 minutes in the absence of free calcium).

In presence of both 2.5 and 5 µM free calcium, incubation at 60° C. achieved ≥90% inactivation of Proteinase X within 30 minutes (within 15 in the absence of free calcium).

Incubation at ≥55° C. for 60 minutes achieved 80% inactivation of Proteinase X in the presence of 5 µM free calcium, 85% inactivation in the presence of ≤2.5 µM free calcium and about 90% inactivation in the absence of free calcium.

The same studies were performed using Proteinase K for comparison. The results are shown in Tables 8 to 10 below.

TABLE 8

Remaining Activity: Proteinase K, 0 µM CaCl$_2$

| | Inactivation Temperature | 45° C. | 50° C. | 55° C. | 60° C. | 65° C. | 70° C. |
|---|---|---|---|---|---|---|---|
| Inactivation Time | 2 min | 77.8 | 61.0 | 108.5 | 86.3 | 47.6 | 8.4 |
| | 5 min | 92.6 | 76.1 | 92.1 | 68.4 | 31.0 | 0.2 |
| | 10 min | 96.8 | 86.1 | 87.7 | 55.6 | 8.5 | 0.1 |
| | 15 min | 83.1 | 88.1 | 80.8 | 42.9 | 2.7 | −0.1 |
| | 30 min | 85.9 | 90.0 | 61.0 | 15.9 | 0.3 | −0.1 |
| | 60 min | 84.0 | 61.4 | 19.6 | 1.7 | 0.2 | 0.1 |
| | Ice | 100 | | | | | |
| Half life [min] | | — | >60 | <60 | 10 | 2 | <2 |
| 75% inactivation [min] | | — | — | <60 | <30 | <10 | <2 |
| 90% inactivation [min] | | | | >60 | <60 | <10 | <2 |

The above data demonstrates that in the absence of free calcium, ≥approximately 75% inactivation of Proteinase K is achieved:
within 2 minutes when heating at at least 70° C.;
within 10 minutes when heating at at least 65° C. (within 5 minutes for Prot X);
within 30 minutes when heating at at least 60° C. (within 10 minutes for Prot X); and
within 60 minutes when heating at at least 55° C. (less inactivation than with Prot X).

And that ≥approximately 90% inactivation of Proteinase K is achieved:
within 2 minutes when heating at at least 70° C.;
within 10 minutes when heating at at least 65° C. (within 5 minutes for Prot X); and
within 60 minutes when heating at at least 60° C. (within 15 minutes for Prot X).

TABLE 9

Remaining Activity: Proteinase K, 2.5 µM CaCl$_2$

| | Inactivation Temperature | 45° C. | 50° C. | 55° C. | 60° C. | 65° C. | 70° C. |
|---|---|---|---|---|---|---|---|
| Inactivation Time | 5 min | 102.1 | 101.7 | 100.0 | 76.3 | 40.1 | 0.4 |
| | 10 min | 96.2 | 97.3 | 86.2 | 60.3 | 14.3 | 3.3 |
| | 15 min | 100.9 | 94.3 | 78.4 | 45.3 | 4.7 | 0.2 |
| | 30 min | 94.5 | 80.9 | 53.7 | 16.9 | 0.6 | 0.3 |
| | 60 min | 79.8 | 61.5 | 18.4 | 1.9 | 0.3 | 0.3 |
| | Ice | 100 | | | | | |
| Half life [min] | | — | >60 | 30 | <15 | <5 | <5 |
| 75% inactivation [min] | | — | — | <60 | <30 | <10 | <5 |
| 90% inactivation [min] | | | | >60 | <60 | <15 | <5 |

The above data demonstrates that at free calcium concentrations below 2.5 µM, ≥approximately 75% inactivation of Proteinase K is achieved:
within 5 minutes when heating at at least 70° C.;
within 10 minutes when heating at at least 65° C. (within 5 minutes for Prot X);
within 30 minutes when heating at at least 60° C. (within 15 minutes for Prot X); and
within 60 minutes when heating at at least 55° C. (less inactivation than with Prot X).

And that ≥approximately 90% inactivation of Proteinase K is achieved:
within 5 minutes when heating at at least 70° C.;
within 15 minutes when heating at at least 65° C. (within 10 minutes for Prot X); and
within 60 minutes when heating at at least 60° C. (within 30 minutes for Prot X).

TABLE 10

Remaining Activity: Proteinase K, 5 µM CaCl$_2$

| | Inactivation Temperature | 45° C. | 50° C. | 55° C. | 60° C. | 65° C. | 70° C. |
|---|---|---|---|---|---|---|---|
| Inactivation Time | 5 min | 112.4 | 102.7 | 106.4 | 95.9 | 55.9 | 0.7 |
| | 10 min | 110.5 | 99.9 | 99.5 | 65.4 | 13.2 | 0.5 |
| | 15 min | 106.1 | 103.5 | 97.6 | 60.0 | 8.9 | 0.0 |
| | 30 min | 94.5 | 92.4 | 65.3 | 22.3 | 1.0 | 0.2 |
| | 60 min | 84.8 | 58.5 | 19.8 | 2.5 | 0.0 | −0.2 |
| | Ice | 100 | | | | | |
| Half life [min] | | — | >60 | <60 | <30 | 5 | <5 |
| 75% inactivation [min] | | — | — | <60 | <30 | <10 | <5 |
| 90% inactivation [min] | | | | >60 | <60 | <15 | <5 |

The above data demonstrates that at free calcium concentrations below 5 µM, ≥approximately 75% inactivation of Proteinase K is achieved:
within 5 minutes when heating at at least 70° C.;
within 10 minutes when heating at at least 65° C. (within 5 minutes for Prot X);
within 30 minutes when heating at at least 60° C. (within 15 minutes for Prot X); and
within 60 minutes when heating at at least 55° C.

And that ≥approximately 90% inactivation of Proteinase K is achieved with the following heating steps:
within 5 minutes when heating at at least 70° C.;
within 15 minutes when heating at at least 65° C. (within 10 minutes for Prot X); and within 60 minutes when heating at at least 60° C. (within 30 minutes for Prot X).

Thus, the results show that at all free calcium concentrations, the required heating times to achieve the same degree of inactivation at a given temperature are substantially lower for Proteinase X than Proteinase K. Alternatively viewed, at the vast majority of heating times and temperatures tested, greater inactivation of Proteinase X than Proteinase K is achieved. This is due to the observed thermolability of Proteinase X being induced at low calcium concentrations, which is not observed for Proteinase K.

Thus, the effect of calcium on the ability of proteinase K to be inactivated by heat treatment is significantly less marked than the effect on Proteinase X.

Example 5: Monovalent Salt-Dependent Inducible Thermolability of Proteinases To determine the effect of NaCl on the thermolability of Proteinases X and K, the inactivation profiles of both proteinases were determined at various temperatures in solutions comprising i) 50 mM (low salt conditions) or ii) 300 mM NaCl (high salt conditions).

Heat-Treatment Steps:

The proteinases were incubated at various temperatures (45° C., 50° C., 55° C., 60° C., 65° c. and 70° C.) for 30 minutes in buffers comprising 50 mM or 300 mM NaCl. Buffers comprised 0.1 mg/ml proteinase (equivalent to 6.5 U/ml Proteinase X or 40 U/ml Proteinase K), 25 mM HEPES, pH 8, 0 µM $CaCl_2$; volume: 50 µl.

After inactivation the samples were placed back on ice. Samples used as controls were kept on ice throughout.

Assay of Remaining Activity

After the heat-treatment steps, samples were diluted 1:10 or 1:100 for Proteinase X or Proteinase K, respectively, in 50 mM HEPES, pH8, 300 mM NaCl. The remaining activity of the proteinases was assessed as follows:

0.4 µg/ml Proteinase X (equivalent to initial activity of 26 mU/ml) or 0.04 µg/ml Proteinase K (equivalent to initial activity of 16 mU/ml) was incubated with 1 mM substrate Suc-Ala-Ala-Pro-Phe-pNA at 37° C. in standard reaction buffer (0.1 M Tris-HCl, pH 8.0, 10 mM $CaCl_2$, 1% DMSO, 12 mM NaCl); total volume 250 µl.

Enzymatic cleavage of the substrate Suc-Ala-Ala-Pro-Phe-NA to 4-nitrolaniline was assayed by measuring the increase in absorbance at 405 nm (EM 8.8) over time for 10 minutes with signal detection every 11 seconds using a multi-mode platereader (Synergy H1, BioTek, USA). Remaining activity is as compared to the control sample kept on ice but otherwise identical to the tested samples.

As shown in FIG. 7, increasing NaCl concentration has an opposite effect on the thermolability of ProtX as compared to ProtK. High NaCl concentrations stabilizes Proteinase K at high temperatures, whereas high NaCl concentrations induces thermolability of Proteinase X.

This result is particularly surprising. The proteinase X of SEQ ID NO: 1 was obtained from a salt water organism, and so would ordinarily be expected to tolerate high salt conditions. In contrast, Prot K is obtained from a non-marine source, the fungus Engyodontium album (formerly Tritirachium album) and would not be expected to be stabilised by high salt conditions.

Example 6: Monovalent Salt-Dependent Thermolability Profiles of Proteinases

To investigate further the effect of NaCl on the thermolability of Proteinase X, a wider range of NaCl concentrations to that used in Example 5 was assessed.

Heat-Treatment Steps:

Proteinase X was incubated at 50° C. or 60° C. for 15 or 30 minutes in buffers comprising 0, 50, 150, 300 or 600 mM NaCl. Buffers comprised 0.1 mg/ml proteinase X (equivalent to 6.5 U/ml), 25 mM HEPES, pH 8, 0.03 mM $CaCl_2$, volume: 50 µl.

After inactivation the samples were placed back on ice. Samples used as controls were kept on ice throughout.

Assay of Remaining Activity

After the heat-treatment steps, samples were diluted 1:10 in 50 mM HEPES, pH 8, 300 mM NaCl. The remaining activity of the proteinases was assessed as follows:

0.4 µg/ml Proteinase X (equivalent to 26 mU/ml initial activity), was incubated with 1 mM substrate Suc-Ala-Ala-Pro-Phe-pNA at 37° C. in standard reaction buffer (0.1 M Tris-HCl, pH 8.0, 10 mM $CaCl_2$, 1% DMSO, 12 mM NaCl); total volume 250 µl.

Enzymatic cleavage of the substrate Suc-Ala-Ala-Pro-Phe-NA to 4-nitrolaniline was assayed by measuring the increase in absorbance at 405 nm (EM 8.8) over time for 10 minutes with signal detection every 11 seconds using a multi-mode platereader (Synergy H1, BioTek, USA). Remaining activity is as compared to the control sample kept on ice but otherwise identical to the tested samples.

The results are shown in FIG. 8 and Table 11.

TABLE 11

| NaCl-dependent effect on thermolability of Proteinase X | | | | | |
|---|---|---|---|---|---|
| Inactivation Temp | | 50° C. | | 60° C. | Ice |
| Inactivation Time | | 15 min | 30 min | 15 min | 30 min | 30 min |
| NaCl conc. | 600 mM | 79.5 | 66.1 | 2.9 | 0.4 | 82.3 |
| | 300 mM | 94.2 | 67.8 | 17.6 | 2.9 | 84.0 |
| | 150 mM | 97.0 | 72.3 | 32.9 | 15.9 | 86.5 |
| | 50 mM | 101.0 | 64.2 | 50.3 | 38.7 | 81.7 |
| | 0 mM | 115.7 | 94.9 | 86.2 | 67.9 | 100 |

The above data demonstrates that at NaCl concentrations 150 mM, ≥approximately 80% inactivation of Proteinase X is achieved by heating at 60° C. within 30 minutes.

The above data also demonstrates that at NaCl concentrations ≥300 mM, ≥approximately 95% inactivation of Proteinase X is achieved by heating at 60° C. within 30 minutes and ≥approximately 80% inactivation of Proteinase X is achieved by heating at 60° C. within 150 minutes.

A plot of NaCl conc. (x-axis) vs. remaining activity after heating at 60° C. for 30/15 minutes (y-axis), FIG. 9, demonstrates that substantial inactivation (≥75%) is achieved by heating at 60° C. for 15 minutes with an NaCl concentration of at least about 210 mM, and heating for 30 minutes with an NaCl concentration of at least about 100 mM.

Example 7: Combined Effect of Free Calcium and Monovalent Salt Concentrations on Thermolability of Proteinases The above studies demonstrate that i) lowering the concentration of free calcium or ii) raising the concentration of NaCl induces thermolability of Proteinase X to a greater extent than Proteinase K. The combined effect of these conditions was subsequently investigated.

Heat-Treatment Steps:

Proteinases X and K were incubated at 60° C. for 30 minutes in buffers comprising varying concentrations of NaCl (0, 25, 50, 75, 100, 125 mM) and free calcium (0, 5, 10, 20 and 20 µM $CaCl_2$). Buffers comprised 6.5 U/ml Proteinase X or 6.4 U/ml Proteinase K (equivalent to 0.1 mg/ml Proteinase X or 0.016 mg/ml Proteinase K), 25 mM HEPES, pH 8 volume: 50 µl.

Proteinase K was dialysed against a Ca-free storage buffer before use to remove free calcium therein After inactivation the samples were placed back on ice. Samples used as controls were kept on ice throughout.

Assay of Remaining Activity

After the heat-treatment steps, samples were diluted 1:20 in 50 mM HEPES, pH 8, 100 mM NaCl. The remaining activity of the proteinases was assessed as follows:

0.2 µg/ml Proteinase X (equivalent to 13 mU/ml initial activity) or 0.03 µg/ml Proteinase K (equivalent to 12 mU/ml initial activity), was incubated with 1 mM substrate Suc-Ala-Ala-Pro-Phe-pNA at 37° C. in standard reaction buffer (0.1 M Tris-HCl, pH 8.0, 10 mM $CaCl_2$, 1% DMSO, 4 mM NaCl); total volume 250 µl.

Enzymatic cleavage of the substrate Suc-Ala-Ala-Pro-Phe-NA to 4-nitrolaniline was assayed by measuring the increase in absorbance at 405 nm (EM 8.8) over time for 10 minutes with signal detection every 11 seconds using a multi-mode platereader (Synergy H1, BioTek, USA). Remaining activity is as compared to the control sample kept on ice but otherwise identical to the tested samples.

The results are shown in Tables 12 and 13

TABLE 12

Combined effect of $CaCl_2$ and NaCl on Proteinase X thermolability.

| NaCl | $CaCl_2$ | | | | |
|---|---|---|---|---|---|
| | 0 µM | 5 µM | 10 µM | 20 µM | 30 µM |
| 0 mM | 35.0 | 51.3 | 43.4 | 59.0 | 54.9 |
| 25 mM | 20.0 | 31.3 | 35.0 | 42.2 | 44.2 |
| 50 mM | 12.2 | 20.5 | 22.4 | 32.3 | 39.7 |
| 75 mM | 4.8 | 12.6 | 15.5 | 25.0 | 32.6 |
| 100 mM | 2.8 | 8.0 | 10.8 | 19.2 | 22.8 |
| 125 mM | 1.9 | 4.5 | 6.6 | 13.3 | 16.8 |

Substantial inactivation (75%) was achieved at all free calcium concentrations in the presence of ≥100 mM NaCl.

Additionally, substantial inactivation (≥about 75%) was achieved with a maximum free calcium concentration of 20 µM in the presence of at least 75 mM NaCl.

Additionally, substantial inactivation (≥about 75%) was achieved with a maximum free calcium concentration of 10 µM in the presence of at least 50 mM NaCl.

Additionally, substantial inactivation (≥about 75%) was achieved with a maximum free calcium concentration of 5 µM in the presence of at least 50 mM NaCl.

Additionally, substantial inactivation (≥about 75%) was achieved in the absence of free calcium and in the presence of at least 25 mM NaCl.

Superior inactivation (≥about 90%) was achieved with a maximum free calcium concentration of 20 µM in the presence of at least 125 mM NaCl.

Superior inactivation (≥about 90%) was achieved with a maximum free calcium concentration of 10 µM in the presence of at least 100 mM NaCl.

Superior inactivation (≥about 90%) was achieved with a maximum free calcium concentration of 5 µM in the presence of at least 75 mM NaCl.

In the absence of free calcium, superior inactivation (≥about 90%) was achieved in the presence of at least 50 mM NaCl.

TABLE 13

Combined effect of $CaCl_2$ and NaCl on Proteinase K thermolability.

| NaCl | $CaCl_2$ | | | | |
|---|---|---|---|---|---|
| | 0 µM | 5 µM | 10 µM | 20 µM | 30 µM |
| 0 mM | 2.3 | 5.7 | 6.4 | 8.9 | 8.4 |
| 25 mM | 4.8 | 8.4 | 9.4 | 11.0 | 10.7 |
| 50 mm | 10.4 | 13.6 | 15.5 | 20.6 | 15.5 |
| 75 mm | 14.1 | 22.9 | 23.7 | 28.3 | 27.2 |
| 100 mM | 20.2 | 24.8 | 31.3 | 36.9 | 34.0 |
| 125 mM | 31.6 | 36.5 | 42.6 | 44.8 | 43.7 |

The results demonstrate that Proteinase K has a very different thermolability profile to Proteinase X. Proteinase K becomes increasingly thermolabile under low salt conditions, is stabilised under high salt conditions and is largely unaffected by calcium concentration. Proteinase X on the other hand becomes increasingly thermolabile under high salt conditions and low free calcium conditions.

---

The invention claimed is:

1. A method of inactivating a proteinase or an enzymatically active fragment thereof in a sample, said proteinase comprising the amino acid sequence of SEQ ID NO: 1 or comprising an amino acid sequence which is at least about 90% identical to SEQ ID NO: 1, wherein said method comprises the step of heating the sample at a temperature of from about 53° C. to about 67° C. to inactivate said proteinase or enzymatically active fragment, and wherein
   i) the concentration of free calcium in said sample is ≤about 80 μM; or
   ii) the concentration of monovalent salt in said sample is ≥about 20 mM.

2. The method of claim 1, wherein said heating step comprises heating the sample at a temperature of from about 53° C. to about 58° C.

3. The method of claim 2, wherein the concentration of free calcium in the sample is ≤about 10 μM, or the concentration of monovalent salt in the sample is at least about 75 mM.

4. The method of claim 1, wherein said heating step comprises heating the sample at a temperature of from about 63° C. to about 67° C.

5. The method of claim 4, wherein the concentration of free calcium in the sample is ≤about 65 μM, or the concentration of monovalent salt in the sample is at least about 25 mM.

6. The method of claim 1, wherein said heating step comprises heating the sample at a temperature of from about 58° C. to about 63° C.

7. The method of claim 6, wherein said heating step comprises heating the sample for
   i) about 5 to 15 minutes, wherein the concentration of free calcium in the sample is ≤about 10 μM, or the concentration of monovalent salt in the sample is at least about 75 mM; or
   ii) about 10 to 20 minutes, wherein the concentration of free calcium in the sample is ≤about 35 μM, or the concentration of monovalent salt in the sample is at least about 50 mM; or
   i) about 20 to 40 minutes, wherein the concentration of free calcium in the sample is ≤about 65 μM, or the concentration of monovalent salt in the sample is at least about 25 mM.

8. The method of claim 1, wherein any remaining proteinase activity of the proteinase or enzymatically active fragment thereof after said heating step is ≤about 25% as compared to a control, wherein said remaining activity is determined by the following assay steps:

i) incubating in a 1000 μl or 250 μl cuvette:
   10 to 50 mU/mL heat-treated proteinase, 1 mM substrate Suc-Ala-Ala-Pro-Phe-pNA, ≤15 mM NaCl, 0.1 mM Tris-HCl of a pH of 8, 10 mM CaCl$_2$), and optionally 1% DMSO;
ii) assaying cleavage of the substrate to 4-nitroalinine by measuring the increase in absorbance at 410 nm (ε=8800 M$^{-1}$·cm$^{-1}$) over 2 minutes via a spectrophotometer at a temperature ≤40° C., wherein one Unit is defined as an amount of enzyme that produces one μmol 4-nitroaniline per minute at the chosen temperature; and
iii) comparing the activity observed in step ii) to the activity observed with the same amount of the proteinase that has not been heat-treated but has been otherwise kept under the same conditions as the heat-treated proteinase, by the same assay.

9. The method of claim 1, wherein said sample comprises:
a) one or more further enzymes selected from the group consisting of: a nuclease, a DNA or RNA polymerase, a reverse transcriptase, a DNA ligase, an RNA ligase, a methylase, a transferase, a topoisomerase, a guanylyl transferase, a phosphatase, a transposase, a kinase, a helicase, a restriction enzyme, and a glycosylase;
b) one or more nucleic acid molecules, and wherein the method comprises, subsequent to said step of heating the sample to inactivate said proteinase, a step of:
   i) nuclease-mediated digestion of the one or more nucleic acid molecules;
   ii) phosphorylation or de-phosphorylation of the one or more nucleic acid molecules; or
   iii) ligation of the one or more nucleic acid molecules;
without prior removal or dilution of the proteinase or enzymatically active fragment thereof;
c) one or more RNA molecules, and wherein the method comprises, subsequent to said step of heating the sample to inactivate said proteinase, a step of reverse transcription without prior removal or dilution of the proteinase or enzymatically active fragment thereof;
d) one or more DNA molecules, and wherein the method comprises, subsequent to said step of heating the sample to inactivate said proteinase, a step of nucleic acid polymerisation, preferably amplification, without prior removal or dilution of the proteinase or enzymatically active fragment thereof; or
e) one or more virus particles or cells, and the method comprises, subsequent to said step of heating the sample to inactivate said proteinase, a step of cell lysis without prior removal or dilution of the proteinase or enzymatically active fragment thereof.

* * * * *

SEQUENCE LISTING

```
<160> NUMBER OF SEQ ID NOS: 4

<210> SEQ ID NO 1
<211> LENGTH: 281
<212> TYPE: PRT
<213> ORGANISM: Serratia proteamaculans

<400> SEQUENCE: 1

Ala Asp Gln Pro Ser Pro Thr Trp Gly Ile Asp Arg Ile Asp Gln Arg
1               5                   10                  15

Asn Leu Pro Leu Asp Asn Asn Tyr His Thr Asp Tyr Asp Gly Ser Gly
            20                  25                  30

Val Thr Ala Phe Val Ile Asp Thr Gly Val Leu Asn Thr His Asn Glu
        35                  40                  45

Phe Gly Gly Arg Ala Ser Ser Gly Tyr Asp Phe Ile Asp Asn Asp Tyr
    50                  55                  60

Asp Ala Thr Asp Cys Asn Gly His Gly His Val Ala Gly Thr Ile
65                  70                  75                  80
```

```
Gly Gly Ser Thr Tyr Gly Val Ala Lys Asn Val Asn Val Gly Val
                 85                  90                  95

Arg Val Leu Asn Cys Ser Gly Gly Ser Asn Ser Gly Val Ile Ala
            100                 105                 110

Gly Ile Asn Trp Val Lys Asn Asn Ala Ser Gly Pro Ala Val Ala Asn
        115                 120                 125

Met Ser Leu Gly Gly Gly Ala Ser Gln Ala Thr Asp Asp Ala Val Asn
130             135                 140

Ala Ala Val Ala Ala Gly Ile Thr Phe Val Val Ala Ala Gly Asn Asp
145             150                 155                 160

Asn Ser Asn Ala Cys Asn Tyr Ser Pro Ala Arg Ala Ala Asp Ala Ile
                165                 170                 175

Thr Val Gly Ser Thr Thr Ser Asn Asp Ser Arg Ser Ser Phe Ser Asn
            180                 185                 190

Tyr Gly Thr Cys Leu Asp Ile Tyr Ala Pro Gly Ser Ser Ile Thr Ser
        195                 200                 205

Ser Trp Tyr Thr Ser Asn Ser Ala Thr Asn Thr Ile Ser Gly Thr Ser
    210                 215                 220

Met Ala Ser Pro His Val Ala Gly Val Ala Ala Leu Tyr Leu Asp Glu
225             230                 235                 240

Asn Pro Asn Leu Ser Pro Ala Gln Val Thr Asn Leu Leu Lys Thr Arg
                245                 250                 255

Ala Thr Ala Asp Lys Val Thr Asp Ala Lys Thr Gly Ser Pro Asn Lys
            260                 265                 270

Leu Leu Phe Ser Leu Ala Asn Asp Asp
        275                 280

<210> SEQ ID NO 2
<211> LENGTH: 1890
<212> TYPE: DNA
<213> ORGANISM: Serratia proteamaculans

<400> SEQUENCE: 2
atgcataaga aacatttaat agcagtcgca gtcgcaacgg gacttgctta cttccctgtt      60
aacgctaatg aataccaagc gactatggta atgtcccac aatctaaagc catcaaagat      120
acttacatcg ttgtattcaa taccccaagt gttcttaatc taagtaataa caacaccata      180
gctgaattcg cggttcaaca agccgagagt ttagtcaatc aatatgatgt cagagtgatg      240
aaaaactttg gcaatgtgct caacggtgta ctcatcaatg ccagtgccca acaagttaaa      300
gcactgctta agatccaaa cgtgaagtac gtagaacaag atcaagtgat gtcagtaacg      360
cccatgatgg aagccaatgc ggaccaaccg agtccgacct ggggcataga cagaatcgat      420
caacgcaact tgccattgga taacaactac cacacggatt acgatggatc tggtgtgacc      480
gcctttgtta ttgatactgg ggtgcttaat acacacaatg agtttggcgg ccgcgcaagc      540
agtggctatg actttatcga taatgattac gatgcgactg actgtaacgg tcatggtacc      600
catgtggcgg ggacgattgg cggctcaacc tacggtgtcg cgaaaaacgt caatgtggtg      660
ggcgtcagag tgcttaactg ttcaggttct ggcagtaact ctggcgtgat tgcaggata       720 aactgggtga aaacaatgc ttctggcccc gctgtcgcga acatgagttt agggggcggc      780
gcctcccaag ccacggatga tgccgtcaat gccgctgttg ccgcagggat caccttcgtc      840
gtcgcagccg gcaatgacaa tagtaatgcc tgtaattatt cacctgctcg tgccgcagat      900
gccatcactg tcggttcaac caccagtaac gattcccgct cgagtttttc taactacggg      960
```

```
acttgccttg atatctatgc gcccggttcg agcataactt cctcttggta tacctcaaat   1020
tcggcgacta ataccattag tggcacctca atggcttccc cccatgtggc aggcgtcgcg   1080
gcattatact tagatgaaaa tcctaacctc tcccccgcac aggtgactaa cttactcaag   1140
acgcgcgcca ctgcggacaa agtcacagat gctaagacag gctcaccgaa taagttactg   1200
ttttcacttg caaacgatga tggaggctgt ggcaacgatt gcccagttga cgagactcag   1260
ctgcaaaata atgtgggtat tgcgatcagt ggagccacag gttcagcgac ttattactat   1320
atcgatgtcc ccgcaaatgc agcaagttta ggcatcaacc tcgcgggggg ctctggcgat   1380
gcggatattt atgtgagcca aggacaaaaa ccgactacga ccagctatca atgccgccca   1440
tatcaaaatg caacaatga gctgtaat ttcactgcac ctacggcggg tcgttggtac   1500
gtgatggttc aaggctatag caattatgcc aacgcccagc tgacagctag ctacaacctc   1560
aatggcggcg gaaattgtac cgatgcgaac tgcttaagca atggcgtacc cgtcacgaat   1620
ttaagcggca gaacgggaac tgaagccctg tataaaatcg tcgtccctgc gaatagccaa   1680
ctcagtatta ccaccagtgg cgggactggt gacgtggatc tgtatgtcaa agcagggact   1740
gtcccaacga ccaccagcta tgattgtcgt ccctataaaa acggtaacaa tgaaagctgt   1800
tcaatcaccg tgactcaagc gggaacttac catgtgatgt tacgtggtta tgctaattac   1860
tcgagcgttc agctgagtgc aagctactag                                    1890

<210> SEQ ID NO 3
<211> LENGTH: 629
<212> TYPE: PRT
<213> ORGANISM: Serratia proteamaculans

<400> SEQUENCE: 3

Met His Lys Lys His Leu Ile Ala Val Ala Val Ala Thr Gly Leu Ala
1               5                   10                  15

Tyr Phe Pro Val Asn Ala Asn Glu Tyr Gln Ala Thr Met Val Asn Val
                20                  25                  30

Pro Gln Ser Lys Ala Ile Lys Asp Thr Tyr Ile Val Val Phe Asn Thr
            35                  40                  45

Pro Ser Val Leu Asn Leu Ser Asn Asn Thr Ile Ala Glu Phe Ala
        50                  55                  60

Val Gln Gln Ala Glu Ser Leu Val Asn Gln Tyr Asp Val Arg Val Met
65                  70                  75                  80

Lys Asn Phe Gly Asn Val Leu Asn Gly Val Leu Ile Asn Ala Ser Ala
                85                  90                  95

Gln Gln Val Lys Ala Leu Leu Lys Asp Pro Asn Val Lys Tyr Val Glu
            100                 105                 110

Gln Asp Gln Val Met Ser Val Thr Pro Met Met Glu Ala Asn Ala Asp
        115                 120                 125

Gln Pro Ser Pro Thr Trp Gly Ile Asp Arg Ile Asp Gln Arg Asn Leu
    130                 135                 140

Pro Leu Asp Asn Asn Tyr His Thr Asp Tyr Asp Gly Ser Gly Val Thr
145                 150                 155                 160

Ala Phe Val Ile Asp Thr Gly Val Leu Asn Thr His Asn Glu Phe Gly
                165                 170                 175

Gly Arg Ala Ser Ser Gly Tyr Asp Phe Ile Asp Asn Asp Tyr Asp Ala
            180                 185                 190

Thr Asp Cys Asn Gly His Gly Thr His Val Ala Gly Thr Ile Gly Gly
        195                 200                 205
```

```
Ser Thr Tyr Gly Val Ala Lys Asn Val Asn Val Val Gly Val Arg Val
    210                 215                 220

Leu Asn Cys Ser Gly Ser Gly Ser Asn Ser Gly Val Ile Ala Gly Ile
225                 230                 235                 240

Asn Trp Val Lys Asn Asn Ala Ser Gly Pro Ala Val Ala Asn Met Ser
                245                 250                 255

Leu Gly Gly Gly Ala Ser Gln Ala Thr Asp Asp Ala Val Asn Ala Ala
                260                 265                 270

Val Ala Ala Gly Ile Thr Phe Val Ala Ala Gly Asn Asp Asn Ser
            275                 280                 285

Asn Ala Cys Asn Tyr Ser Pro Ala Arg Ala Ala Asp Ala Ile Thr Val
    290                 295                 300

Gly Ser Thr Thr Ser Asn Asp Ser Arg Ser Ser Phe Ser Asn Tyr Gly
305                 310                 315                 320

Thr Cys Leu Asp Ile Tyr Ala Pro Gly Ser Ser Ile Thr Ser Ser Trp
                325                 330                 335

Tyr Thr Ser Asn Ser Ala Thr Asn Thr Ile Ser Gly Thr Ser Met Ala
                340                 345                 350

Ser Pro His Val Ala Gly Val Ala Ala Leu Tyr Leu Asp Glu Asn Pro
                355                 360                 365

Asn Leu Ser Pro Ala Gln Val Thr Asn Leu Leu Lys Thr Arg Ala Thr
    370                 375                 380

Ala Asp Lys Val Thr Asp Ala Lys Thr Gly Ser Pro Asn Lys Leu Leu
385                 390                 395                 400

Phe Ser Leu Ala Asn Asp Asp Gly Gly Cys Gly Asn Asp Cys Pro Val
                405                 410                 415

Asp Glu Thr Gln Leu Gln Asn Asn Val Gly Ile Ala Ile Ser Gly Ala
                420                 425                 430

Thr Gly Ser Ala Thr Tyr Tyr Tyr Ile Asp Val Pro Ala Asn Ala Ala
                435                 440                 445

Ser Leu Gly Ile Asn Leu Ala Gly Gly Ser Gly Asp Ala Asp Ile Tyr
    450                 455                 460

Val Ser Gln Gly Gln Lys Pro Thr Thr Thr Ser Tyr Gln Cys Arg Pro
465                 470                 475                 480

Tyr Gln Asn Gly Asn Asn Glu Ser Cys Asn Phe Thr Ala Pro Thr Ala
                485                 490                 495

Gly Arg Trp Tyr Val Met Val Gln Gly Tyr Ser Asn Tyr Ala Asn Ala
                500                 505                 510

Gln Leu Thr Ala Ser Tyr Asn Leu Asn Gly Gly Asn Cys Thr Asp
                515                 520                 525

Ala Asn Cys Leu Ser Asn Gly Val Pro Val Thr Asn Leu Ser Gly Arg
    530                 535                 540

Thr Gly Thr Glu Ala Leu Tyr Lys Ile Val Val Pro Ala Asn Ser Gln
545                 550                 555                 560

Leu Ser Ile Thr Thr Ser Gly Gly Thr Gly Asp Val Asp Leu Tyr Val
                565                 570                 575

Lys Ala Gly Thr Val Pro Thr Thr Thr Ser Tyr Asp Cys Arg Pro Tyr
                580                 585                 590

Lys Asn Gly Asn Asn Glu Ser Cys Ser Ile Thr Val Thr Gln Ala Gly
                595                 600                 605

Thr Tyr His Val Met Leu Arg Gly Tyr Ala Asn Tyr Ser Ser Val Gln
    610                 615                 620

Leu Ser Ala Ser Tyr
```

<210> SEQ ID NO 4
<211> LENGTH: 385
<212> TYPE: PRT
<213> ORGANISM: Serratia proteamaculans

<400> SEQUENCE: 4

```
Asn Glu Tyr Gln Ala Thr Met Val Asn Val Pro Gln Ser Lys Ala Ile
1               5                   10                  15

Lys Asp Thr Tyr Ile Val Val Phe Asn Thr Pro Ser Val Leu Asn Leu
            20                  25                  30

Ser Asn Asn Thr Ile Ala Glu Phe Ala Val Gln Gln Ala Glu Ser
        35                  40                  45

Leu Val Asn Gln Tyr Asp Val Arg Val Met Lys Asn Phe Gly Asn Val
    50                  55                  60

Leu Asn Gly Val Leu Ile Asn Ala Ser Ala Gln Gln Val Lys Ala Leu
65                  70                  75                  80

Leu Lys Asp Pro Asn Val Lys Tyr Val Glu Gln Asp Gln Val Met Ser
                85                  90                  95

Val Thr Pro Met Met Glu Ala Asn Ala Asp Gln Pro Ser Pro Thr Trp
            100                 105                 110

Gly Ile Asp Arg Ile Asp Gln Arg Asn Leu Pro Leu Asp Asn Asn Tyr
        115                 120                 125

His Thr Asp Tyr Asp Gly Ser Gly Val Thr Ala Phe Val Ile Asp Thr
    130                 135                 140

Gly Val Leu Asn Thr His Asn Glu Phe Gly Gly Arg Ala Ser Ser Gly
145                 150                 155                 160

Tyr Asp Phe Ile Asp Asn Asp Tyr Asp Ala Thr Asp Cys Asn Gly His
                165                 170                 175

Gly Thr His Val Ala Gly Thr Ile Gly Gly Ser Thr Tyr Gly Val Ala
            180                 185                 190

Lys Asn Val Asn Val Val Gly Val Arg Val Leu Asn Cys Ser Gly Ser
        195                 200                 205

Gly Ser Asn Ser Gly Val Ile Ala Gly Ile Asn Trp Val Lys Asn Asn
    210                 215                 220

Ala Ser Gly Pro Ala Val Ala Asn Met Ser Leu Gly Gly Gly Ala Ser
225                 230                 235                 240

Gln Ala Thr Asp Asp Ala Val Asn Ala Ala Val Ala Ala Gly Ile Thr
                245                 250                 255

Phe Val Val Ala Ala Gly Asn Asp Asn Ser Asn Ala Cys Asn Tyr Ser
            260                 265                 270

Pro Ala Arg Ala Ala Asp Ala Ile Thr Val Gly Ser Thr Thr Ser Asn
        275                 280                 285

Asp Ser Arg Ser Ser Phe Ser Asn Tyr Gly Thr Cys Leu Asp Ile Tyr
    290                 295                 300

Ala Pro Gly Ser Ser Ile Thr Ser Ser Trp Tyr Thr Ser Asn Ser Ala
305                 310                 315                 320

Thr Asn Thr Ile Ser Gly Thr Ser Met Ala Ser Pro His Val Ala Gly
                325                 330                 335

Val Ala Ala Leu Tyr Leu Asp Glu Asn Pro Asn Leu Ser Pro Ala Gln
            340                 345                 350

Val Thr Asn Leu Leu Lys Thr Arg Ala Thr Ala Asp Lys Val Thr Asp
        355                 360                 365
```

```
Ala Lys Thr Gly Ser Pro Asn Lys Leu Leu Phe Ser Leu Ala Asn Asp
    370                 375                 380
Asp
385
```